(12) United States Patent
Manolidis

(10) Patent No.: US 12,279,983 B2
(45) Date of Patent: Apr. 22, 2025

(54) DUAL STENT AND DELIVERY SYSTEM, DELIVERY TOOL APPARATUS, AND METHOD OF DELIVERY OF DUAL STENTS

(71) Applicant: TENSOR FLOW VENTURES LLC, Dallas, TX (US)

(72) Inventor: Spiros Manolidis, Southlake, TX (US)

(73) Assignee: Tensor Flow Ventures LLC, Dallas, TX (US)

( * ) Notice: Subject to any disclaimer, the term of this patent is extended or adjusted under 35 U.S.C. 154(b) by 0 days.

(21) Appl. No.: 18/658,650

(22) Filed: May 8, 2024

(65) Prior Publication Data

US 2024/0293245 A1  Sep. 5, 2024

Related U.S. Application Data

(63) Continuation of application No. 18/196,663, filed on May 12, 2023, which is a continuation-in-part of application No. 17/873,081, filed on Jul. 25, 2022.

(60) Provisional application No. 63/341,844, filed on May 13, 2022, provisional application No. 63/225,867, filed on Jul. 26, 2021.

(51) Int. Cl.
*A61F 2/966* (2013.01)
*A61B 17/11* (2006.01)
*A61F 2/82* (2013.01)

(52) U.S. Cl.
CPC ....... *A61F 2/966* (2013.01); *A61B 2017/1107* (2013.01); *A61B 2017/1125* (2013.01); *A61F 2002/826* (2013.01)

(58) Field of Classification Search
CPC ............... A61F 2/966; A61F 2002/826; A61B 2017/1107; A61B 2017/1125
See application file for complete search history.

(56) References Cited

U.S. PATENT DOCUMENTS

| | | |
|---|---|---|
| 4,054,128 A | 10/1977 | Seufert et al. |
| 4,832,055 A | 5/1989 | Palestrant |
| 4,873,965 A | 10/1989 | Danieli |
| 5,141,516 A | 8/1992 | Detweiler |
| 5,349,133 A | 9/1994 | Rogers |
| 5,492,131 A | 2/1996 | Galel |
| 5,507,725 A | 4/1996 | Savage et al. |
| 5,536,236 A | 7/1996 | Yabe et al. |
| 5,562,641 A | 10/1996 | Flomenblit et al. |

(Continued)

FOREIGN PATENT DOCUMENTS

| | | |
|---|---|---|
| CN | 104116484 A | 10/2014 |
| DE | 102016007669 A1 | 12/2017 |

(Continued)

*Primary Examiner* — Richard G Louis
(74) *Attorney, Agent, or Firm* — David W. Carstens; James H. Ortega; Carstens, Allen & Gourley, LLP

(57) ABSTRACT

A method, system, or apparatus for stent delivery. Delivering one or more stents with a delivery tool that can include a kinetic transfer of energy to deliver one or more stents. The stents can include a modifiable stent that can change its overall shape and/or dimensions based on pre-configured design parameters. A coil stent that can engage with a vessel that surrounds the modifiable stent forming a dual stent configuration. The coil stent can also include anchor points that allow it to engage with a second vessel securing the first vessel and the second vessel together to aid in the healing process.

20 Claims, 19 Drawing Sheets

(56) References Cited

U.S. PATENT DOCUMENTS

| | | | |
|---|---|---|---|
| 5,573,493 A | 11/1996 | Sauer et al. | |
| 5,733,325 A | 3/1998 | Robinson et al. | |
| 5,735,859 A | 4/1998 | Fischell et al. | |
| 5,746,766 A | 5/1998 | Edoga | |
| 5,752,960 A * | 5/1998 | Nallakrishnan | A61F 2/1664 |
| | | | 606/205 |
| 5,851,218 A | 12/1998 | Lev | |
| 5,941,908 A * | 8/1999 | Goldsteen | A61F 2/064 |
| | | | 606/198 |
| 5,968,091 A | 10/1999 | Pinchuk et al. | |
| 6,083,257 A | 7/2000 | Taylor et al. | |
| 6,270,524 B1 | 8/2001 | Kim | |
| 6,361,559 B1 | 3/2002 | Houser et al. | |
| 6,485,513 B1 | 11/2002 | Fan | |
| 6,517,574 B1 | 2/2003 | Chuter | |
| 6,565,581 B1 | 5/2003 | Spence et al. | |
| 6,699,263 B2 | 3/2004 | Cope | |
| 6,786,919 B1 | 9/2004 | Escano et al. | |
| 6,899,672 B2 | 5/2005 | Chin et al. | |
| 7,090,637 B2 | 8/2006 | Danitz et al. | |
| 7,476,256 B2 | 1/2009 | Meade et al. | |
| 7,678,068 B2 | 3/2010 | Levine et al. | |
| 7,766,962 B1 | 8/2010 | Quinn | |
| 8,097,009 B2 | 1/2012 | Wu et al. | |
| 8,211,025 B2 | 7/2012 | Donaldson et al. | |
| 8,298,161 B2 | 10/2012 | Vargas | |
| 8,360,968 B2 | 1/2013 | Hadani | |
| 8,444,549 B2 | 5/2013 | Viola et al. | |
| 8,512,232 B2 | 8/2013 | Rothberg et al. | |
| 8,615,288 B2 | 12/2013 | Govari et al. | |
| 8,920,482 B2 | 12/2014 | McHugo | |
| 9,220,568 B2 | 12/2015 | Bromander et al. | |
| 9,326,870 B2 | 5/2016 | Berglund et al. | |
| 9,757,856 B2 | 9/2017 | Oyola et al. | |
| 9,820,746 B2 | 11/2017 | Imran | |
| 9,949,692 B2 | 4/2018 | Hunter | |
| 10,299,950 B2 | 5/2019 | Campbell et al. | |
| 10,327,934 B2 | 6/2019 | Havel et al. | |
| 10,420,661 B2 | 9/2019 | Hodgkinson et al. | |
| 10,542,931 B2 | 1/2020 | Kuraguntla et al. | |
| 10,687,969 B2 | 6/2020 | Folan et al. | |
| 11,033,377 B2 | 6/2021 | Houston et al. | |
| 11,039,838 B2 | 6/2021 | Binmoeller et al. | |
| 11,259,945 B2 | 3/2022 | Berra | |
| 11,491,003 B2 | 11/2022 | Arbefeuille et al. | |
| 11,596,408 B2 | 3/2023 | Lukin et al. | |
| 11,666,464 B2 | 6/2023 | Manolidis | |
| 11,696,843 B2 | 7/2023 | Pung et al. | |
| 11,724,009 B2 | 8/2023 | Paquin et al. | |
| 2001/0004696 A1 | 6/2001 | Roberts et al. | |
| 2001/0047197 A1 | 11/2001 | Foley | |
| 2002/0029076 A1 | 3/2002 | Yee | |
| 2002/0099405 A1 | 7/2002 | Yurek et al. | |
| 2002/0143347 A1 | 10/2002 | Cole et al. | |
| 2002/0151957 A1 | 10/2002 | Kerr | |
| 2002/0173809 A1 | 11/2002 | Fleischman et al. | |
| 2003/0065375 A1 | 4/2003 | Eskuri | |
| 2003/0135266 A1 | 7/2003 | Chew et al. | |
| 2003/0216801 A1 | 11/2003 | Tweden et al. | |
| 2003/0225445 A1 | 12/2003 | Derus et al. | |
| 2004/0082945 A1 | 4/2004 | Clague et al. | |
| 2004/0116999 A1 | 6/2004 | Ledergerber | |
| 2004/0167604 A1 | 8/2004 | Stinson | |
| 2005/0049480 A1 | 3/2005 | Gray | |
| 2005/0154444 A1 | 7/2005 | Quadri | |
| 2005/0154448 A1 | 7/2005 | Cully et al. | |
| 2006/0052736 A1 | 3/2006 | Tweden et al. | |
| 2006/0074478 A1 | 4/2006 | Feller | |
| 2006/0149349 A1 | 7/2006 | Garbe | |
| 2006/0211984 A1 | 9/2006 | Blank et al. | |
| 2007/0055339 A1 | 3/2007 | George et al. | |
| 2007/0067014 A1 | 3/2007 | Ke et al. | |
| 2007/0106373 A1 | 5/2007 | Houston et al. | |
| 2007/0142711 A1 | 6/2007 | Bayer et al. | |
| 2007/0179598 A1 | 8/2007 | Duerig | |

| | | |
|---|---|---|
| 2008/0132906 A1 | 6/2008 | Rasmussen |
| 2008/0255653 A1 | 10/2008 | Schkolnik |
| 2009/0023998 A1 | 1/2009 | Ratnakar |
| 2009/0171437 A1 | 7/2009 | Brocker et al. |
| 2009/0281557 A1 | 11/2009 | Sander et al. |
| 2009/0287293 A1 | 11/2009 | Mailhot |
| 2010/0030320 A1 | 2/2010 | Feller |
| 2010/0094398 A1 | 4/2010 | Malewicz |
| 2010/0168835 A1 | 7/2010 | Dorn |
| 2010/0217082 A1 | 8/2010 | Ito et al. |
| 2010/0262171 A1 | 10/2010 | Wu et al. |
| 2011/0190870 A1 | 8/2011 | Hastings et al. |
| 2011/0264196 A1 | 10/2011 | Savage et al. |
| 2012/0071721 A1 | 3/2012 | Remijan et al. |
| 2012/0123464 A1 | 5/2012 | Rasmussen et al. |
| 2012/0143269 A1 | 6/2012 | Ichelmann et al. |
| 2012/0290072 A1 | 11/2012 | Theobald et al. |
| 2012/0296406 A1 | 11/2012 | Minion |
| 2013/0035751 A1 | 2/2013 | Shalev |
| 2013/0144380 A1 | 6/2013 | Quadri et al. |
| 2013/0190741 A1 | 7/2013 | Moll et al. |
| 2013/0331927 A1 | 12/2013 | Zheng et al. |
| 2014/0081415 A1 | 3/2014 | Ruberti et al. |
| 2014/0228936 A1 | 8/2014 | Kassab et al. |
| 2014/0236064 A1 | 8/2014 | Binmoeller et al. |
| 2014/0277442 A1 | 9/2014 | Seddon et al. |
| 2014/0303599 A1 | 10/2014 | Heideman et al. |
| 2015/0328022 A1 | 11/2015 | Hansen et al. |
| 2015/0366439 A1 | 12/2015 | Luo et al. |
| 2016/0120638 A1 | 5/2016 | Michalak |
| 2016/0242940 A1 | 8/2016 | Krautkremer et al. |
| 2016/0256610 A1 | 9/2016 | Zhou et al. |
| 2016/0310077 A1 | 10/2016 | Hunter et al. |
| 2017/0079785 A1 | 3/2017 | Li |
| 2017/0086929 A1 | 3/2017 | Moll et al. |
| 2017/0128072 A1 | 5/2017 | Wang et al. |
| 2017/0224467 A1 | 8/2017 | Piccagli et al. |
| 2017/0296038 A1 | 10/2017 | Gordon et al. |
| 2017/0330665 A1 | 11/2017 | Zareei et al. |
| 2018/0207007 A1 | 7/2018 | Giasolli et al. |
| 2019/0239879 A1 | 8/2019 | Zilla et al. |
| 2020/0094398 A1 | 3/2020 | Young et al. |
| 2020/0170776 A1 | 6/2020 | Folan |
| 2020/0237534 A1 | 7/2020 | Manolidis |
| 2020/0237539 A1 | 7/2020 | Manolidis |
| 2020/0237540 A1 | 7/2020 | Manolidis |
| 2021/0052403 A1 | 2/2021 | Chu et al. |
| 2021/0077247 A1 | 3/2021 | Shalev et al. |
| 2021/0205007 A1 | 7/2021 | Anderson et al. |
| 2021/0393424 A1 | 12/2021 | McWeeney et al. |
| 2022/0273365 A1 | 9/2022 | Rege et al. |
| 2022/0303150 A1 | 9/2022 | Jensen et al. |
| 2023/0026939 A1 | 1/2023 | Manolidis et al. |
| 2023/0048537 A1 | 2/2023 | Arbefeuille et al. |
| 2023/0132550 A1 | 5/2023 | Vong et al. |
| 2023/0277294 A1 | 9/2023 | Folan |
| 2023/0310184 A1 | 10/2023 | Manolidis |
| 2023/0310186 A1 | 10/2023 | Nagano et al. |
| 2023/0355381 A1 | 11/2023 | Peckels et al. |

FOREIGN PATENT DOCUMENTS

| | | |
|---|---|---|
| EP | 2063823 A2 | 6/2009 |
| GB | 2452480 A | 3/2009 |
| JP | 2012065933 A | 4/2012 |
| WO | 9415549 A1 | 7/1994 |
| WO | 9423669 A1 | 10/1994 |
| WO | 0045737 A1 | 8/2000 |
| WO | 02056798 A2 | 7/2002 |
| WO | 2005037361 A2 | 4/2005 |
| WO | 2008025855 A2 | 3/2008 |
| WO | 2008066917 A1 | 6/2008 |
| WO | 2009091899 A2 | 7/2009 |
| WO | 2011116913 A1 | 9/2011 |
| WO | 2016069274 A1 | 5/2016 |
| WO | 2016134148 A1 | 8/2016 |

(56) References Cited

FOREIGN PATENT DOCUMENTS

| WO | 2018005861 A1 | 1/2018 |
|----|---------------|--------|
| WO | 2018068106 A1 | 4/2018 |

\* cited by examiner

DUAL STENT AND DELIVERY SYSTEM, DELIVERY TOOL APPARATUS, AND METHOD OF DELIVERY OF DUAL STENTS

CROSS-REFERENCE TO RELATED APPLICATIONS

The present disclosure incorporates by reference in their entireties for all purposes U.S. patent application Ser. No. 16/752,265, filed Jan. 24, 2020, which claims priority from U.S. Provisional Patent Application No. 62/797,932, filed Jan. 28, 2019; U.S. patent application Ser. No. 16/752,315, filed Jan. 24, 2020, which claims priority from U.S. Provisional Patent Application No. 62/797,933, filed Jan. 28, 2019; and U.S. patent application Ser. No. 16/752,343, filed Jan. 24, 2020, which claims priority from U.S. Provisional Patent Application No. 62/797,944, filed Jan. 28, 2019.

The present disclosure is a continuation of U.S. patent application Ser. No. 18/196,663, filed May 12, 2023, which claims priority to U.S. Provisional Patent Application No. 63/341,844, filed on May 13, 2022, and which is a continuation-in-part of U.S. patent application Ser. No. 17/873,081, filed on Jul. 25, 2022, which claims priority from U.S. Provisional Patent Application No. 63/225,867, filed Jul. 26, 2021, that are each incorporated by reference in their entirety for all purposes.

BACKGROUND

Technical Field

The present disclosure relates to dual stents and the delivery of same. More particularly, and not by way of limitation, the present disclosure is directed to a system, apparatus, or method for aiding in healing through the use of dual stents or the delivery of dual stents.

Description of Related Art

There are many different types of surgeries that can be conducted daily in hospitals across the world. One such surgery is free flap reconstruction. Free flap reconstruction is a well-established method of reconstruction of both soft tissue and bone or composite defects in a wide variety of surgeries. Free flaps are used in order of frequency in head and neck reconstruction, breast reconstruction, orthopedic surgery and a variety of other specialties. Head and neck surgery in particular is a heavy user of free flap reconstruction. This is due to the complexity of defects in a critical area where restoration of functions such as deglutition, phonation, and mastication is of paramount importance in addition to cosmesis.

Free flap reconstruction involves the transfer of tissue from a distant part of the body to the area that needs to be reconstructed. The principle in operation behind this concept is that tissues in the body are supplied in a segmental function. That is that a segment of skin subcutaneous tissue fascia muscle bone, or any combination of these can be harvested according to specific location. The transfer of tissue is completed when the free flap vessels (artery and vein) are joined to the donor vessels and then the flap is set into the defect.

Donor vessels are selected from appropriate vessels to match the diameter of the recipient vessels (free flap vessels). In the neck, these are usually branches of the external carotid artery and one of the many veins in the head and neck or the jugular vein itself. Each of the donor vessels are dissected from surrounding tissue, and their edges prepared for anastomosis. In free flap reconstruction, vessels are raised in situ and the vascular supply is dissected out carefully and traumatically. The vascular supply is then sectioned, preferably at a length of vessel that is appropriate for an anastomosis without tension. This is not always possible as different free flaps have different lengths of vessels according to where they are harvested. For example, free rectus vascular pedicle may have a max length of 8 cm, while a radial forearm vascular pedicle may have a max length of 15-20 cm.

Once the vessels are extracted from the appropriate location, the edge preparation begins. The vessel preparation process can take approximately one hour and is performed under optimal conditions with an operating microscope and/or magnifying loops. Considerable skill is required that comes with prolonged surgical training. The anastomoses (joining) themselves are approximately 20 minutes per vessel anastomosis. Venous couplers reduce the amount of time required for venous anastomoses. However, these venous couplers still require suturing for each venous anastomoses, taking considerable time and increasing the time a patient is under anesthesia. There are two general types of anastomoses, an end to end and an end to side. An end-to-end anastomosis is preferred because it is performed rapidly without additional problems and because the vascular dynamics are that of linear flow which gives lesser complication rates. End to end anastomoses account for the majority of vessel joining. However, currently these operations and/or couplings still require significant suturing time, that can lead to other complications.

It would be advantageous to have a system, apparatus, or method that overcomes the disadvantages of the prior art. The present disclosure provides such a system, apparatus, or method.

BRIEF SUMMARY

The present disclosure is directed to stent delivery.

Thus, in one aspect, the present disclosure is directed to delivering one or more stents with a delivery tool that can include a kinetic transfer of energy to deliver one or more stents.

In another aspect, the present disclosure is directed to a modifiable stent that can change its overall shape and/or dimensions based on pre-configured design parameters.

In yet another aspect, the present disclosure is directed to a coil stent that can engage with a vessel that surrounds the modifiable stent forming a dual stent configuration. The coil stent may also include anchor points that allow it to engage with a second vessel securing the first vessel and the second vessel together to aid in the healing process.

BRIEF DESCRIPTION OF THE DRAWINGS

The novel features believed characteristic of the disclosure are set forth in the appended claims. The disclosure itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Figure 1A:
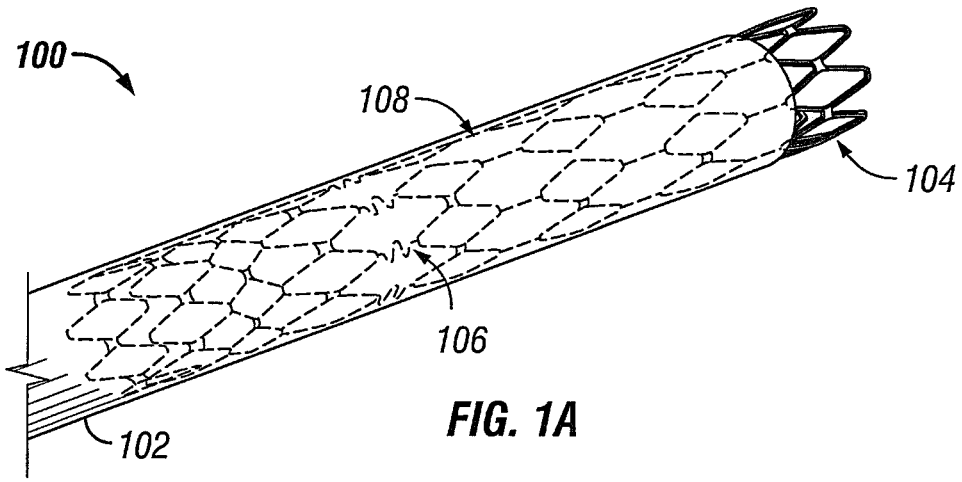
FIG. 1A is a perspective view illustration of a vessel with a modifiable stent received within the vessel.

An embodiment of the disclosure will now be described. While the present disclosure is related to stents and/or stent delivery, the tools described herein may also be utilized with vessels, arteries, and/or veins. FIG. 1A is a perspective view illustration of a vessel 102 with a modifiable stent 104 received within the vessel 102. The stent system 100 can allow for the engagement of a modified stent 104 with a vessel, such as a donor vessel 102. In at least one embodiment, the stent system 100 can allow for faster engagement of vessels during surgeries. The modifiable stent 104 may comprise a modifiable member 106 and/or a non-modifiable member 108. In at least one example, the modifiable stent 104 can change its diameter and/or radius via the modifiable member(s) 106. The modifiable stent 104 may be modified inward or outward, for example, decreasing the diameter or increasing the diameter of the modifiable stent to engage with a vessel, such as a donor vessel 102. In some examples, the length of the modifiable stent 104 can be increased or decreased via the modifiable member(s) 106 and/or non-modifiable member 108.

Figure 1B:
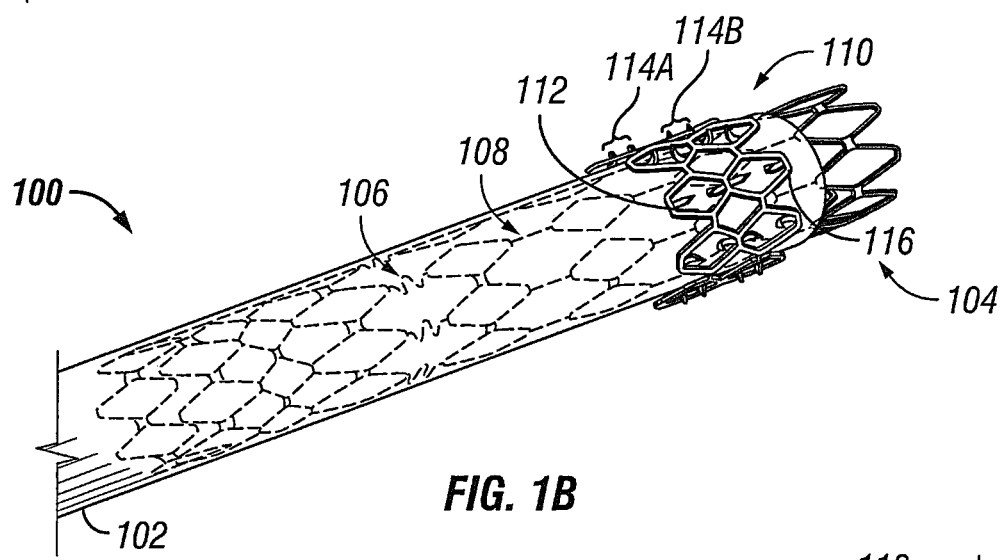
FIG. 1B is a perspective view illustration of a vessel with a modifiable stent received within the vessel and a coil stent surrounding the vessel and a portion of the modifiable stent.

FIG. 1B is a perspective view illustration of a vessel 102 with a modifiable stent 104 received within the vessel 102 and a coil stent 110 surrounding the vessel 102 and a portion of the modifiable stent 104. The stent system 100 can comprise a modifiable stent 104 and a coil stent 110. The modifiable stent 104, and the modifiable member(s) 106 and/or non-modifiable member(s) 108 can allow for engagement with a donor vessel 102 as discussed with reference to FIG. 1A, and can be utilized in a similar manner. The coil stent 110 can engage with the donor vessel 102. In at least one embodiment, the coil stent 110 can comprise a set of points 112 that allow for coupling of the coil stent 110 to a vessel. The set of points 112 can be coupled to the coupling member(s) 116 that form the coil stent 110. Additionally, the set of points 112 may be comprised of atraumatic point(s) 114A and/or traumatic point(s) 114B.

In at least one example, the coil stent 110 can be placed around or over a donor vessel 102 and the modifiable stent 104. In some examples, the modifiable stent 104 would be modified to engage the donor vessel 102 between the modifiable stent 104 and the coil stent 110, and the coil stent 110 can be utilized to engage with additional vessel(s).

Figure 1C:
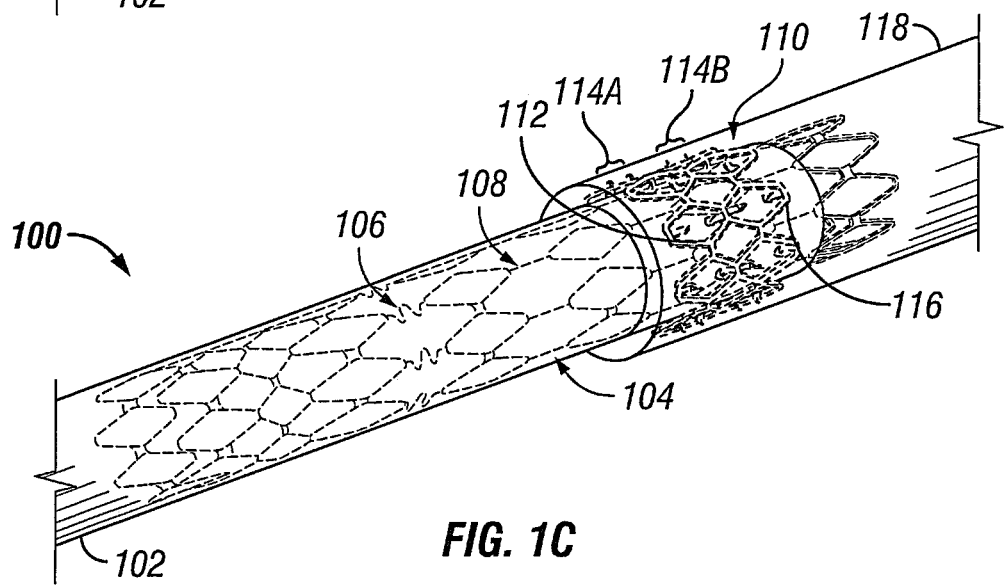
FIG. 1C is a perspective view illustration of a recipient vessel and a donor vessel being linked by a modifiable stent and a coil stent.

FIG. 1C is a perspective view illustration of a recipient vessel 118 and a donor vessel 102 being linked by a modifiable stent 104 and a coil stent 110. Further to the examples and embodiments illustrated in FIGS. 1A and 1, the recipient vessel 118 can receive the stent system 100 and the donor vessel 102. Because the modifiable stent 104 and the coil stent 110 engage the donor vessel 102 between them, the donor vessel 102 and stent system 100 can be placed within a recipient vessel 118. In some examples, after the recipient vessel 118 is engaged with the coil stent 110 of the stent system 100, the modifiable stent 104 may be further modified via the modifiable member(s) 106 and/or non-modifiable member(s) 108, allowing the stent system 100 to engage the vessels 102/118 to avoid movement after placement. The recipient vessel 118 can also be engaged by the set of points 112 of the coil stent 110. The atraumatic points 114A and/or the traumatic points 114B may be utilized for different flow rates or conditions of the vessels 102/118.

Figure 2A:
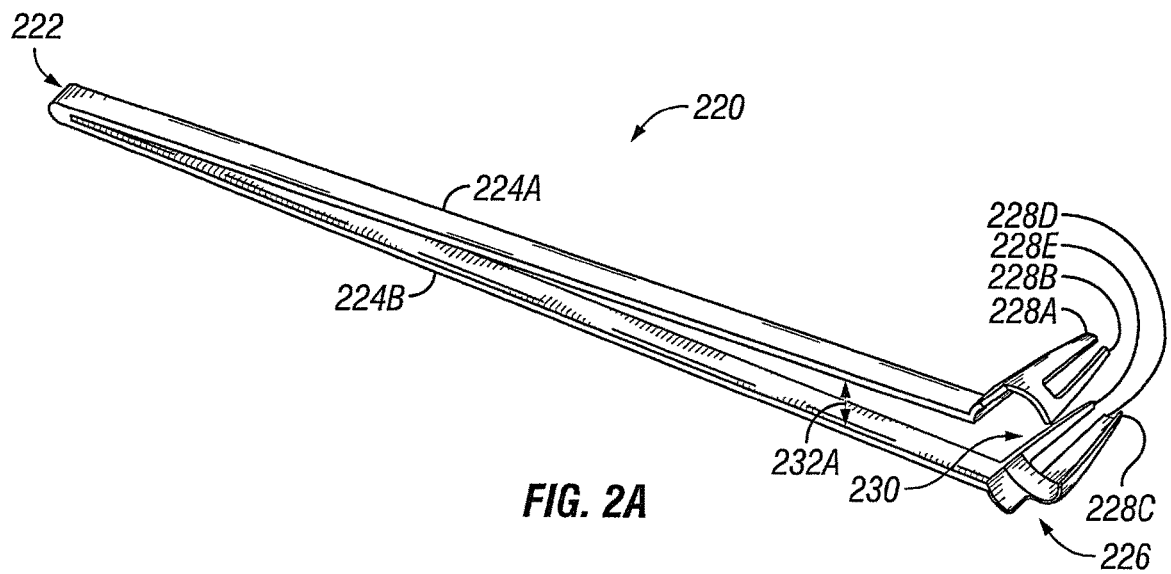
FIG. 2A is a perspective view illustration of a compression tool.

FIG. 2A is a perspective view illustration of a compression tool 220. The compression tool 220 can be utilized to compress one or both of the stents and/or coverings of the stents described in the present disclosure. The compression tool 220 has a first end or engagement section 226 that is opposite and distal from an inflection point 222. The inflection point 222 allows for the spring and/or resistive force that allows the compression tool 220 to remain in an open state 232A when not compressed by a user or external force (not illustrated).

The engagement section 226 and the inflection point 222, in at least one embodiment, can be connected by arms 224A and/or 224B. The arms 224A/224B, in at least one example, may be of a length that allows for a reasonable force to be applied by a user to compress and/or close the engagement zone 226. The engagement zone 226 can have an internal void 230 that is defined by a set of engagement arms 228A, 228B, 228C, 228D, 228E, and/or 228F (collectively a set of engagement arms 228). The set of engagement arms 228 can have lengths that allow for engagement with various portions of one or both of the stents described in the present disclosure.

In at least one example, the set of engagement arms 228 are elongated structures that are generally perpendicular to the arms 224A/224B. In some examples, the set of engagement arms 228 can be downwardly sloped to allow for additional engagement with one or more stents (not illustrated). In yet other examples, the set of engagement arms 228 may be upwardly sloped to allow for engagement with one or more stents with external protrusions.

In some examples, the compression tool 220 may be called a tweezer tool because of its similarity in operation to a tweezer. In a similar operation, a user can apply a force to the arms to cause a closing action to occur. When a closing action occurs, the arms move closer together from the starting or open state 232A. Upon releasing or reducing the force, the arms will return to the starting or open state 232A. In at least one example, the compression tool 220 may also include a locking mechanism between the arms that allows it to be locked in an open state 2323A or a closed state.

Figure 2B:
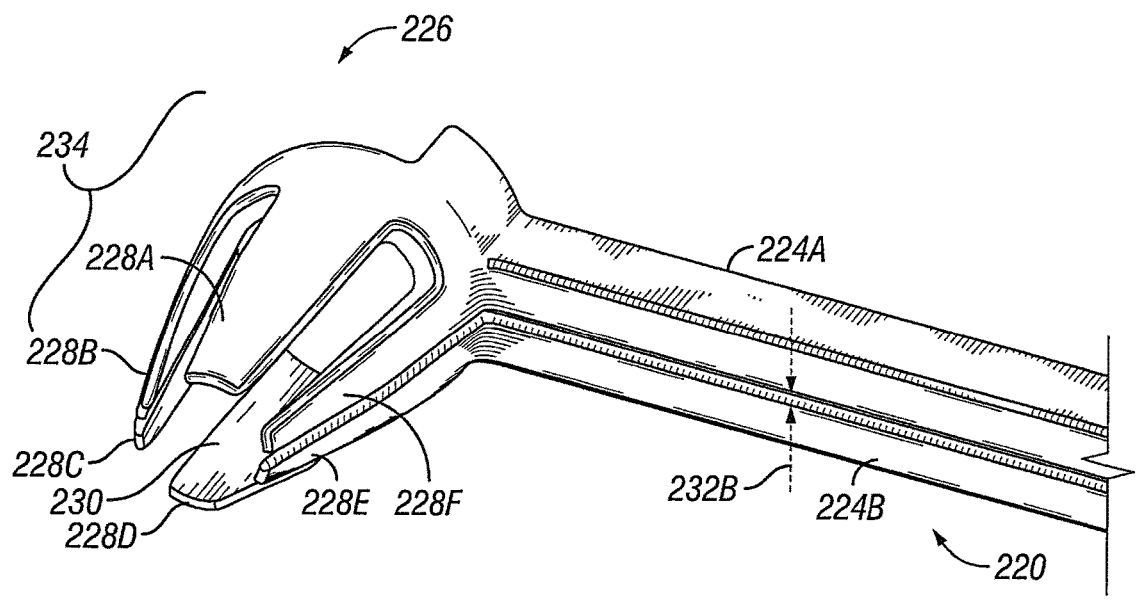
FIG. 2B is a perspective view illustration of an engagement section of a compression tool.

FIG. 2B is a perspective view illustration of an engagement section of a compression tool 220. The compression tool 220 can be utilized to compress one or both of the stents and/or coverings of the stents described in the present disclosure. The compression tool 220 has a first end or engagement section 226 that is opposite and distal from an inflection point. In at least one embedment, the inflection point allows for the spring and/or resistive force that allows the compression tool 220 to return to an open state after being compressed by a user or external force to a closed state 2323B. A closed state 232B can be when the arms 224A and/or 224B are touching or within a designed distance from one another. In at least one embodiment, when in a closed state the arms 224A and 224B are within less than one inch from one another, meaning an open state (shown as 232A in FIG. 2A) is when the arms 224A and 224B are more than one inch from one another.

The engagement section 226, in at least one embodiment, can be connected by arms 224A and/or 224B. The arms 224A/224B, in at least one example, may be of a length that allows for a reasonable force to be applied by a user to compress and/or close the engagement zone 226. The engagement zone 226, can have an internal void 230 that is defined by a set of engagement arms 228A, 228B, 228C, 228D, 228E, and/or 228F (collectively a set of engagement arms 228). The set of engagement arms 228 can have lengths that allow for engagement with various portions of one or both of the stents described in the present disclosure.

In at least one example, the set of engagement arms 228 are elongated structures that are generally perpendicular to the arms 224A/224B. In some examples, the set of engagement arms 228 can be downwardly sloped to allow for additional engagement with one or more stents (not illustrated). The downwardly sloped set of engagement arms 228 may allow for the engagement zone 226 to have a tapered end 234. In yet other examples, the set of engagement arms 228 may be upwardly sloped to allow for engagement with one or more stents with external protrusions, in this example, there may be a tapered end 234 that tapers upwardly from the internal void 230. In at least one example, the flexibility of the arms 224A/224B and/or engagement arms 228 can be flexible in nature to allow for a compressive force to be applied to said arms that is significant enough to compress the stents but not overcome the design and/or construction of the stent itself. In other words, a compression force can be applied by the arms 224A/224B and/or engagement arms 228 in such a way that they will not change the shape or design of the stent(s) in their various states.

In some examples, the compression tool 220 may be called a tweezer tool because of its similarity in operation to a tweezer. In a similar operation, a user can apply a force to the arms to cause a closing action to occur. When a closing action occurs, the arms move closer together from the starting or open state 232A. Upon releasing or reducing the force, the arms will return to the starting or open state 232A.

Figure 3A:
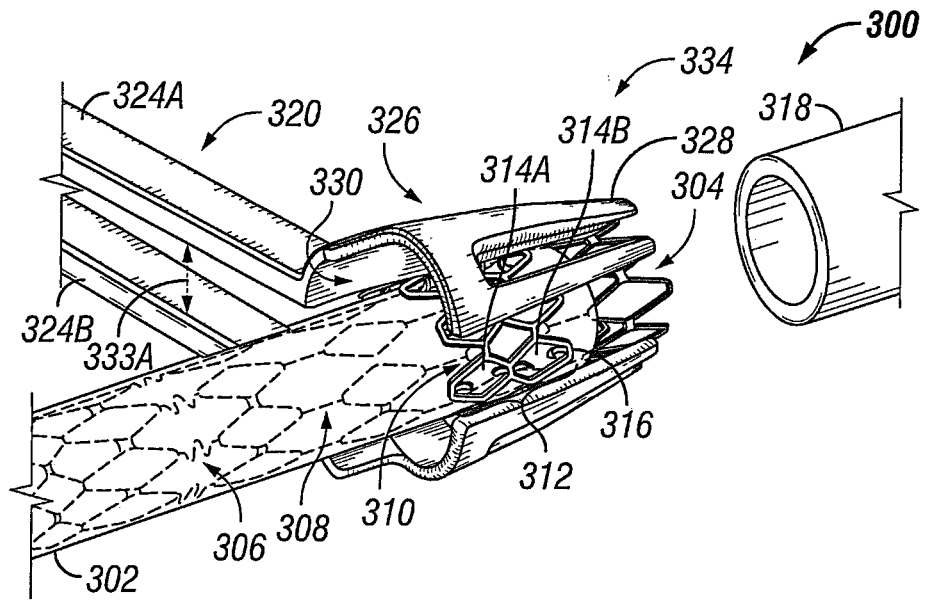
FIG. 3A is a perspective view illustration of a stent delivery system having a recipient vessel, a donor vessel, a modifiable stent, a coil stent, and a compression tool in an open state.

FIG. 3A is a perspective view illustration of a stent delivery system 300 having a recipient vessel 318, a donor vessel 302, a modifiable stent 304, a coil stent 310, and a compression tool 320 in an open state 332A. The stent delivery system 300, in at least one example, provides a user (a medical professional) with the ability to compress one or more stents, such as but not limited to the modifiable stent 304 and/or coil stent 310, for easy of entry and/or placement within one or more vessels such as, but not limited to the donor vessel 302 and/or recipient vessel 318. In some examples, the compression tool 320 engages with one or both stents (illustrated as modifiable stent 304 and/or coil stent 310), to allow for the easy of insertion into one or more vessels (illustrated as recipient vessel 318 and donor vessel 302).

In at least one embodiment, the modifiable stent 304 is formed with a combination of modifiable member(s) 306 and non-modifiable member(s) 308. While in some examples, the modifiable stent 304 may be comprised only modifiable member(s) 306 or non-modifiable member(s)

308. Additionally, in at least one example, the modifiable stent 304 may also have additional traumatic or atraumatic anchor points (not illustrated) that allow for the modifiable stent 304 to be anchored to a specific location or position within the vessel(s) or lumen.

Similarly, the coil stent 310, in at least one embodiment, is formed with coupling member(s) 316, and has a point set 312. In some examples, the coil stent 310 may also include modifiable member(s) (not illustrated) that would allow for the coil stent 310 to be modified in a similar manner as the modifiable stent 304. While in other examples, the coil stent 310 may be formed from only modifiable member(s). The point set 312 of the coil stent 310 may include atraumatic point(s) 314A and/or traumatic point(s) 314B, individually or in combination, to allow for engagement with one or more vessels, such as but not limited to the recipient vessel 318 and/or donor vessel 302.

In at least one embodiment, the modifiable stent 304 is co-axially located or concentric to the coil stent 310. For clarity, in some examples, there can be a covering or sheath between the stents and/or vessels. The modifiable stent 304, in at least one example, is housed within the inner diameter of the coil stent 310. The concentric nature of the stent placements allows for the modifiable stent 304 to expand outwardly, to allow for proper fluid passage through the modifiable stent 304, while the coil stent 310 can engage with the vessels (illustrated as recipient vessel 318 and/or donor vessel 302) to prevent the movement of the modifiable stent 304 and/or the coil stent 310. In some examples, the lack of movement of the stents also allows for quicker healing when their vessels are placed in close proximity.

The engagement section 326, in at least one embodiment, can be connected by arms 324A and/or 324B. The arms 324A/324B, in at least one example, may be of a length that allows for a reasonable force to be applied by a user to compress and/or close the engagement zone 326. The engagement zone 326, can have an internal void 330 that is defined by a set of engagement arms 328. The set of engagement arms 328 can have lengths that allow for engagement with various portions of one or both of the stents described in the present disclosure.

In at least one example, the set of engagement arms 328 are elongated structures that are generally perpendicular to the arms 324A/324B. In some examples, the set of engagement arms 328 can be downwardly sloped to allow for additional engagement with one or more stents (not illustrated). In yet other examples, the set of engagement arms 328 may be upwardly sloped to allow for engagement with one or more stents with external protrusions. In at least one embodiment, the engagement arm(s) 328 and the tapered end 334 allow for a user to more easily engage and/or place the stents within a vessel, such as but not limited to the recipient vessel 318. The tapered end 334 can allow the vessel (represented by recipient vessel 318) to be slid, or eased over the stent(s) without the vessel(s) engaging with the stents.

In some examples, the compression tool 320 may be called a tweezer tool because of its similarity in operation to a tweezer. In a similar operation, a user can apply a force to the arms to cause a closing action to occur. When a closing action occurs, the arms move closer together from the starting or open state 332A. Upon releasing or reducing the force, the arms will return to the starting or open state 332A.

Figure 3B:
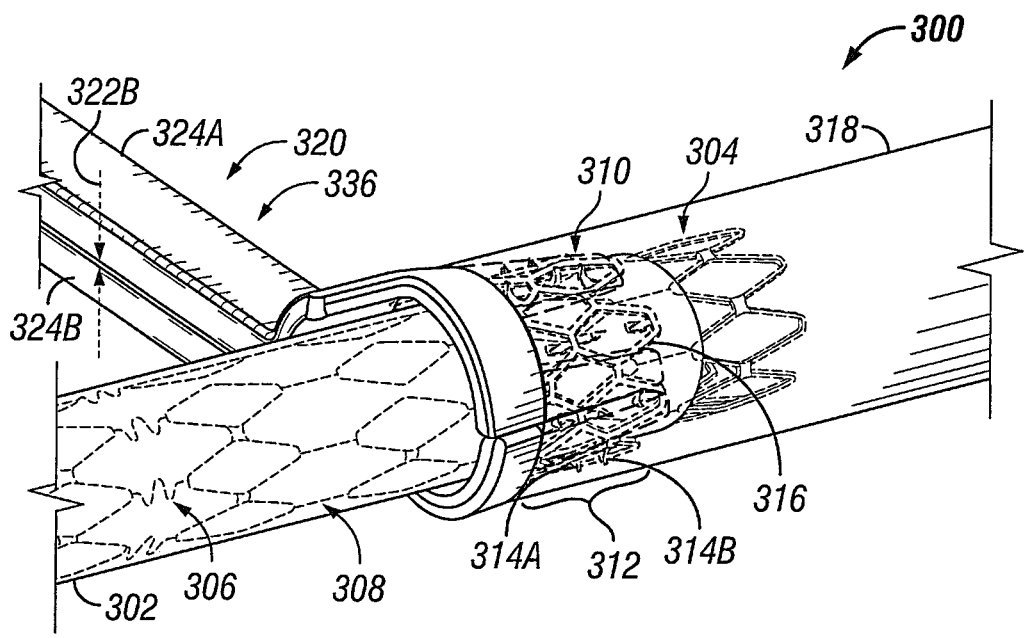
FIG. 3B is a perspective view illustration of a stent delivery system having a recipient vessel, a donor vessel, a modifiable stent, a coil stent, and a compression tool in an open state.

FIG. 3B is a perspective view illustration of a stent delivery system 300 having a recipient vessel 318, a donor vessel 302, a modifiable stent 304, a coil stent 310, and a compression tool 320 in an open state 332A. The stent delivery system 300, in at least one example, provides a user (a medical professional) with the ability to compress one or more stents, such as but not limited to the modifiable stent 304 and/or coil stent 310, for easy of entry and/or placement within one or more vessels such as, but not limited to the donor vessel 302 and/or recipient vessel 318. In some examples, the compression tool 320 engages with one or both of the stents (illustrated as modifiable stent 304 and/or coil stent 310), to allow for the easy of insertion into one or more vessels (illustrated as recipient vessel 318 and donor vessel 302).

In at least one embodiment, the modifiable stent 304 is formed with a combination of modifiable member(s) 306 and non-modifiable member(s) 308. While in some examples, the modifiable stent 304 may be comprised only modifiable member(s) 306 or non-modifiable member(s) 308. Additionally, in at least one example, the modifiable stent 304 may also have additional traumatic or atraumatic anchor points (not illustrated) that allow for the modifiable stent 304 to be anchored to a specific location or position within the vessel(s) or lumen.

Similarly, the coil stent 310, in at least one embodiment, is formed with coupling member(s) 316, and has a point set 312. In some examples, the coil stent 310 may also include modifiable member(s) (not illustrated) that would allow for the coil stent 310 to be modified in a similar manner as the modifiable stent 304. While in other examples, the coil stent 310 may be formed from only modifiable member(s). The point set 312 of the coil stent 310 may include atraumatic point(s) 314A and/or traumatic point(s) 314B, individually or in combination, to allow for engagement with one or more vessels, such as but not limited to the recipient vessel 318 and/or donor vessel 302.

In at least one embodiment, the modifiable stent 304 is co-axially located or concentric to the coil stent 310. For clarity, in some examples, there can be a covering or sheath between the stents and/or vessels. The modifiable stent 304, in at least one example, is housed within the inner diameter of the coil stent 310. The concentric nature of the stent placements allows for the modifiable stent 304 to expand outwardly, to allow for proper fluid passage through the modifiable stent 304, while the coil stent 310 can engage with the vessels (illustrated as recipient vessel 318 and/or donor vessel 302) to prevent the movement of the modifiable stent 304 and/or the coil stent 310. In some examples, the lack of movement of the stents also allows for quicker healing when their vessels are placed in close proximity.

The engagement section 326, in at least one embodiment, can be connected by arms 324A and/or 324B. The arms 324A/324B, in at least one example, may be of a length that allows for a reasonable force to be applied by a user to compress and/or close the engagement zone 326. The engagement zone 326, can have an internal void 330 that is defined by a set of engagement arms 328. The set of engagement arms 328 can have lengths that allow for engagement with various portions of one or both of the stents described in the present disclosure.

In at least one example, the set of engagement arms 328 are elongated structures that are generally perpendicular to the arms 324A/324B. In some examples, the set of engagement arms 328 can be downwardly sloped to allow for additional engagement with one or more stents (not illustrated). In yet other examples, the set of engagement arms 328 may be upwardly sloped to allow for engagement with one or more stents with external protrusions. In at least one embodiment, the engagement arm(s) 328 and the tapered end 334 allow for a user to more easily engage and/or place the stents within a vessel, such as but not limited to the recipient vessel 318. The tapered end 334 can allow the vessel (represented by recipient vessel 318) to be slid or eased over the stent(s) without the vessel(s) engaging with the stents.

In some examples, the compression tool 320 may be called a tweezer tool because of its similarity in operation to a tweezer. In a similar operation, a user can apply a force 336 to the arms to cause a closing action 332B to occur. When a closing action 332B occurs, the arms move closer together from the starting or open state illustrated in FIG. 3A. Upon releasing or reducing the force, the arms will return to the starting or open state.

Figure 4A:
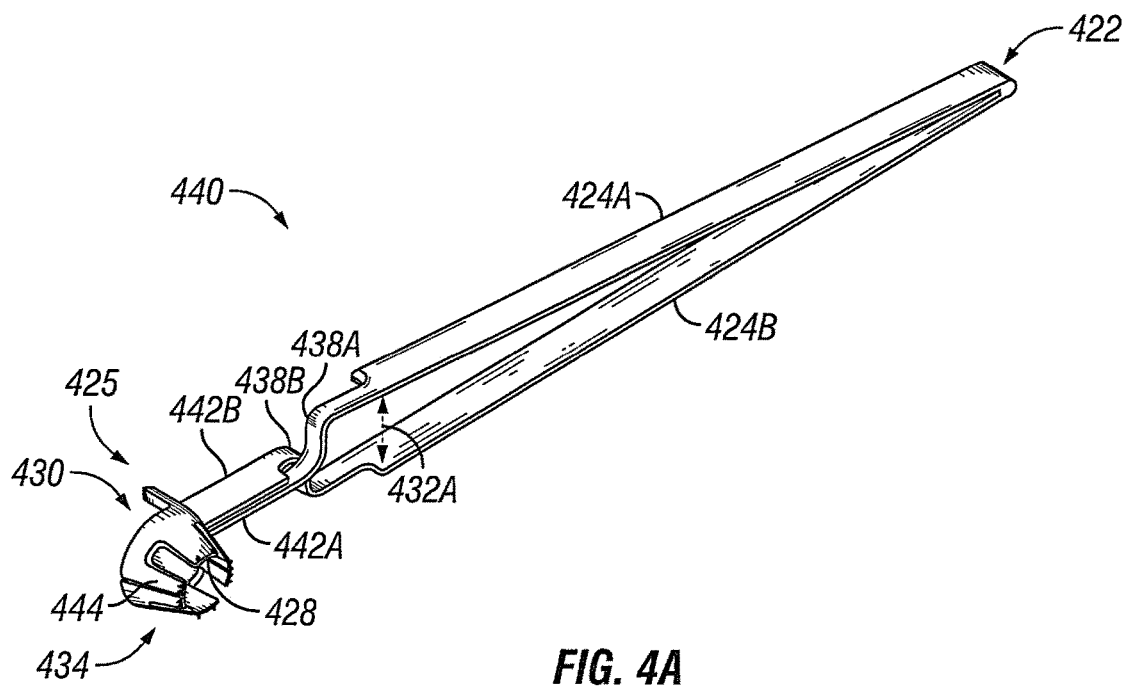
FIG. 4A is a perspective view illustration of an expansion tool.

FIG. 4A is a perspective view illustration of an expansion tool 440. The expansion tool 440 may be utilized to expand a vessel to allow for placement of the stents of the present disclosure. The expansion tool 440 has a first end or engagement section 426 that is opposite and distal form an inflection point 422. The inflection point 422 allows for the spring and/or resistive force that allows the expansion tool 440 to remain in a neutral state 432A when not compressed by a user or external force (not illustrated).

The engagement section 426 and the inflection point 422, in at least one embodiment, can be connected by arms 424A and/or 424B. The arms 424A/424B, in at least one example, may be of a length that allows for a reasonable force to be applied by a user to compress the arms 424A/424B and/or open the engagement zone 426. Transfer arms 438A and/or 438B can allow a for the transfer of the compression or reasonable force applied by a user to extension arms 442A and/or 442B. The transfer arms 438A/438B may be of a length that allows for the closing of the engagement zone 426 when the expansion tool 440 is in a neutral state 432A and are generally perpendicular to the arms 424A/424B and/or extension arms 442A/442B. In some examples, engagement zone 426 may also be referenced as an engagement section 426. The extension arms 442A/442B can act as an extension of the arms 424A/424B but are in opposite planes in order to allow for the expansion of the expansion tool 440. For example, arm 424A corresponds to the extension arm 442B, and arm 424B corresponds to extension arm 442A. This cross over is possible because of the transfer arms 438A/438B.

In at least one examples, the engagement zone 426, can have an internal void 430 that is defined by a set of engagement arms 428. The set of engagement arms 428 can have lengths that allow for engagement with various portions of one or both of the stents and/or a vessel described in the present disclosure. The set of engagement arms 428 can be elongated structures that are generally perpendicular to the arms 424A/424B. In some examples, the set of engagement arms 428 can be downwardly sloped to allow for additional engagement with vessel. In yet other examples, the set of engagement arms 428 may be upwardly sloped to allow for engagement with a vessel via external protrusions. In at least one embodiment, the set of engagement arms 428 has a set of engagement points 444 that can be traumatic or atraumatic to allow for further engagement with a vessel.

In some examples, the expansion tool 440 may be called an expander tool because of its similarity in operation to an expander used in orthodontics to push two points away from one another. In a similar operation, a user can apply a force to the arms to cause an opening action to occur. When an opening action occurs, the arms move closer together from the starting or open state 432A allowing the engagement zone 426 to open. Upon releasing or reducing the force, the arms will return to the starting or open state 432A and the engagement zone 426 will return to its closed state.

Figure 4B:
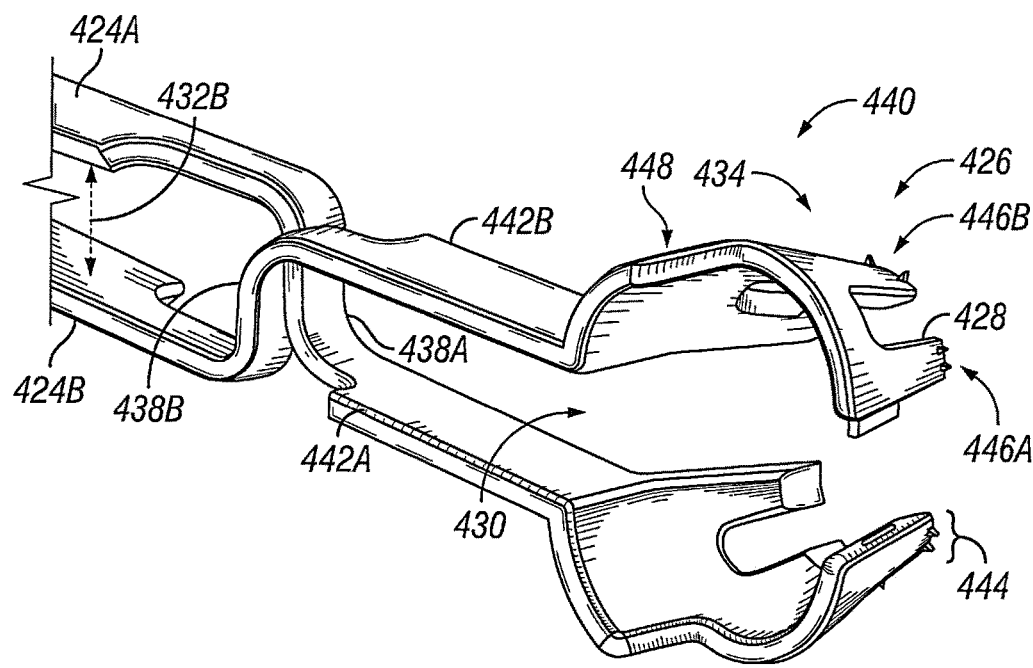
FIG. 4B is a perspective view illustration of an engagement section of an expansion tool.

FIG. 4B is a perspective view illustration of an engagement section 426 of an expansion tool 440. The expansion tool 440 may be utilized to expand a vessel to allow for placement of the stents of the present disclosure. The expansion tool 440 has a first end or engagement section 426 that is opposite and distal form an inflection point (illustrated in FIG. 4A). The inflection point allows for the spring and/or resistive force that allows the expansion tool 440 to remain in a neutral state when not compressed by a user or external force (not illustrated) and allows for the expanded state 432B when a user or external force (not illustrated) is applied to the expansion tool 440.

The engagement section 426, in at least one embodiment, may be connected by arms 424A and/or 424B. The arms 424A/424B, in at least one example, may be of a length that allows for a reasonable force to be applied by a user to compress the arms 424A/424B and/or open the engagement zone 426. Transfer arms 438A and/or 438B can allow a for the transfer of the compression or reasonable force applied by a user to extension arms 442A and/or 442B. The transfer arms 438A/438B may be of a length that allows for the closing of the engagement zone 426 when the expansion tool 440 is in a neutral state 432A and are generally perpendicular to the longitudinal direction (from the inflection point to the engagement zone 426) of the arms 424A/424B and/or extension arms 442A/442B. In some examples, engagement zone 426 may also be referenced as an engagement section 426. The extension arms 442A/442B can act as an extension of the arms 424A/424B but are in opposite planes in order to allow for the expansion of the expansion tool 440. For example, arm 424A corresponds to the extension arm 442B, and arm 424B corresponds to extension arm 442A. This cross over is possible because of the transfer arms 438A/438B.

In at least one examples, the engagement zone 426, can have an internal void 430 that is defined by a set of engagement arms 428. The set of engagement arms 428 can have lengths that allow for engagement with various portions of one or both of the stents and/or a vessel described in the present disclosure. The set of engagement arms 428 can be elongated structures that are generally perpendicular to the arms 424A/424B. In some examples, the set of engagement arms 428 can be downwardly sloped to allow for additional engagement with vessel. In yet other examples, the set of engagement arms 428 may be upwardly sloped to allow for engagement with a vessel via external protrusions. In at least one embodiment, the set of engagement arms 428 has a set of engagement points 444 that can be traumatic or atraumatic to allow for further engagement with a vessel. The engagement points 444 may be atraumatic points 446A or traumatic points 446B. For simplicity, atraumatic points 446A are those designed to not pierce or damage a lumen of a vessel, or other body part, while traumatic points 446B may or may not pierce or otherwise damage, non-critically, a lumen of a vessel or other body part. The ability of the expansion tool 440 to engage with lumens of vessels or other body party may increase with the introduction of a flex point 448 that allows a portion of the engagement zone 426 to be flexible in relation to a second portion. For example, the second portion of the engagement zone 426 may be coupled to the extension arm(s) 442A/442B while the portion that is opposite the flex point 448 and second portion is free to move and can be bias to expand outwardly to allow for better engagement with a vessel, lumen, or body part.

In some examples, the expansion tool 440 may be called an expander tool because of its similarity in operation to an expander used in orthodontics to push two points away from one another. In a similar operation, a user can apply a force to the arms to cause an opening action to occur. When an opening action occurs, the arms move closer together from the starting or open state allowing the engagement zone 426 to open when the expansion tool is in an expanded state 432B. Upon releasing or reducing the force keeping the expansion tool in an expanded state 432B, the arms will return to the starting or open state and the engagement zone 426 will return to its closed state.

Figure 5A:
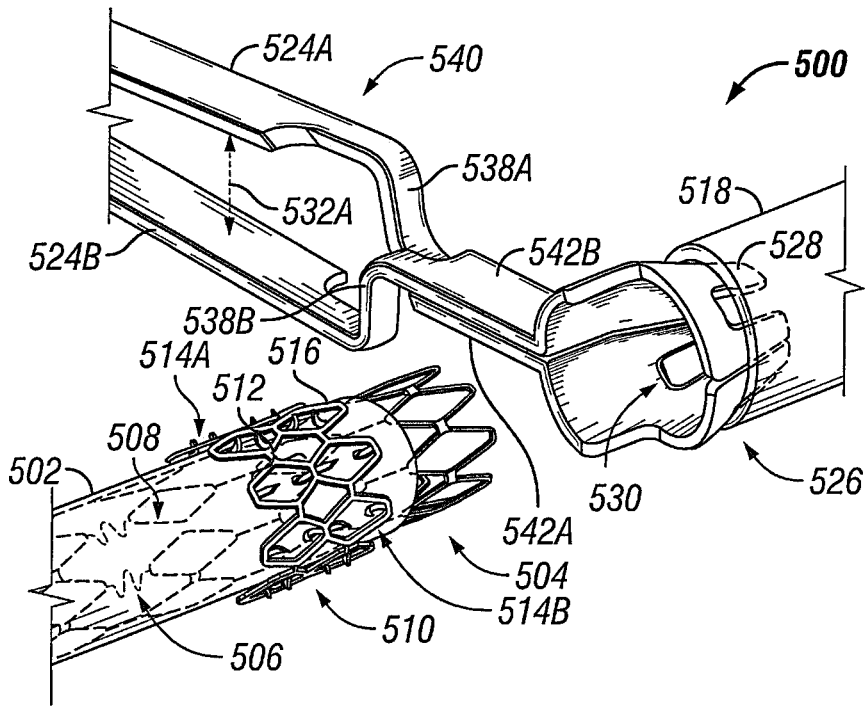
FIG. 5A is a perspective view illustration of a stent delivery system engaging with a receiving vessel, donor vessel, through a modifiable stent, a coil stent, and an expansion tool.

FIG. 5A is a perspective view illustration of stent delivery system 500 engaging with a receiving vessel, donor vessel, through a modifiable stent, a coil stent, and an expansion tool. The stent delivery system 500, in at least one example, allows a user (medical professional) with the ability to expand a vessel such as, but not limited to a recipient vessel 518 and/or donor vessel 502, to allow the insertion of one or more stents, such as but not limited to a modifiable stent 504 and/or a coil stent 510. In some examples, the expansion tool 540 engages with the inner diameter or radius of a vessel (sometimes called the lumen) to expand the vessel to a size large engage to allow placement of one or more stents. As illustrated in FIG. 5A, the expansion tool 540 can be placed within the lumen of a vessel (illustrated as recipient vessel 518.

These stents can then engage with the vessel(s) to allow for proper placement. In at least one embodiment, the modifiable stent 504 is formed with a combination of modifiable member(s) 506 and non-modifiable member(s) 508. While in some examples, the modifiable stent 504 may be comprised only modifiable member(s) 506 or non-modifiable member(s) 508. Additionally, in at least one example, the modifiable stent 504 may also have additional traumatic or atraumatic anchor points (not illustrated) that allow for the modifiable stent 504 to be anchored to a specific location or position within the vessel(s) or lumen.

Similarly, the coil stent 510, in at least one embodiment, is formed with coupling member(s) 516, and has a point set 512. In some examples, the coil stent 510 may also include modifiable member(s) (not illustrated) that would allow for the coil stent 510 to be modified in a similar manner as the modifiable stent 504. While in other examples, the coil stent 510 may be formed from only modifiable member(s). The point set 512 of the coil stent 510 may include atraumatic point(s) 514A and/or traumatic point(s) 514B, individually or in combination, to allow for engagement with one or more vessels, such as but not limited to the recipient vessel 518 and/or donor vessel 502.

In at least one embodiment, the modifiable stent 504 is co-axially located or concentric to the coil stent 510. For clarity, in some examples, there can be a covering or sheath between the stents and/or vessels. The modifiable stent 504, in at least one example, is housed within the inner diameter of the coil stent 510. The concentric nature of the stent placements allows for the modifiable stent 504 to expand outwardly, to allow for proper fluid passage through the modifiable stent 504, while the coil stent 510 can engage with the vessels (illustrated as recipient vessel 518 and/or donor vessel 502) to prevent the movement of the modifiable stent 504 and/or the coil stent 510. In some examples, the lack of movement of the stents also allows for quicker healing when their vessels are placed in close proximity.

In at least one examples, the engagement zone 526, can have an internal void 530 that is defined by a set of engagement arms 528. The set of engagement arms 528 can have lengths that allow for engagement with various portions of one or both of the stents and/or a vessel described in the present disclosure. The set of engagement arms 528 can be elongated structures that are generally perpendicular to the arms 524A/524B. In some examples, the set of engagement arms 528 can be downwardly sloped to allow for additional engagement with vessel. In yet other examples, the set of engagement arms 528 may be upwardly sloped to allow for engagement with a vessel via external protrusions. In at least one embodiment, the set of engagement arms 528 has a set of engagement points 544 that can be traumatic or atraumatic to allow for further engagement with a vessel.

In some examples, the expansion tool 540 may be called an expander tool because of its similarity in operation to an expander used in orthodontics to push two points away from one another. In a similar operation, a user can apply a force to the arms to cause an opening action to occur. When an opening action occurs, the arms move closer together from the starting or open state 532A allowing the engagement zone 526 to open. Upon releasing or reducing the force, the arms will return to the starting or open state 532A and the engagement zone 526 will return to its closed state.

Figure 5B:
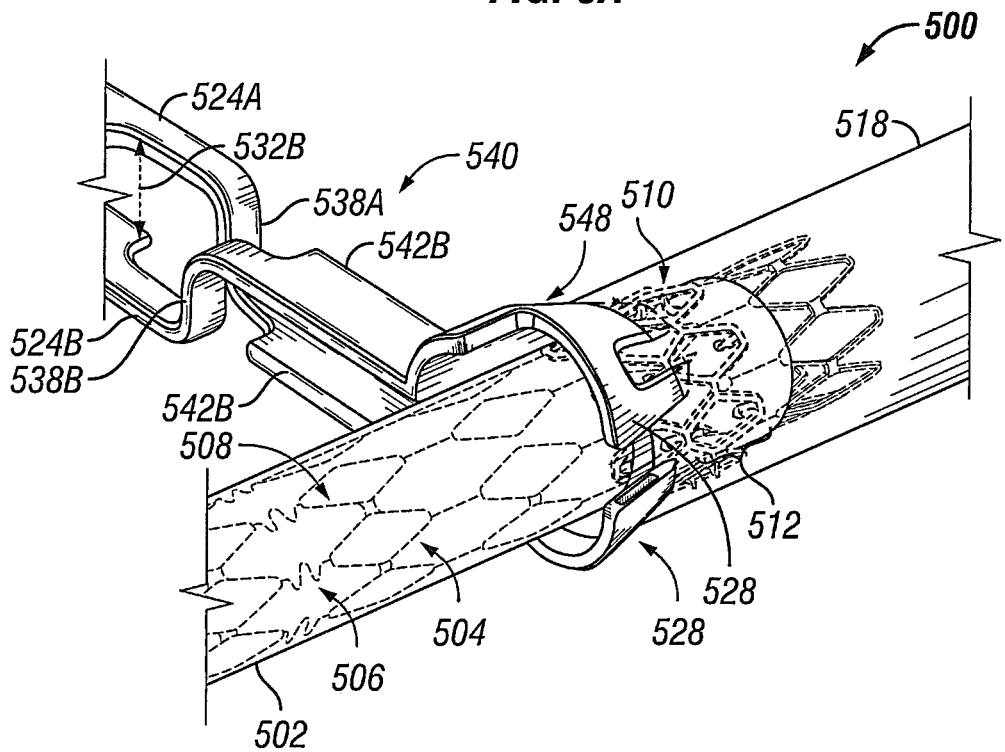
FIG. 5B is a perspective view illustration of a stent delivery system engaging with a receiving vessel, donor vessel, through a modifiable stent, a coil stent, and an expansion tool in an expanded state.

FIG. 5B is a perspective view illustration of stent delivery system 500 engaging with a receiving vessel, donor vessel, through a modifiable stent, a coil stent, and an expansion tool in an expanded state. The stent delivery system 500, in at least one example, allows a user (medical professional) with the ability to expand a vessel such as, but not limited to a recipient vessel 518 and/or donor vessel 502, to allow the insertion of one or more stents, such as but not limited to a modifiable stent 504 and/or a coil stent 510. In some examples, the expansion tool 540 engages with the inner diameter or radius of a vessel (sometimes called the lumen) to expand the vessel to a size large engage to allow placement of one or more stents. As illustrated in FIG. 5A, the expansion tool 540 can be placed within the lumen of a vessel (illustrated as recipient vessel 518.

These stents can then engage with the vessel(s) to allow for proper placement. In at least one embodiment, the modifiable stent 504 is formed with a combination of modifiable member(s) 506 and non-modifiable member(s) 508. While in some examples, the modifiable stent 504 may be comprised only modifiable member(s) 506 or non-modifiable member(s) 508. Additionally, in at least one example, the modifiable stent 504 may also have additional traumatic or atraumatic anchor points (not illustrated) that allow for the modifiable stent 504 to be anchored to a specific location or position within the vessel(s) or lumen.

Similarly, the coil stent 510, in at least one embodiment, is formed with coupling member(s) 516, and has a point set 512. In some examples, the coil stent 510 may also include modifiable member(s) (not illustrated) that would allow for the coil stent 510 to be modified in a similar manner as the modifiable stent 504. While in other examples, the coil stent 510 may be formed from only modifiable member(s). The point set 512 of the coil stent 510 may include atraumatic point(s) 514A and/or traumatic point(s) 514B, individually or in combination, to allow for engagement with one or more vessels, such as but not limited to the recipient vessel 518 and/or donor vessel 502.

In at least one embodiment, the modifiable stent 504 is co-axially located or concentric to the coil stent 510. For clarity, in some examples, there can be a covering or sheath between the stents and/or vessels. The modifiable stent 504, in at least one example, is housed within the inner diameter of the coil stent 510. The concentric nature of the stent placements allows for the modifiable stent 504 to expand outwardly, to allow for proper fluid passage through the modifiable stent 504, while the coil stent 510 can engage with the vessels (illustrated as recipient vessel 518 and/or donor vessel 502) to prevent the movement of the modifiable stent 504 and/or the coil stent 510. In some examples, the lack of movement of the stents also allows for quicker healing when there vessels are placed in close proximity.

In at least one examples, the engagement zone 526, can have an internal void 530 that is defined by a set of engagement arms 528. The set of engagement arms 528 can have lengths that allow for engagement with various portions of one or both of the stents and/or a vessel described in the present disclosure. The set of engagement arms 528 can be elongated structures that are generally perpendicular to the arms 524A/524B. In some examples, the set of engagement arms 528 can be downwardly sloped to allow for additional engagement with vessel. In yet other examples, the set of engagement arms 528 may be upwardly sloped to allow for engagement with a vessel via external protrusions. In at least one embodiment, the set of engagement arms 528 has a set of engagement points 544 that can be traumatic or atraumatic to allow for further engagement with a vessel. The engagement points 544 may be atraumatic points 546A or traumatic points 546B. For simplicity, atraumatic points 546A are those designed to not pierce or damage a lumen of a vessel, or other body part, while traumatic points 546B may or may not pierce or otherwise damage, non-critically, a lumen of a vessel or other body part. The ability of the expansion tool 540 to engage with lumens of vessels or other body party may increase with the introduction of a flex point 548 that allows a portion of the engagement zone 526 to be flexible in relation to a second portion. For example, the second portion of the engagement zone 526 may be coupled to the extension arm(s) 542A/542B while the portion that is opposite the flex point 548 and second portion is free to move and can be bias to expand outwardly to allow for better engagement with a vessel, lumen, or body part.

In some examples, the expansion tool 540 may be called an expander tool because of its similarity in operation to an expander used in orthodontics to push two points away from one another. In a similar operation, a user can apply a force to the arms to cause an opening action to occur. When an opening action occurs, the arms move closer together from the starting or open state allowing the engagement zone 526 to open when the expansion tool is in an expanded state 4532B. Upon releasing or reducing the force keeping the expansion tool in an expanded state 532B, the arms will return to the starting or open state and the engagement zone 526 will return to its closed state.

Figure 6A:
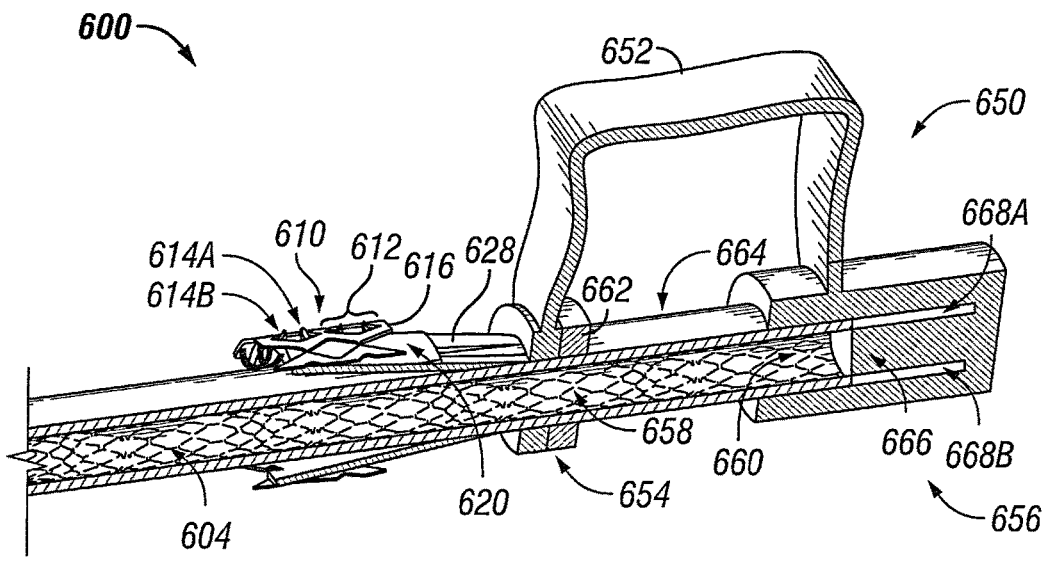
FIG. 6A is a perspective cutaway view illustration of a stent delivery system having a combination tool and compression tool, engaging with a coil stent and a modifiable stent.

FIG. 6A is a perspective cutaway view illustration of stent delivery system 600 having a combination tool, and compression tool, engaging with a coil stent, and a modifiable stent. The combination tool 650 allows for delivery of one or more stents to one or more vessels with relative ease and simplicity. Traditionally, stent placement surgery can require many tedious hours and detailed surgery that can be risky to patients. The combination tool 650 allows a user or medical professional to insert one or more stents into a vessel and allows for a compression tool 620 to be included during the insert for quick use during a surgical procedure. In at least one example, the compression tool 620 can be utilized to insert the one or more stents into a second vessel after the combination tool 650 is utilized to insert the stent delivery system 600 into a first vessel.

The combination tool 650 can include a handle 652 for ease of gripping and controlling the insertion and/or placement of one or more stents utilizing the combination tool 650. The handle of the combination tool 650, can be connected to a first end 654, and a second end 656. In at least one example the first end 654 (in some examples, a distal end) may be distal from the second end 656 (in some examples, a proximal end). The second end 656 can be proximal to the user's control and/or hand during an operation, surgery, or procedure.

The first end 654, in at least one embodiment, can include a receiving aperture 658 that allows for one or more stents and/or stent covers or sheaths to pass through from the first end 654 to the second end 656 of the combination tool 650. In some examples the receiving aperture 658 can interact and/or engage with a container ring 662. The container ring 662 can be a ring or conduit that can be utilized to support one or more stents and/or stent covers or sheaths as they pass through and/or contained within the first end 654 of the combination tool 650. In some examples, the container ring 662 may have an elongated section that surrounds the one or more stents. In at least one example, a containment void 664 may be present between the first end 654 and the second end 656. In some examples, the containment void 664 may be defined by a layer of material to assist in containing the one or more stents.

The second end 656, in at least one embodiment, can include a receiving void 660 that allows for the storage and/or containment of one or more stents and/or covers or sheaths of the one or more stents. In at least one example, this allows for a modifiable stent 604 and/or coil stent 610 to be contained and prevented from expanding beyond the desired first state, or unmodified state. The second end 656 can define the receiving void 660 in a manner that allows it to prevent the expansion or modification of the one or more stents. In at least one example, the receiving void 660 is in communication with one or more receiving channels 668A and/or 668B. It would be understood that the receiving channels 668A/668B may be illustrated as two channels when viewed as a cross section view, but the two channels may be a single channel that is in a rounded or circular form. The receiving channels 668A/668B can surround a contact point 666 that allows for engagement and/or contact with the one or more stents and/or sheaths or covers during an insertion procedure.

The compression tool 620, in at least one embodiment, can allow for the compression of a modifiable stent 604 and/or expansion of a coil stent 610. In at least one example, the compression tool 620 can have a set of engagement arms 628 with lengths that allow for engagement with various portions of one or both of the stents described in the present disclosure. The set of engagement arms 628 are elongated structures, that may be downwardly or upwardly sloped to allow for additional engagement with one or more stents.

In at least one embodiment, the modifiable stent 604 is formed with a combination of modifiable member(s) and/or non-modifiable member(s). Additionally, in at least one example, the modifiable stent 604 may also have additional traumatic or atraumatic anchor points (not illustrated) that allow for the modifiable stent 604 to be anchored to a specific location or position within the vessel(s) or lumen. Similarly, the coil stent 610, in at least one embodiment, is formed with coupling member(s) 616, and has one or more point set(s) 612. In some examples, the coil stent 610 may also include modifiable member(s) (not illustrated) that would allow for the coil stent 610 to be modified in a similar manner as the modifiable stent 304. While in other examples, the coil stent 610 may be formed from only modifiable member(s). The point set 612 of the coil stent 610 may include atraumatic point(s) 614A and/or traumatic point(s) 614B, individually or in combination, to allow for engagement with one or more vessels.

In at least one embodiment, the modifiable stent 604 is co-axially located or concentric to the coil stent 610. For clarity, in some examples, there can be a covering or sheath between the stents and/or vessels. The modifiable stent 604, in at least one example, is housed within the inner diameter of the coil stent 610. The concentric nature of the stent placements allows for the modifiable stent 604 to expand outwardly, to allow for proper fluid passage through the modifiable stent 604, while the coil stent 610 can engage with the vessels to prevent the movement of the modifiable stent 604 and/or the coil stent 610. In some examples, the lack of movement of the stents also allows for quicker healing when there vessels are placed in close proximity.

Figure 6B:
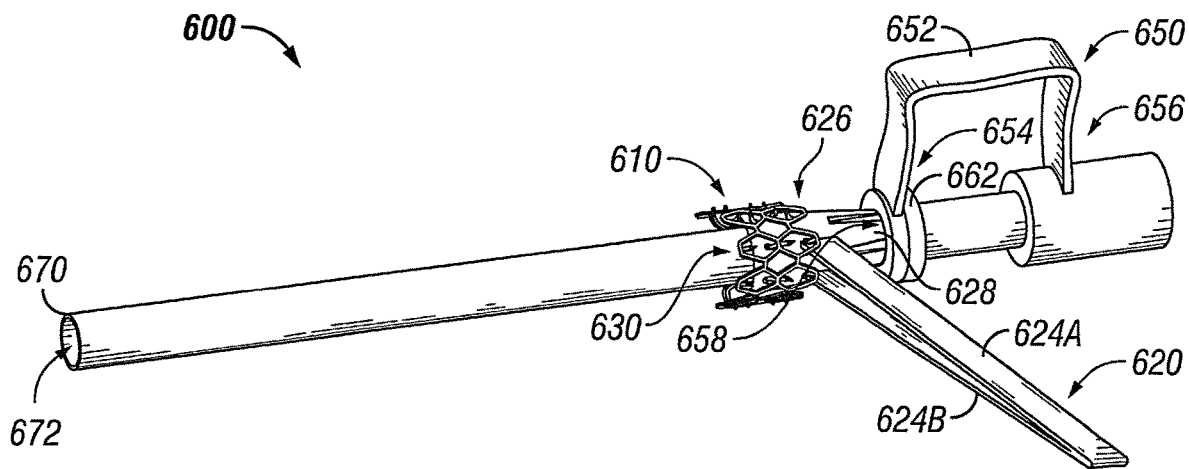
FIG. 6B is a perspective view illustration of a stent delivery system having a combination tool and compression tool, engaging with a coil stent and a modifiable stent.

FIG. 6B is a perspective view illustration of stent delivery system 600 having a combination tool, and compression tool, engaging with a coil stent, and a modifiable stent. The combination tool 650 allows for delivery of one or more stents to one or more vessels with relative ease and simplicity. Traditionally, stent placement surgery can require many tedious hours and detailed surgery that can be risky to patients. The combination tool 650 allows a user or medical professional to insert one or more stents into a vessel and allows for a compression tool 620 to be included during the insert for quick use during a surgical procedure. In at least one example, the compression tool 620 can be utilized to insert the one or more stents into a second vessel after the combination tool 650 is utilized to insert the stent delivery system 600 into a first vessel.

The combination tool 650 can include a handle 652 for ease of gripping and controlling the insertion and/or placement of one or more stents utilizing the combination tool 650. The handle of the combination tool 650, can be connected to a first end 654, and a second end 656. In at least one example the first end 654 (in some examples, a distal end) may be distal from the second end 656 (in some examples, a proximal end). The second end 656 can be proximal to the user's control and/or hand during an operation, surgery, or procedure.

The first end 654, in at least one embodiment, can interact and/or engage with a container ring 662. The container ring 662 can be a ring or conduit that can be utilized to support one or more stents and/or stent covers or sheaths as they pass through and/or contained within the first end 654 of the combination tool 650. In some examples, the container ring 662 may have an elongated section that surrounds the one or more stents.

The compression tool 620, in at least one embodiment, can allow for the compression of a modifiable stent (not illustrated) and/or expansion of a coil stent 610. The engagement section 626 of the compression tool, in at least one embodiment, can be connected by arms 624A and/or 624B. The arms 624A/624B, in at least one example, may be of a length that allows for a reasonable force to be applied by a user to compress and/or close the engagement zone 626. The engagement zone 626, can have an internal void 630 that is defined by a set of engagement arms 628. The set of engagement arms 628 can have lengths that allow for engagement with various portions of one or both of the stents described in the present disclosure.

In at least one example, the set of engagement arms 628 are elongated structures that are generally perpendicular to the arms 624A/624B. The set of engagement arms 628 are elongated structures, that may be downwardly or upwardly sloped to allow for additional engagement with one or more stents. In some examples, the set of engagement arms 628 can be downwardly sloped to allow for additional engagement with one or more stents (not illustrated). In yet other examples, the set of engagement arms 628 may be upwardly sloped to allow for engagement with one or more stents with external protrusions. In at least one example, the set of engagement arms 628 can be engaged with the first end 654 and/or receiving aperture 658 to allow for storage during the procedure and/or insertion of the one or more stents.

In at least one embodiment, the coil stent 610, in at least one embodiment, is formed with coupling member(s) 616, and has one or more point set(s) 612. In some examples, the coil stent 610 may also include modifiable member(s) (not illustrated) that would allow for the coil stent 610 to be modified in a similar manner as the modifiable stent. While in other examples, the coil stent 610 may be formed from only modifiable member(s). The point set 612 of the coil stent 610 may include atraumatic point(s) 614A and/or traumatic point(s) 614B, individually or in combination, to allow for engagement with one or more vessels.

In at least one embodiment, the modifiable stent 604 is co-axially located or concentric to the coil stent 610. For clarity, in some examples, there can be a covering or sheath between the stents and/or vessels. The modifiable stent 604, in at least one example, is housed within the inner diameter of the coil stent 610. The concentric nature of the stent placements allows for the modifiable stent 604 to expand outwardly, to allow for proper fluid passage through the modifiable stent 604, while the coil stent 610 can engage with the vessels to prevent the movement of the modifiable stent 604 and/or the coil stent 610. In some examples, the lack of movement of the stents also allows for quicker healing when their vessels are placed in close proximity.

The modifiable stent (not illustrated) may be separated from the coil stent 610 and/or compression tool 620 by a sheath or cover 670. In at least one example, the sheath or cover 670 may include various tears or perforations that allow for it to be removed easier from the one or more stents. In other examples, the sheath or cover 6709 may be formed of a material that can define a cover void 672 that can receive and/or surround one or more stents.

Figure 7A:
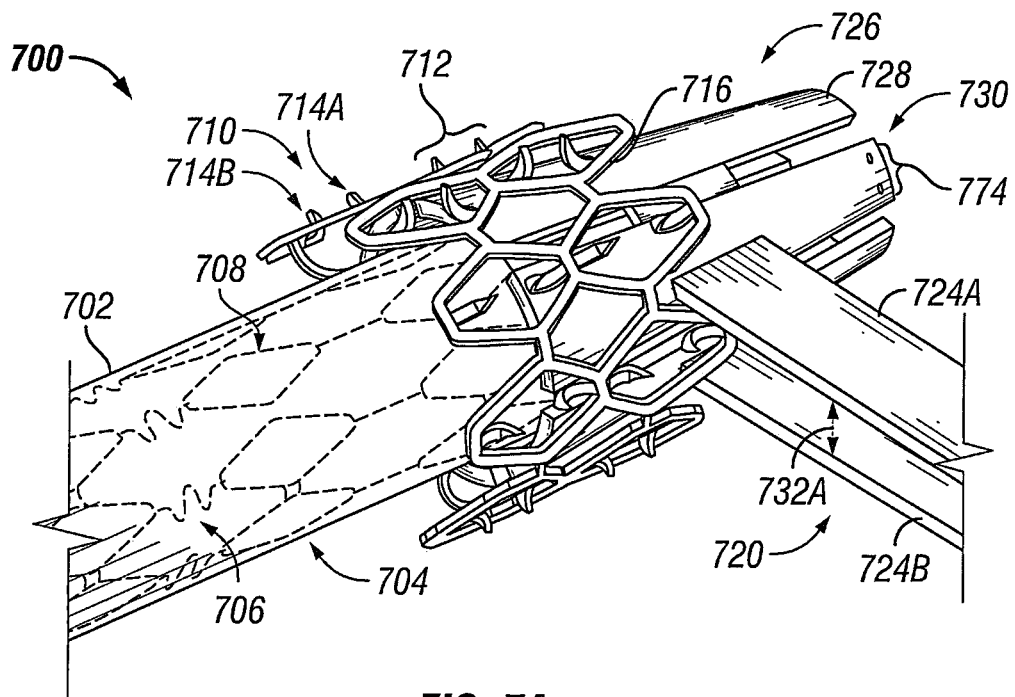
FIG. 7A is a perspective view illustration of a stent delivery system having a donor vessel, a modifiable stent, a coil stent, and a compression tool in an open state.

FIG. 7A is a perspective view illustration of a stent delivery system 700 having a donor vessel 702, a modifiable stent 704, a coil stent 710, and a compression tool 720 in an open state 732A. The stent delivery system 700, in at least one example, provides a user (a medical professional) with the ability to compress one or more stents, such as but not limited to the modifiable stent 704 and/or coil stent 710, for easy of entry and/or placement within one or more vessels such as, but not limited to the donor vessel 702 and/or a recipient vessel (not illustrated). In some examples, the compression tool 720 engages with one or both of the stents (illustrated as modifiable stent 704 and/or coil stent 710), to allow for the easy of insertion into one or more vessels.

In at least one embodiment, the modifiable stent 704 is formed with a combination of modifiable member(s) 706 and non-modifiable member(s) 708. While in some examples, the modifiable stent 704 may be comprised only modifiable member(s) 706 or non-modifiable member(s) 708. Additionally, in at least one example, the modifiable stent 704 may also have additional traumatic or atraumatic anchor points (not illustrated) that allow for the modifiable stent 704 to be anchored to a specific location or position within the vessel(s) or lumen.

Similarly, the coil stent 710, in at least one embodiment, is formed with coupling member(s) 716, and has a point set 712. In some examples, the coil stent 710 may also include modifiable member(s) (not illustrated) that would allow for the coil stent 710 to be modified in a similar manner as the modifiable stent 704. While in other examples, the coil stent 710 may be formed from only modifiable member(s). The point set 712 of the coil stent 710 may include atraumatic point(s) 714A and/or traumatic point(s) 714B, individually or in combination, to allow for engagement with one or more vessels, such as but not limited to a recipient vessel (not illustrated) and/or donor vessel 702.

In at least one embodiment, the modifiable stent 704 is co-axially located or concentric to the coil stent 710. For clarity, in some examples, there can be a covering or sheath between the stents and/or vessels. The modifiable stent 704, in at least one example, is housed within the inner diameter of the coil stent 710. The concentric nature of the stent placements allows for the modifiable stent 704 to expand outwardly, to allow for proper fluid passage through the modifiable stent 704, while the coil stent 710 can engage with the vessels (illustrated as recipient vessel (not illustrated) and/or donor vessel 702) to prevent the movement of the modifiable stent 704 and/or the coil stent 710. In some examples, the lack of movement of the stents also allows for quicker healing when their vessels are placed in close proximity.

The engagement section 726, in at least one embodiment, can be connected by arms 724A and/or 724B. The arms 724A/724B, in at least one example, may be of a length that allows for a reasonable force to be applied by a user to compress and/or close the engagement zone 726. The engagement zone 726, can have an internal void 730 that is defined by a set of engagement arms 728. The set of engagement arms 728 can have lengths that allow for engagement with various portions of one or both of the stents described in the present disclosure. In at least one example, the set of engagement arms 728 may also have one or more coupling points 774. The coupling points 774 may allow for the compression tool 720 to interact and/or engage with vessels in a manner that avoids the vessel slipping or sliding in a direction away from the one or more stents.

In at least one example, the set of engagement arms 728 are elongated structures that are generally perpendicular to the arms 724A/724B. In some examples, the set of engagement arms 728 can be downwardly sloped to allow for additional engagement with one or more stents (not illustrated). In yet other examples, the set of engagement arms 728 may be upwardly sloped to allow for engagement with one or more stents with external protrusions. In at least one embodiment, the engagement arm(s) 728 and a tapered end can allow for a user to more easily engage and/or place the stents within a vessel, such as but not limited to the recipient vessel or donor vessel 702.

In some examples, the compression tool 720 may be called a tweezer tool because of its similarity in operation to a tweezer. In a similar operation, a user can apply a force to the arms to cause a closing action to occur. When a closing action occurs, the arms move closer together from the starting or open state 732A. Upon releasing or reducing the force, the arms will return to the starting or open state 732A.

Figure 7B:
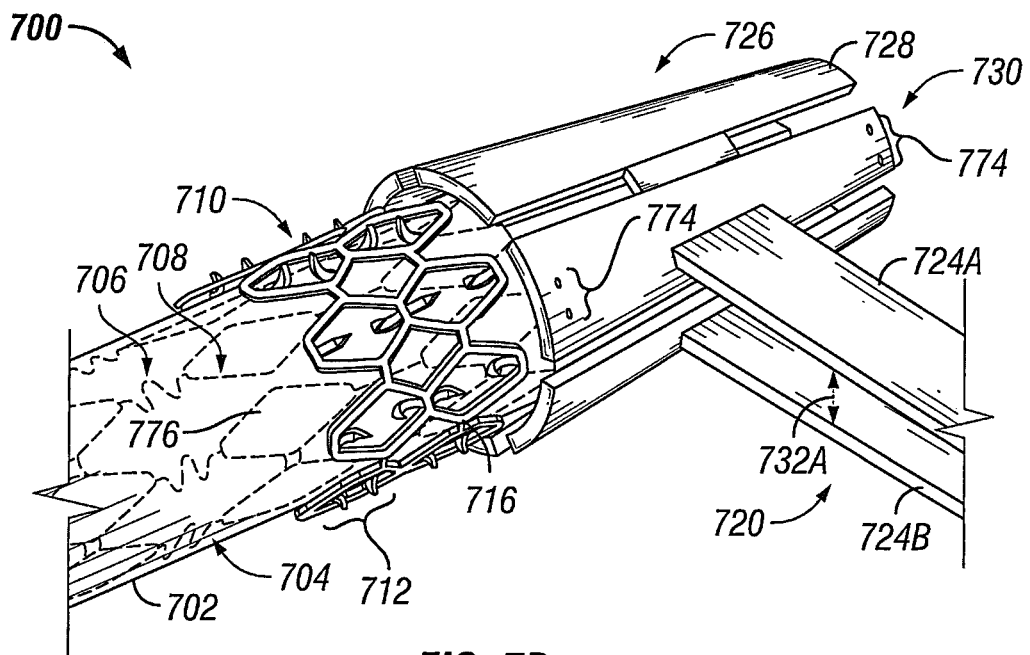
FIG. 7B is a perspective view illustration of a stent delivery system having a donor vessel, a modifiable stent, a coil stent, and a compression tool in an open state.

FIG. 7B is a perspective view illustration of a stent delivery system 700 having a donor vessel 702, a modifiable stent 704, a coil stent 710, and a compression tool 720 in an open state 732A. The stent delivery system 700, in at least one example, provides a user (a medical professional) with the ability to compress one or more stents, such as but not limited to the modifiable stent 704 and/or coil stent 710, for easy of entry and/or placement within one or more vessels such as, but not limited to the donor vessel 702 and/or a recipient vessel (not illustrated). In some examples, the compression tool 720 engages with one or both of the stents (illustrated as modifiable stent 704 and/or coil stent 710), to allow for the easy of insertion into one or more vessels.

In at least one embodiment, the modifiable stent 704 is formed with a combination of modifiable member(s) 706 and non-modifiable member(s) 708. While in some examples, the modifiable stent 704 may be comprised only modifiable member(s) 706 or non-modifiable member(s) 708. Additionally, in at least one example, the modifiable stent 704 may also have additional traumatic or atraumatic anchor points (not illustrated) that allow for the modifiable stent 704 to be anchored to a specific location or position within the vessel(s) or lumen. In some examples, the modifiable stent 704 may have one or more (a set of) receiving points 776 that may receive one or more anchor points of the coil stent 710. This may allow for the positioning of the stent in a more reliable manner.

Similarly, the coil stent 710, in at least one embodiment, is formed with coupling member(s) 716, and has a point set 712. In some examples, the coil stent 710 may also include modifiable member(s) (not illustrated) that would allow for the coil stent 710 to be modified in a similar manner as the modifiable stent 704. While in other examples, the coil stent 710 may be formed from only modifiable member(s). The point set 712 of the coil stent 710 may include atraumatic point(s) 714A and/or traumatic point(s) 714B, individually or in combination, to allow for engagement with one or more vessels, such as but not limited to a recipient vessel (not illustrated) and/or donor vessel 702.

In at least one embodiment, the modifiable stent 704 is co-axially located or concentric to the coil stent 710. For clarity, in some examples, there can be a covering or sheath between the stents and/or vessels. The modifiable stent 704, in at least one example, is housed within the inner diameter of the coil stent 710. The concentric nature of the stent placements allows for the modifiable stent 704 to expand outwardly, to allow for proper fluid passage through the modifiable stent 704, while the coil stent 710 can engage with the vessels (illustrated as recipient vessel (not illustrated) and/or donor vessel 702) to prevent the movement of the modifiable stent 704 and/or the coil stent 710. In some examples, the lack of movement of the stents also allows for quicker healing when their vessels are placed in close proximity.

The engagement section 726, in at least one embodiment, can be connected by arms 724A and/or 724B. The arms 724A/724B, in at least one example, may be of a length that allows for a reasonable force to be applied by a user to compress and/or close the engagement zone 726. The engagement zone 726, can have an internal void 730 that is defined by a set of engagement arms 728. The set of engagement arms 728 can have lengths that allow for engagement with various portions of one or both of the stents described in the present disclosure. In at least one example, the set of engagement arms 728 may also have one or more coupling points 774. The coupling points 774 may allow for the compression tool 720 to interact and/or engage with vessels in a manner that avoids the vessel slipping or sliding in a direction away from the one or more stents.

In at least one example, the set of engagement arms 728 are elongated structures that are generally perpendicular to the arms 724A/724B. In some examples, the set of engagement arms 728 can be downwardly sloped to allow for additional engagement with one or more stents (not illustrated). In yet other examples, the set of engagement arms 728 may be upwardly sloped to allow for engagement with one or more stents with external protrusions. In at least one embodiment, the engagement arm(s) 728 and a tapered end can allow for a user to more easily engage and/or place the stents within a vessel, such as but not limited to the recipient vessel or donor vessel 702.

In some examples, the compression tool 720 may be called a tweezer tool because of its similarity in operation to a tweezer. In a similar operation, a user can apply a force to the arms to cause a closing action 732B to occur. When a closing action 732B occurs, the arms move closer together from the starting or open state illustrated in FIG. 7A. Upon releasing or reducing the force, the arms will return to the starting or open state.

Figure 7C:
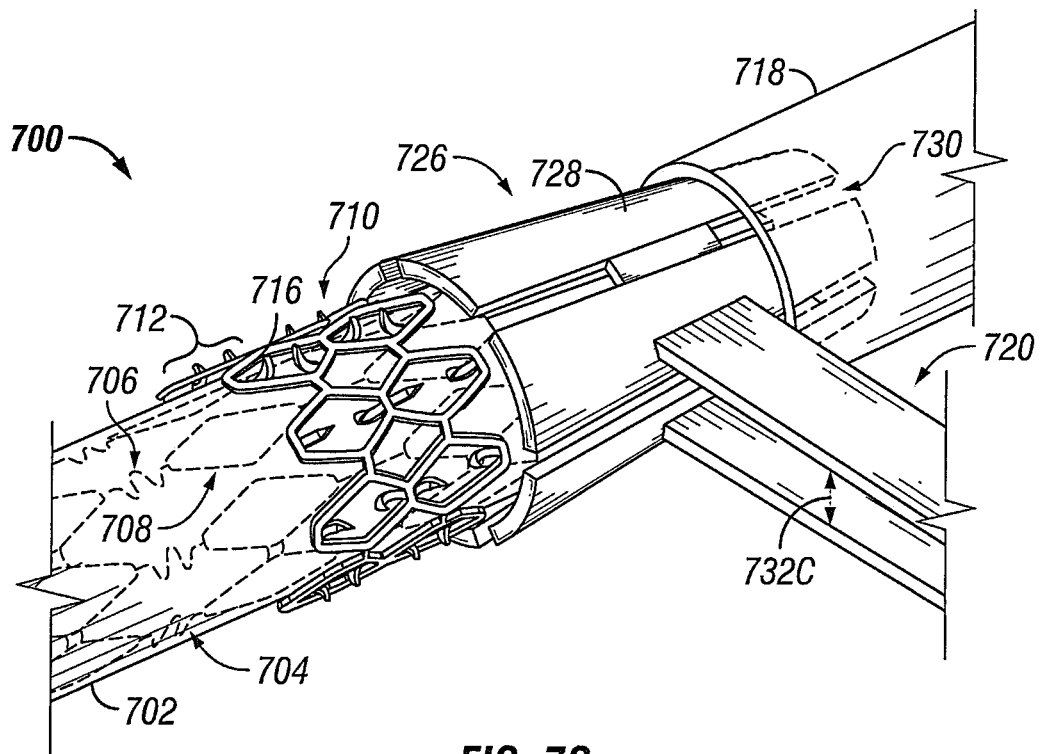
FIG. 7C is a perspective view illustration of a stent delivery system having a recipient vessel, a donor vessel, a modifiable stent, a coil stent, and a compression tool in an open state.

FIG. 7C is a perspective view illustration of a stent delivery system 700 having a recipient vessel 718, a donor vessel 702, a modifiable stent 704, a coil stent 710, and a compression tool 720 in an open state 732A. The stent delivery system 700, in at least one example, provides a user (a medical professional) with the ability to compress one or more stents, such as but not limited to the modifiable stent 704 and/or coil stent 710, for easy of entry and/or placement within one or more vessels such as, but not limited to the donor vessel 702 and/or a recipient vessel 718. In some examples, the compression tool 720 engages with one or both of the stents (illustrated as modifiable stent 704 and/or coil stent 710), to allow for the easy of insertion into one or more vessels.

In at least one embodiment, the modifiable stent 704 is formed with a combination of modifiable member(s) 706 and non-modifiable member(s) 708. While in some examples, the modifiable stent 704 may be comprised only modifiable member(s) 706 or non-modifiable member(s) 708. Additionally, in at least one example, the modifiable stent 704 may also have additional traumatic or atraumatic anchor points (not illustrated) that allow for the modifiable stent 704 to be anchored to a specific location or position within the vessel(s) or lumen.

Similarly, the coil stent 710, in at least one embodiment, is formed with coupling member(s) 716, and has a point set 712. In some examples, the coil stent 710 may also include modifiable member(s) (not illustrated) that would allow for the coil stent 710 to be modified in a similar manner as the modifiable stent 704. While in other examples, the coil stent 710 may be formed from only modifiable member(s). The point set 712 of the coil stent 710 may include atraumatic point(s) 714A and/or traumatic point(s) 714B, individually or in combination, to allow for engagement with one or more vessels, such as but not limited to a recipient vessel 718 and/or donor vessel 702.

In at least one embodiment, the modifiable stent 704 is co-axially located or concentric to the coil stent 710. For clarity, in some examples, there can be a covering or sheath between the stents and/or vessels. The modifiable stent 704, in at least one example, is housed within the inner diameter of the coil stent 710. The concentric nature of the stent placements allows for the modifiable stent 704 to expand outwardly, to allow for proper fluid passage through the modifiable stent 704, while the coil stent 710 can engage with the vessels (illustrated as recipient vessel 718 and/or donor vessel 702) to prevent the movement of the modifiable stent 704 and/or the coil stent 710. In some examples, the lack of movement of the stents also allows for quicker healing when their vessels are placed in close proximity.

The engagement section 726, in at least one embodiment, can be connected by arms 724A and/or 724B. The arms 724A/724B, in at least one example, may be of a length that allows for a reasonable force to be applied by a user to compress and/or close the engagement zone 726. The engagement zone 726, can have an internal void 730 that is defined by a set of engagement arms 728. The set of engagement arms 728 can have lengths that allow for engagement with various portions of one or both of the stents described in the present disclosure. In at least one example, the set of engagement arms 728 may also have one or more coupling points 774. The coupling points 774 may allow for the compression tool 720 to interact and/or engage with vessels in a manner that avoids the vessel slipping or sliding in a direction away from the one or more stents.

In at least one example, the set of engagement arms 728 are elongated structures that are generally perpendicular to the arms 724A/724B. In some examples, the set of engagement arms 728 can be downwardly sloped to allow for additional engagement with one or more stents (not illustrated). In yet other examples, the set of engagement arms 728 may be upwardly sloped to allow for engagement with one or more stents with external protrusions. In at least one embodiment, the engagement arm(s) 728 and a tapered end can allow for a user to more easily engage and/or place the stents within a vessel, such as but not limited to the recipient vessel or donor vessel 702.

In some examples, the compression tool 720 may be called a tweezer tool because of its similarity in operation to a tweezer. In a similar operation, a user can apply a force to the arms to cause a closing action 732C to occur. When a closing action 732C occurs, the arms move closer together from the starting or open state illustrated in FIG. 7A. Upon releasing or reducing the force, the arms will return to the starting or open state.

Figure 7D:
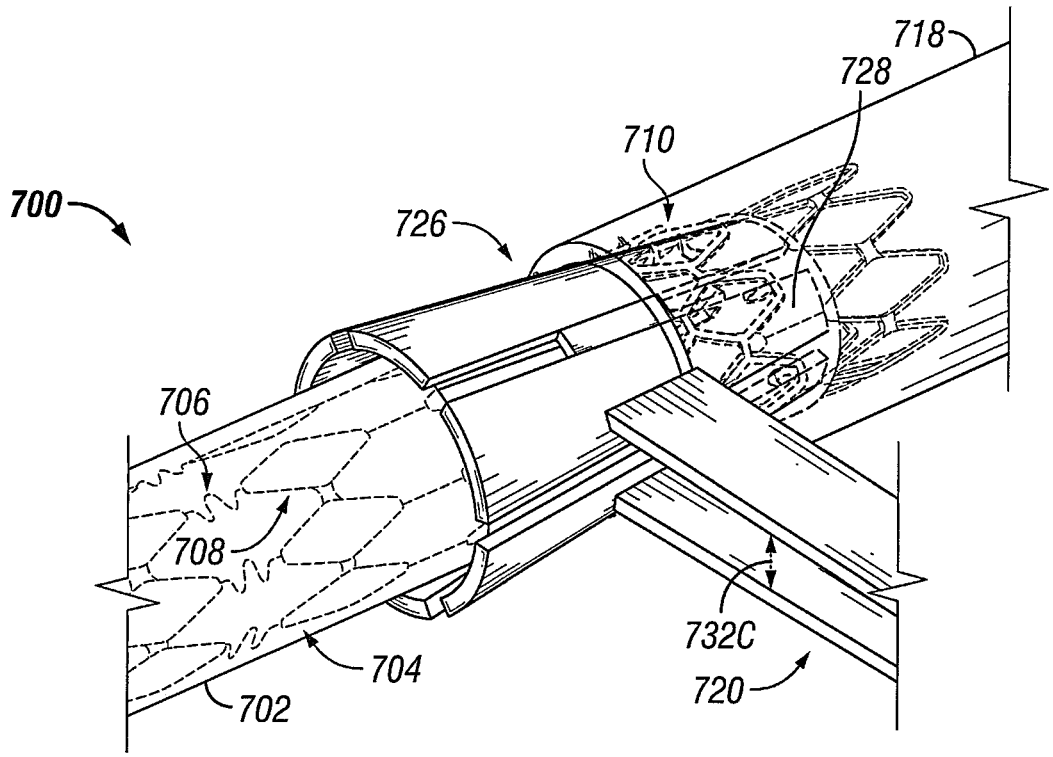
FIG. 7D is a perspective view illustration of a stent delivery system having a recipient vessel, a donor vessel, a modifiable stent, a coil stent, and a compression tool in an open state.

FIG. 7D is a perspective view illustration of a stent delivery system 700 having a recipient vessel 718, a donor vessel 702, a modifiable stent 704, a coil stent 710, and a compression tool 720 in an open state 732A. The stent delivery system 700, in at least one example, provides a user (a medical professional) with the ability to compress one or more stents, such as but not limited to the modifiable stent 704 and/or coil stent 710, for easy of entry and/or placement within one or more vessels such as, but not limited to the donor vessel 702 and/or a recipient vessel 718. In some examples, the compression tool 720 engages with one or both of the stents (illustrated as modifiable stent 704 and/or coil stent 710), to allow for the easy of insertion into one or more vessels.

In at least one embodiment, the modifiable stent 704 is formed with a combination of modifiable member(s) 706 and non-modifiable member(s) 708. While in some examples, the modifiable stent 704 may be comprised only modifiable member(s) 706 or non-modifiable member(s) 708. Additionally, in at least one example, the modifiable stent 704 may also have additional traumatic or atraumatic anchor points (not illustrated) that allow for the modifiable stent 704 to be anchored to a specific location or position within the vessel(s) or lumen.

Similarly, the coil stent 710, in at least one embodiment, is formed with coupling member(s) 716, and has a point set 712. In some examples, the coil stent 710 may also include modifiable member(s) (not illustrated) that would allow for the coil stent 710 to be modified in a similar manner as the modifiable stent 704. While in other examples, the coil stent 710 may be formed from only modifiable member(s). The point set 712 of the coil stent 710 may include atraumatic point(s) 714A and/or traumatic point(s) 714B, individually or in combination, to allow for engagement with one or more vessels, such as but not limited to a recipient vessel 718 and/or donor vessel 702.

In at least one embodiment, the modifiable stent 704 is co-axially located or concentric to the coil stent 710. For clarity, in some examples, there can be a covering or sheath between the stents and/or vessels. The modifiable stent 704, in at least one example, is housed within the inner diameter of the coil stent 710. The concentric nature of the stent placements allows for the modifiable stent 704 to expand outwardly, to allow for proper fluid passage through the modifiable stent 704, while the coil stent 710 can engage with the vessels (illustrated as recipient vessel 718 and/or donor vessel 702) to prevent the movement of the modifiable stent 704 and/or the coil stent 710. In some examples, the lack of movement of the stents also allows for quicker healing when there vessels are placed in close proximity.

The engagement section 726, in at least one embodiment, can be connected by arms 724A and/or 724B. The arms 724A/724B, in at least one example, may be of a length that allows for a reasonable force to be applied by a user to compress and/or close the engagement zone 726. The engagement zone 726, can have an internal void 730 that is defined by a set of engagement arms 728. The set of engagement arms 728 can have lengths that allow for engagement with various portions of one or both of the stents described in the present disclosure. In at least one example, the set of engagement arms 728 may also have one or more coupling points 774. The coupling points 774 may allow for the compression tool 720 to interact and/or engage with vessels in a manner that avoids the vessel slipping or sliding in a direction away from the one or more stents.

In at least one example, the set of engagement arms 728 are elongated structures that are generally perpendicular to the arms 724A/724B. In some examples, the set of engagement arms 728 can be downwardly sloped to allow for additional engagement with one or more stents (not illustrated). In yet other examples, the set of engagement arms 728 may be upwardly sloped to allow for engagement with one or more stents with external protrusions. In at least one embodiment, the engagement arm(s) 728 and a tapered end can allow for a user to more easily engage and/or place the stents within a vessel, such as but not limited to the recipient vessel or donor vessel 702.

In some examples, the compression tool 720 may be called a tweezer tool because of its similarity in operation to a tweezer. In a similar operation, a user can apply a force to the arms to cause a closing action to occur. When a closing action occurs, the arms move closer together from the starting or open state 732D. Upon releasing or reducing the force, the arms will return to the starting or open state 732D.

Figure 8A:
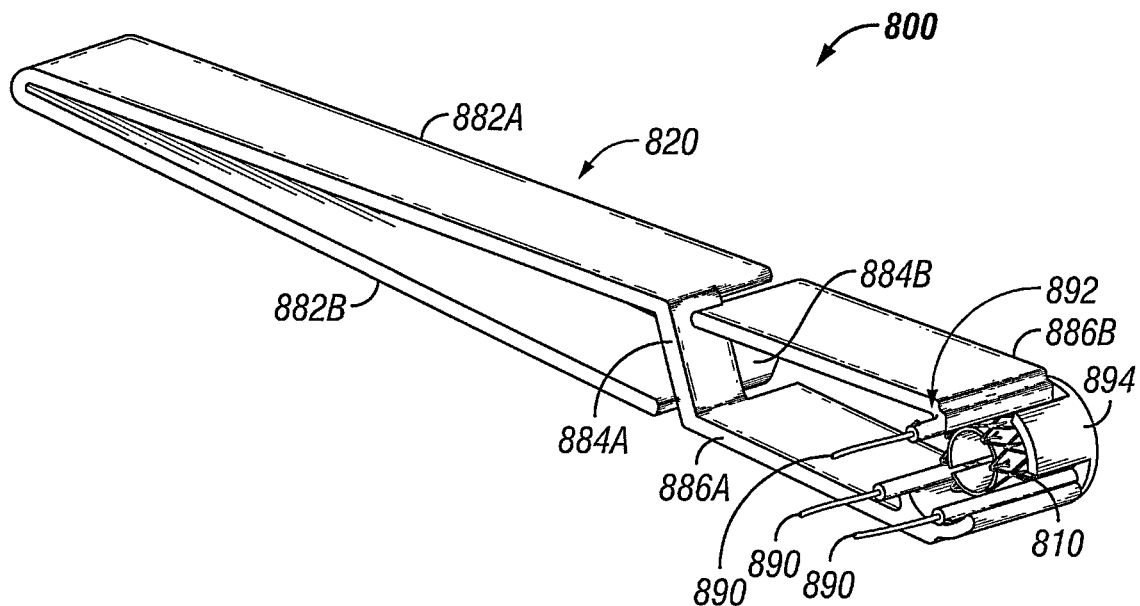
FIG. 8A is a perspective view illustration of stent delivery system having a delivery tool and a coil stent.

FIG. 8A is a perspective view illustration of stent delivery system 800 having a delivery tool 880, and a coil stent 810. The delivery tool 880 allows for a vessel (not illustrated) to be guided into a position that the coil stent 810 can be delivered. The delivery tool 880 has a first end or engagement section that is opposite and distal form an inflection point. The inflection point allows for the spring and/or resistive force that allows the delivery tool 880 to remain in a neutral state when not compressed by a user or external force (not illustrated).

The engagement section and the inflection point, in at least one embodiment, can be connected by arms 882A and/or 882B. The arms 882A/882B, in at least one example, may be of a length that allows for a reasonable force to be applied by a user to compress the arms 882A/882B and/or open the engagement zone. Transfer arms 884A and/or 884B can allow a for the transfer of the compression or reasonable force applied by a user to extension arms 886A and/or 886B. The transfer arms 884A/884B may be of a length that allows for the closing of the engagement zone when the delivery tool 880 is in a neutral state and are generally perpendicular to the arms 882A/882B and/or extension arms 886A/886B. In some examples, engagement zone may also be referenced as an engagement section. The extension arms 886A/886B can act as an extension of the arms 882A/882B but are in opposite planes in order to allow for the expansion of the delivery tool 880. For example, arm 882A corresponds to the extension arm 886B, and arm 882B corresponds to extension arm 886A. This cross over is possible because of the transfer arms 884A/884B.

In some examples, the delivery tool 880 may be called an expander tool because of its similarity in operation to an expander used in orthodontics to push two points away from one another. In a similar operation, a user can apply a force to the arms to cause an opening action to occur. When an opening action occurs, the arms move closer together from the starting or open state allowing the engagement zone to open. Upon releasing or reducing the force, the arms will return to the starting or open state and the engagement zone will return to its closed state.

The engagement zone, in at least one embodiment, may include a set of guides 890 that provide direction for the coupling of the delivery tool 880 to a vessel (not illustrated). The set of guides 890, in at least one example, can include engagement points 892 that can engage with the vessel to prevent it from moving during the delivery and/or insertion of the stent 810. The delivery tool 880 can also include a transfer guide 894 that allows for guiding the stent 810 into position within a vessel. The transfer guide 894 can include a portion that goes within the stent 810 and a portion that surrounds the outside of the stent 810. In at least one example, there can be a transfer guide engagement zone 891 between the outer portion of the transfer guide 894 and the stent 810. In at least one embodiment, the transfer guide 894 is removable with the stent 810 from the engagement zone of the delivery tool 880.

Figure 8B:
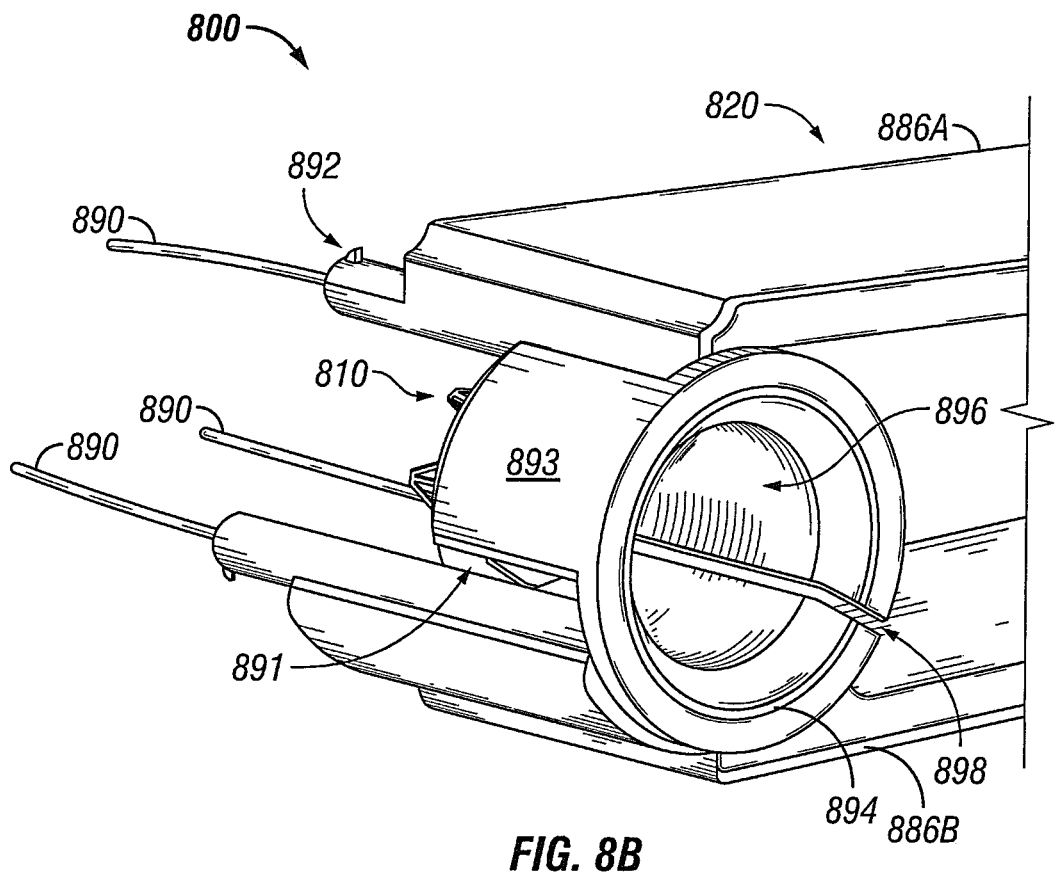
FIG. 8B is a perspective view illustration of a delivery tool and a coil stent.

FIG. 8B is a perspective view illustration of a delivery tool 880 and a coil stent 810. The delivery tool 880 allows for a vessel (not illustrated) to be guided into a position that the coil stent 810 can be delivered. The delivery tool 880 has a first end or engagement section that is opposite and distal form an inflection point. The inflection point allows for the spring and/or resistive force that allows the delivery tool 880 to remain in a neutral state when not compressed by a user or external force (not illustrated).

Transfer arms can allow a for the transfer of the compression or reasonable force applied by a user to extension arms 886A and/or 886B. In some examples, engagement zone may also be referenced as an engagement section. The extension arms 886A/886B can act as an extension of the arms but are in opposite planes in order to allow for the expansion of the delivery tool 880.

In some examples, the delivery tool 880 may be called an expander tool because of its similarity in operation to an expander used in orthodontics to push two points away from one another. In a similar operation, a user can apply a force to the arms to cause an opening action to occur. When an opening action occurs, the arms move closer together from the starting or open state allowing the engagement zone to open. Upon releasing or reducing the force, the arms will return to the starting or open state and the engagement zone will return to its closed state.

The engagement zone, in at least one embodiment, may include a set of guides 890 that provide direction for the coupling of the delivery tool 880 to a vessel (not illustrated). The set of guides 890, in at least one example, can include engagement points 892 that can engage with the vessel to prevent it from moving during the delivery and/or insertion of the stent 810. The delivery tool 880 can also include a transfer guide 894 that allows for guiding the stent 810 into position within a vessel. The transfer guide 894 can include a portion that goes within the stent 810 and a portion that surrounds the outside of the stent 810. In at least one example, there can be a transfer guide engagement zone 891 between the outer portion of the transfer guide 894 and the stent 810. In at least one embodiment, the transfer guide 894 is removable with the stent 810 from the engagement zone of the delivery tool 880.

The transfer guide 894, in at least one example, may also include engagement neck 893 that can prevent the expansion of the stent 810 and/or engage with a vessel to allow for ease of insertion. An internal void 896 of the transfer guide 894 can be present and allow for additional stents and/or tools to be inserted into the vessel. For example, a first stent may be inserted while the coil stent 810 is wrapped around it as a specific point. Alternatively, the coil stent 810 may be delivered onto a first vessel that may or may not have a stent within in it, while a second vessel is engage with the guides allowing the coil stent 810 to engage the first and second vessels for potential healing together. As part of this example, a transfer guide notch 898 may be utilized to push and/or guide the stent 810 away from the transfer guide 894 and/or delivery tool 880.

Figure 9A:
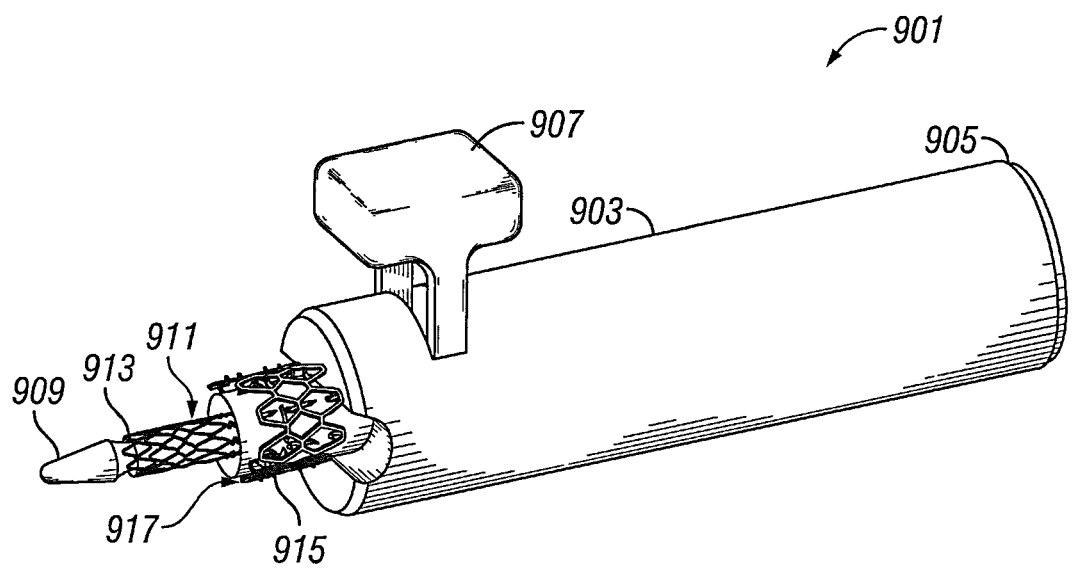
FIG. 9A is a perspective view illustration of a dual stent delivery tool that can be utilized as an apparatus and system, and as part of a method of using the dual stents.

FIG. 9A is a perspective view illustration of a dual stent delivery tool 901 (in some examples a stent delivery tool 901) can be utilized as an apparatus and system, and as part of a method of using the dual stents. In at least one embodiment, the dual stent delivery tool 901 may be utilized to place two stents with a single button press, allowing for the first portion of an amitosis surgery to be completed in just a few seconds, rather than the current methods which can take up to ten to twenty minutes per vessel. In some examples, the dual stent delivery tool 901 be included as part of a set of delivery tools or in sterilized blister packs that can be opened and utilized in rapid succession during intensive surgery.

The dual stent delivery tool 901 can have a main body 903 for housing the internal workings of the stent delivery tool 901, and in at least one example, partially housing and/or containing one or more stents. In at least one embodiment, the main body 903 can be cylindrical, with a first end having a back stop 905, and a second end opposing the first end, and the second end having an opening to receive the one or more stents. In some examples, the main body 903 may have additional openings, apertures, or other structures that pass through or along portions of the main body 903. The back stop 905 may be threaded, friction fit, or otherwise coupled to the main body 903 in a manner that prevents it from being removed from the main body 903 without additional outside forces.

A firing tab or button 907 may be utilized by a user or medical professional to activate the mechanisms to transfer one or both of the stents. It would be understood, that while one button is illustrated, in at least one example two or more buttons may be utilized to trigger the transfer and/or insertion of one or more stents and/or other activities related to these and similar procedures. In some examples of the dual stent delivery tool 901, there may be additional firing tab(s) or button(s) 907 to allow for vessels to be engaged or disengaged, along with the engagement or disengagement of one or more stents.

When the firing tab 907 is pressed, a lead in 909, in some examples called an olive tip lead in, can extend or retract based on the design of the dual stent delivery tool 901. The lead in 909 can be shaped like a rounded bullet with a tapered front end, coupled to a cylindrical section, and a tapered rear section that coupled to a plunger and/or rod. While the olive shape is illustrated, other shapes may be utilized without departing from the spirit of the present disclosure.

In at least one embodiment, the lead in 909 can engage and/or interact with an inner stent 911. In at least one example, the inner stent 911 can be a modifiable stent that is capable of expanding and/or retracting on itself. In yet other examples, the inner stent 911 may also have one or more anchor points that when engaged can allow the inner stent 911 to be secured to a vessel (not illustrated). In at least one embodiment, an inner stent covering 913 can compress and/or prevent the modification of the inner stent 911 prior to the removal of the inner stent covering 913. In some examples, the inner stent covering 913 can be a flexible material with perforations that allow it to be ripped and/or removed in a quick movement without leaving any material behind. Similarly, the outer stent 915 can be a modifiable stent that is capable of expanding and/or retracting on itself. In yet other examples, the inner stent 915 may also have one or more anchor points that when engaged can allow the inner stent 915 to be secured to a vessel (not illustrated). In at least one embodiment, an inner stent covering 917 can compress and/or prevent the modification of the inner stent 915 prior to the removal of the inner stent covering 917. In some examples, the inner stent covering 917 can be a flexible material with perforations that allow it to be ripped and/or removed in a quick movement without leaving any material behind. The inner stent 911 can be co-axially related to the outer stent 915 such that the inner stent 911 is within the inner radius or diameter of the outer stent 915.

Figure 9B:
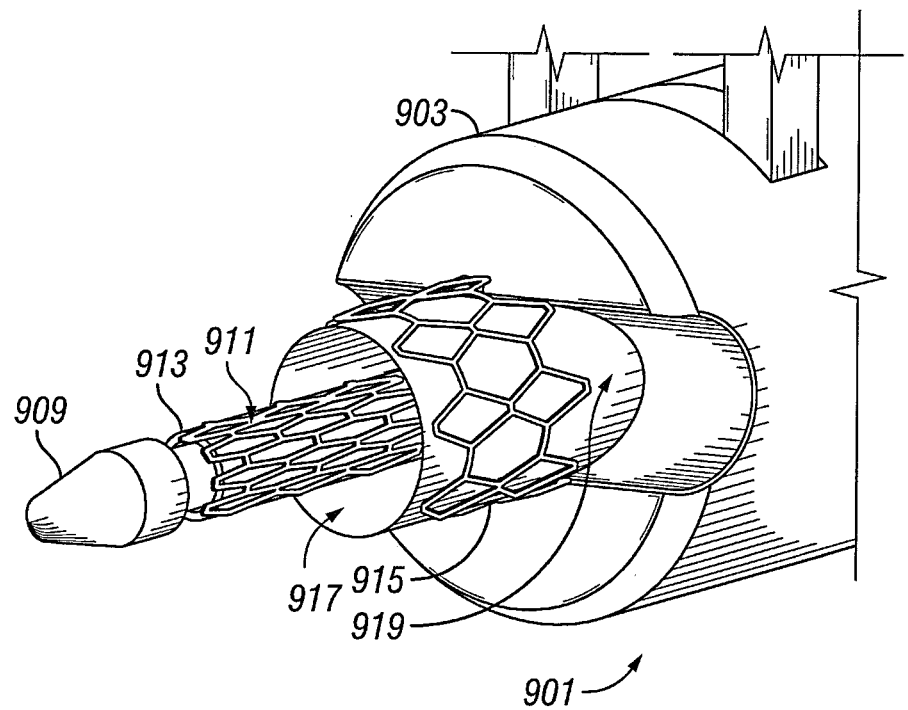
FIG. 9B is a perspective view illustration of a dual stent delivery tool in a zoomed view of the front section of the dual stent delivery tool.

FIG. 9B is a perspective view illustration of a dual stent delivery tool 901 in a zoomed view of the front section of the dual stent delivery tool 901. In at least one embodiment, the dual stent delivery tool 901 may be utilized to place two stents with a single button press, allowing for the first portion of an amitosis surgery to be completed in just a few seconds, rather than the current methods which can take up to ten to twenty minutes per vessel. In some examples, the dual stent delivery tool 901 be included as part of a set of delivery tools or in sterilized blister packs that can be opened and utilized in rapid succession during intensive surgery.

The dual stent delivery tool 901 can have a main body 903 for housing the internal workings of the stent delivery tool 901, and in at least one example, partially housing and/or containing one or more stents. In at least one embodiment, the main body 903 can be cylindrical, with a first end having a back stop 905, and a second end opposing the first end, and the second end having an opening to receive the one or more stents. In some examples, the main body 903 may have additional openings, apertures, or other structures that pass through or along portions of the main body 903. The back stop 905 may be threaded, friction fit, or otherwise coupled to the main body 903 in a manner that prevents it from being removed from the main body 903 without additional outside forces.

A firing tab or button 907 may be utilized by a user or medical professional to activate the mechanisms to transfer one or both of the stents. It would be understood, that while one button is illustrated, in at least one example two or more buttons may be utilized to trigger the transfer and/or insertion of one or more stents and/or other activities related to these and similar procedures. In some examples of the dual stent delivery tool 901, there may be additional firing tab(s) or button(s) 907 to allow for vessels to be engaged or disengaged, along with the engagement or disengagement of one or more stents.

When the firing tab 907 is pressed, a lead in 909, in some examples called an olive tip lead in, can extend or retract based on the design of the dual stent delivery tool 901. The lead in 909 can be shaped like a rounded bullet with a tapered front end, coupled to a cylindrical section, and a tapered rear section that coupled to a plunger and/or rod. While the olive shape is illustrated, other shapes may be utilized without departing from the spirit of the present disclosure.

In at least one embodiment, the lead in 909 can engage and/or interact with an inner stent 911. In at least one example, the inner stent 911 can be a modifiable stent that is capable of expanding and/or retracting on itself. In yet other examples, the inner stent 911 may also have one or more anchor points that when engaged can allow the inner stent 911 to be secured to a vessel (not illustrated). In at least one embodiment, an inner stent covering 913 can compress and/or prevent the modification of the inner stent 911 prior to the removal of the inner stent covering 913. In some examples, the inner stent covering 913 can be a flexible material with perforations that allow it to be ripped and/or removed in a quick movement without leaving any material behind. Similarly, the outer stent 915 can be a modifiable stent that is capable of expanding and/or retracting on itself. In yet other examples, the inner stent 915 may also have one or more anchor points that when engaged can allow the inner stent 915 to be secured to a vessel (not illustrated). In at least one embodiment, an inner stent covering 917 can compress and/or prevent the modification of the inner stent 915 prior to the removal of the inner stent covering 917. In some examples, the inner stent covering 917 can be a flexible material with perforations that allow it to be ripped and/or removed in a quick movement without leaving any material behind. The inner stent 911 can be co-axially related to the outer stent 915 such that the inner stent 911 is within the inner radius or diameter of the outer stent 915.

The main body 903 can include a body aperture 919 that allows for access to the internal portions of the main body 903. In at least one example, the body aperture 919 is sized and/or configured to allow for the passage and/or storage of one or both stents, a plunger or rod, a firing mechanism (not illustrated), and/or the lead in 909.

Figure 9C:
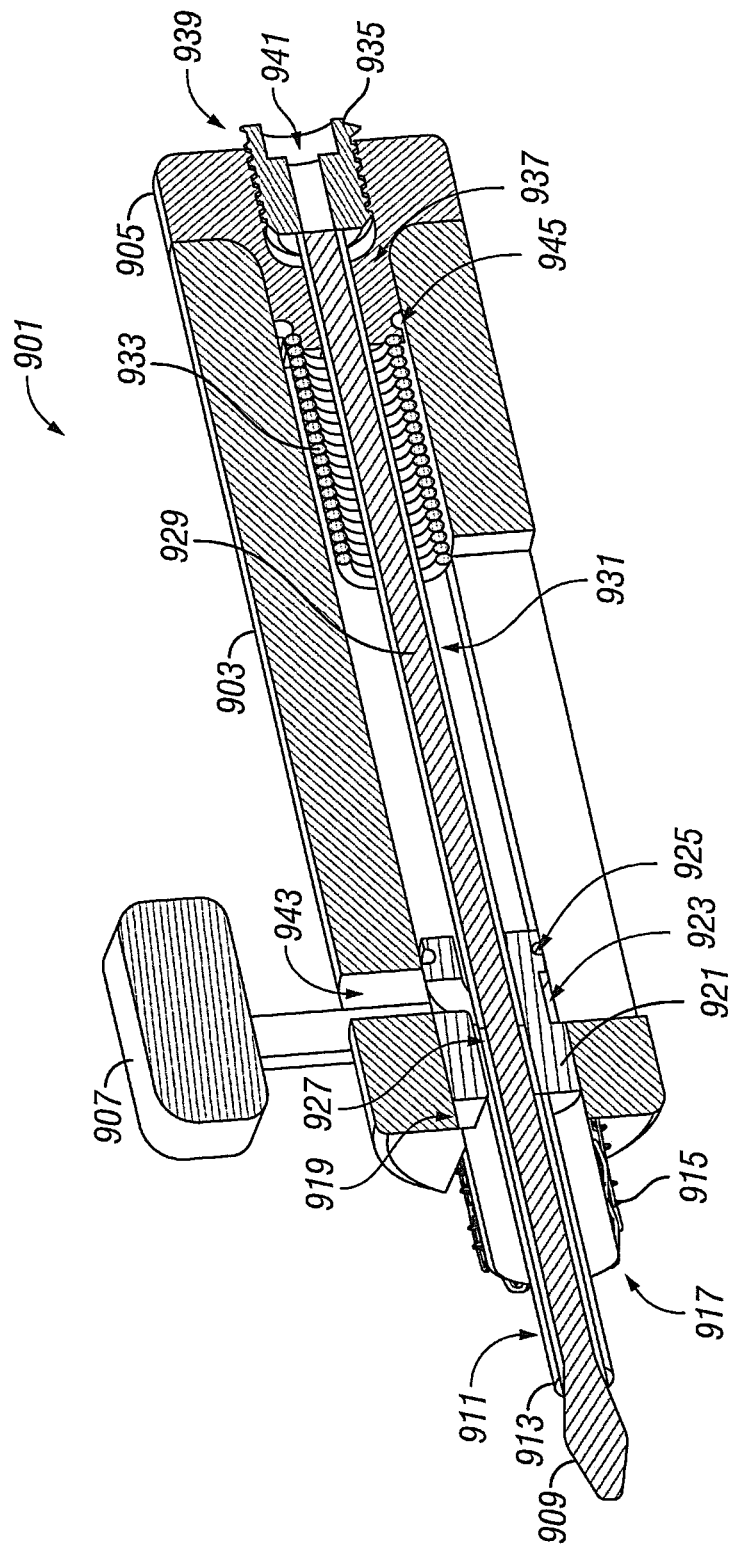
FIG. 9C is a cross-sectional view illustration of a dual stent delivery tool.

FIG. 9C is a cross-sectional view illustration of a dual stent delivery tool 901. In at least one embodiment, the dual stent delivery tool 901 may be utilized to place two stents with a single button press, allowing for the first portion of an amitosis surgery to be completed in just a few seconds, rather than the current methods which can take up to ten to twenty minutes per vessel. In some examples, the dual stent delivery tool 901 be included as part of a set of delivery tools or in sterilized blister packs that can be opened and utilized in rapid succession during intensive surgery.

The dual stent delivery tool 901 can have a main body 903 for housing the internal workings of the stent delivery tool 901, and in at least one example, partially housing and/or containing one or more stents. In at least one embodiment, the main body 903 can be cylindrical, with a first end having a back stop 905, and a second end opposing the first end, and the second end having an opening to receive the one or more stents. In some examples, the main body 903 may have additional openings, apertures, or other structures that pass through or along portions of the main body 903. The back stop 905 may be threaded, friction fit, or otherwise coupled to the main body 903 in a manner that prevents it from being removed from the main body 903 without additional outside forces.

A firing tab or button 907 may be utilized by a user or medical professional to activate the mechanisms to transfer one or both of the stents. It would be understood, that while one button is illustrated, in at least one example two or more buttons may be utilized to trigger the transfer and/or insertion of one or more stents and/or other activities related to these and similar procedures. In some examples of the dual stent delivery tool 901, there may be additional firing tab(s) or button(s) 907 to allow for vessels to be engaged or disengaged, along with the engagement or disengagement of one or more stents.

When the firing tab 907 is pressed, a lead in 909, in some examples called an olive tip lead in can extend or retract based on the design of the dual stent delivery tool 901. The lead in 909 can be shaped like a rounded bullet with a tapered front end, coupled to a cylindrical section, and a tapered rear section that coupled to a plunger and/or rod. While the olive shape is illustrated, other shapes may be utilized without departing from the spirit of the present disclosure.

In at least one embodiment, the lead in 909 can engage and/or interact with an inner stent 911. In at least one example, the inner stent 911 can be a modifiable stent that is capable of expanding and/or retracting on itself. In yet other examples, the inner stent 911 may also have one or more anchor points that when engaged can allow the inner stent 911 to be secured to a vessel (not illustrated). In at least one embodiment, an inner stent covering 913 can compress and/or prevent the modification of the inner stent 911 prior to the removal of the inner stent covering 913. In some examples, the inner stent covering 913 can be a flexible material with perforations that allow it to be ripped and/or removed in a quick movement without leaving any material behind. Similarly, the outer stent 915 can be a modifiable stent that is capable of expanding and/or retracting on itself. In yet other examples, the inner stent 915 may also have one or more anchor points that when engaged can allow the inner stent 915 to be secured to a vessel (not illustrated). In at least one embodiment, an inner stent covering 917 can compress and/or prevent the modification of the inner stent 915 prior to the removal of the inner stent covering 917. In some examples, the inner stent covering 917 can be a flexible material with perforations that allow it to be ripped and/or removed in a quick movement without leaving any material behind. The inner stent 911 can be co-axially related to the outer stent 915 such that the inner stent 911 is within the inner radius or diameter of the outer stent 915.

The main body 903 can include a body aperture 919 that allows for access to the internal portions of the main body 903. In at least one example, the body aperture 919 is sized and/or configured to allow for the passage and/or storage of one or both stents, a plunger or rod, a firing mechanism (not illustrated), and/or the lead in 909.

The cover carrier 921, in some examples a sheath carrier can allow for a coupling to the one or more sheaths or coverings for the stents of the present disclosure. In at least one example, the covers or sheaths are coupled to the cover carrier 921 in a manner that when the firing button or tab 907 is pressed it releases the cover carrier 921 to move and thereby moving the stent covers or sheaths as well. The cover carrier 921 may also have a cover carrier engagement aperture 923 that allows portions of the firing tab or button 907 to pass through and/or interact with the cover carrier 921. In some examples, the cover carrier engagement aperture 923 may be formed in such a way that it must be positioned correctly in order to engage or interact with portion of the firing tab or button 907, while in other examples, the cover carrier engagement aperture 923 may have a consistent configuration around the entire perimeter of the cover carrier 921. The cover carrier 921, in at least one embodiment, can have a cover carrier retention zone 925. The cover carrier retention zone 925 can be an area to receive a spring or other retention mechanism. In at least one embodiment, the cover carrier retention zone 925 may also be able to engage with a pushing or acceleration mechanism that can push the cover carrier 921 away from the back stop 905. The cover carrier retention zone 925 and/or the cover carrier engagement aperture 923 can surround and/or device a cover carrier pass through void 927 that allows a rod or plunger to pass through the cover carrier 921.

The lead in 909 can be coupled to a lead in shaft 929. The lead in shaft 929 can be a rod or plunger that passes through the body aperture 919. In some examples, it can couple with a plunger rod 931. In at least one example the plunger rod 931 surrounds the lead in shaft 929 to provide additional support. In other examples, the plunger rod 931 can be an extension of the lead in shaft 929.

In at least on embodiment, a retention mechanism 933 can be utilized to engage the cover carrier 921 backwards towards the back stop 905 or forwards towards the body aperture 919. In at least one example, the retention mechanism 933 is a spring, while in other example, other forms of mechanism that can impart kinetic energy may be utilized. When the firing tab or button 907 is engaged by the user and passes a portion of the firing tab or button through the main body firing tab aperture 943, the kinetic energy stored in the retention mechanism 933 can be released.

The retention mechanism 933 can be coupled between the cover carrier retention zone 925 and the back stop retention zone 945. The back stop retention zone 945 can be an area to receive a spring or other retention mechanism. In at least one embodiment, the back stop retention zone 945 may also be able to engage with a pushing or acceleration mechanism that can push the cover carrier 921 away from the back stop 905. The lead in 909 interaction depth with a vessel (not illustrated) can be adjusted with a depth adjustment 935. In at least one example, the depth adjustment 935 interacts with the back stop 905 though a threaded connection, while other connections that allow for changes of positioning between two elements would not depart from the spirit of the present disclosure. The threaded connection may be illustrated by a depth adjustment engagement surface 939 along the outer perimeter of the depth adjustment 935, and the inner perimeter of the back stop 905.

The lead in shaft 929 and/or plunger rod 931 can pass through and/or engage with a back stop aperture 937 defined by the back stop 905 and/or the depth adjustment aperture 941 defined by the depth adjustment 935. In at least one example, the back stop aperture 937 can allow for the passage of the lead in shaft 929 and the plunger rod 931 while the depth adjustment aperture 941 only allows for the passage of the lead in shaft 929. Further to this example, the depth of the lead in 909 engagement with a vessel can be controlled by the amount of the shaft and/or rod that is allowed to pass through them.

Figure 10:
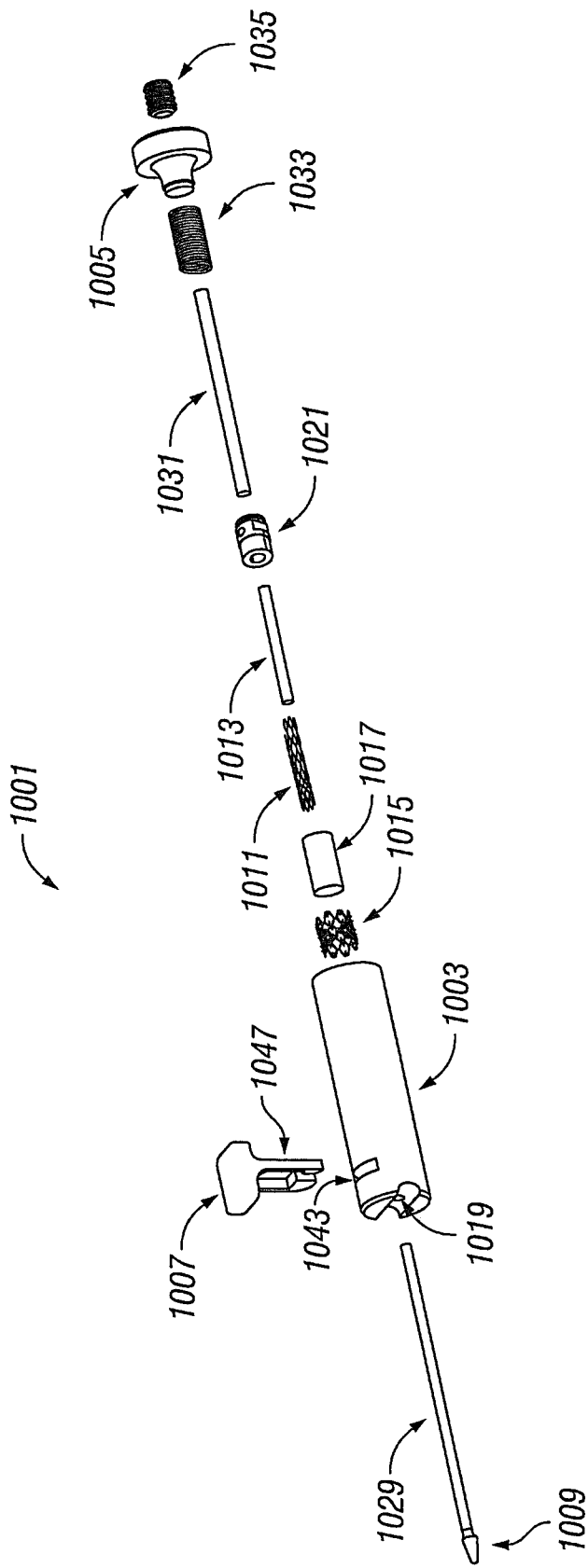
FIG. 10 is an exploded view illustration of a dual stent delivery tool.

FIG. 10 is an exploded view illustration of a dual stent delivery tool 1001. In at least one embodiment, the dual stent delivery tool 1001 may be utilized to place two stents with a single button press, allowing for the first portion of an amitosis surgery to be completed in just a few seconds, rather than the current methods which can take up to ten to twenty minutes per vessel. In some examples, the dual stent delivery tool 1001 be included as part of a set of delivery tools or in sterilized blister packs that can be opened and utilized in rapid succession during intensive surgery.

The dual stent delivery tool 1001 can have a main body 1003 for housing the internal workings of the stent delivery tool 1001, and in at least one example, partially housing and/or containing one or more stents. In at least one embodiment, the main body 1003 can be cylindrical, with a first end having a back stop 1005, and a second end opposing the first end, and the second end having an opening to receive the one or more stents. In some examples, the main body 1003 may have additional openings, apertures, or other structures that pass through or along portions of the main body 1003. The back stop 1005 may be threaded, friction fit, or otherwise coupled to the main body 1003 in a manner that prevents it from being removed from the main body 1003 without additional outside forces. The main body 1003 may house all of the components with the exception of portions of the lead in 1009 and/or lead in shaft 1029, firing tab or button 1007, the back stop 1005, and/or depth adjustment 1035.

A firing tab or button 1007 may be utilized by a user or medical professional to activate the mechanisms to transfer one or both of the stents. It would be understood, that while one button is illustrated, in at least one example two or more buttons may be utilized to trigger the transfer and/or insertion of one or more stents and/or other activities related to these and similar procedures. The firing tab or button 1007 may include firing tab or button engagement extensions 1047 that can engage with the cover carrier 1021. In at least one example, the firing tab or button 1007 when pressed the firing tab extension 1047 passes through the cover carrier engagement aperture releasing the cover carrier 1021 to move. In some examples of the dual stent delivery tool 901, there may be additional firing tab(s) or button(s) 1007 to allow for vessels to be engaged or disengaged, along with the engagement or disengagement of one or more stents.

When the firing tab 1007 is pressed, a lead in 1009, in some examples called an olive tip lead in, can extend or retract based on the design of the dual stent delivery tool 1001. The lead in 1009 can be shaped like a rounded bullet with a tapered front end, coupled to a cylindrical section, and a tapered rear section that coupled to a plunger and/or rod. While the olive shape is illustrated, other shapes may be utilized without departing from the spirit of the present disclosure.

In at least one embodiment, the lead in 1009 can engage and/or interact with an inner stent 1011. In at least one example, the inner stent 1011 can be a modifiable stent that is capable of expanding and/or retracting on itself. In yet other examples, the inner stent 1011 may also have one or more anchor points that when engaged can allow the inner stent 1011 to be secured to a vessel (not illustrated). In at least one embodiment, an inner stent covering 1013 can compress and/or prevent the modification of the inner stent 1011 prior to the removal of the inner stent covering 1013. In some examples, the inner stent covering 1013 can be a flexible material with perforations that allow it to be ripped and/or removed in a quick movement without leaving any material behind. Similarly, the outer stent 1015 can be a modifiable stent that is capable of expanding and/or retracting on itself. In yet other examples, the inner stent 1015 may also have one or more anchor points that when engaged can allow the inner stent 1015 to be secured to a vessel (not illustrated). In at least one embodiment, an inner stent covering 1017 can compress and/or prevent the modification of the inner stent 1015 prior to the removal of the inner stent covering 1017. In some examples, the inner stent covering 1017 can be a flexible material with perforations that allow it to be ripped and/or removed in a quick movement without leaving any material behind. The inner stent 1011 can be co-axially related to the outer stent 1015 such that the inner stent 1011 is within the inner radius or diameter of the outer stent 1015.

The main body 1003 can include a body aperture 1019 that allows for access to the internal portions of the main body 1003. In at least one example, the body aperture 1019 is sized and/or configured to allow for the passage and/or storage of one or both stents, a plunger or rod, a firing mechanism (not illustrated), and/or the lead in 1009.

The cover carrier 1021, in some examples a sheath carrier can allow for a coupling to the one or more sheaths or coverings for the stents of the present disclosure. In at least one example, the covers or sheaths are coupled to the cover carrier 1021 in a manner that when the firing button or tab 1007 is pressed it releases the cover carrier 1021 to move and thereby moving the stent covers or sheaths as well. The cover carrier 1021 may also have a cover carrier engagement aperture that allows portions of the firing tab or button 1007, such as but not limited to firing tab or button extensions 1047 to pass through and/or interact with the cover carrier 1021. In some examples, the cover carrier engagement aperture may be formed in such a way that it must be positioned correctly in order to engage or interact with portion of the firing tab or button 1007, while in other examples, the cover carrier engagement aperture may have a consistent configuration around the entire perimeter of the cover carrier 1021. The cover carrier 1021, in at least one embodiment, can have a cover carrier retention zone. The cover carrier retention zone can be an area to receive a spring or other retention mechanism. In at least one embodiment, the cover carrier retention zone may also be able to engage with a pushing or acceleration mechanism that can push the cover carrier 1021 away from the back stop 1005. The cover carrier retention zone and/or the cover carrier engagement aperture can surround and/or device a cover carrier pass through void that allows a rod or plunger to pass through the cover carrier 1021.

The lead in 1009 can be coupled to a lead in shaft 1029. The lead in shaft 1029 can be a rod or plunger that passes through the body aperture 1019. In some examples, it can couple with a plunger rod 1031. In at least one example the plunger rod 1031 surrounds the lead in shaft 1029 to provide additional support. In other examples, the plunger rod 1031 can be an extension of the lead in shaft 1029.

In at least on embodiment, a retention mechanism 1033 can be utilized to engage the cover carrier 1021 backwards towards the back stop 1005 or forwards towards the body aperture 1019. In at least one example, the retention mechanism 1033 is a spring, while in other example, other forms of mechanism that can impart kinetic energy may be utilized. When the firing tab or button 1007 is engaged by the user and passes a portion of the firing tab or button through the main body firing tab aperture, the kinetic energy stored in the retention mechanism 1033 can be released.

The retention mechanism 1033 can be coupled between the cover carrier retention zone and the back stop retention zone. The back stop retention zone can be an area to receive a spring or other retention mechanism 1033. In at least one embodiment, the back stop retention zone may also be able to engage with a pushing or acceleration mechanism that can push the cover carrier 1021 away from the back stop 1005. The lead in 1009 interaction depth with a vessel (not illustrated) can be adjusted with a depth adjustment 1035. In at least one example, the depth adjustment 1035 interacts with the back stop 1005 though a threaded connection, while other connections that allow for changes of positioning between two elements would not depart from the spirit of the present disclosure. The threaded connection may be illustrated by a depth adjustment engagement surface along the outer perimeter of the depth adjustment 1035, and the inner perimeter of the back stop 1005.

The lead in shaft 1029 and/or plunger rod 1031 can pass through and/or engage with a back stop aperture defined by the back stop 1005 and/or the depth adjustment aperture defined by the depth adjustment 1035. In at least one example, the back stop aperture can allow for the passage of the lead in shaft 1029 and the plunger rod 1031 while the depth adjustment aperture only allows for the passage of the lead in shaft 1029. Further to this example, the depth of the lead in 1009 engagement with a vessel can be controlled by the amount of the shaft and/or rod that is allowed to pass through them.

Figure 11A:
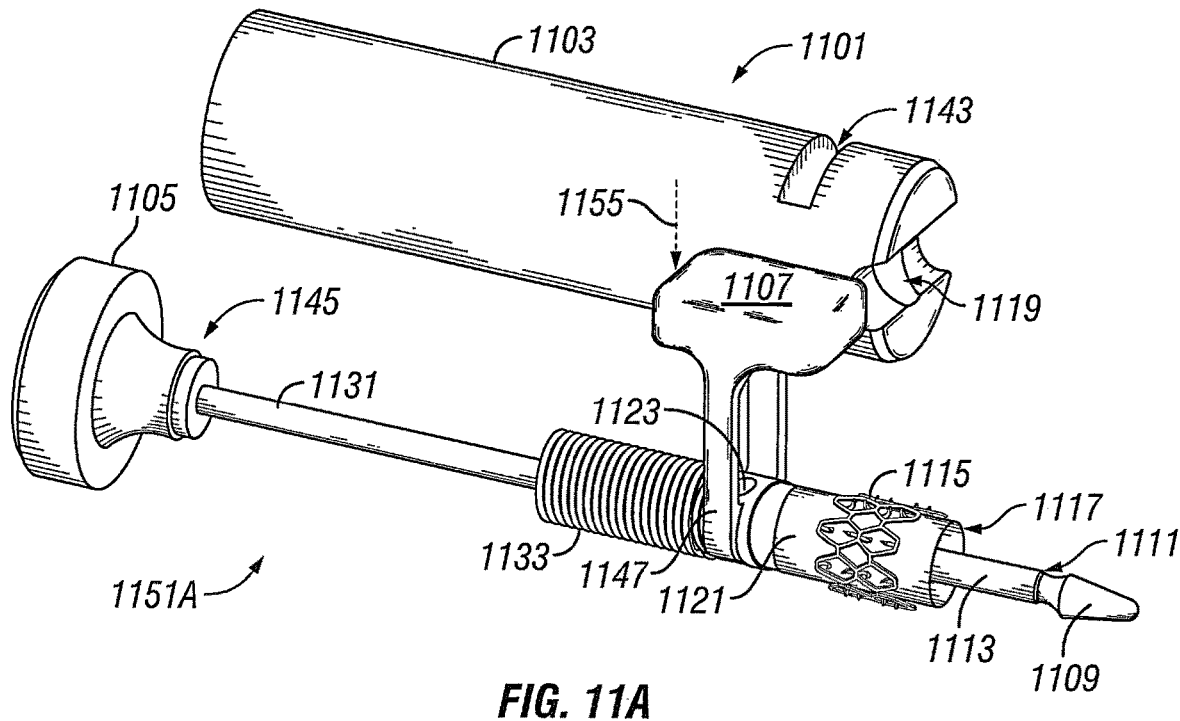
FIG. 11A is a partially exploded view illustration of a dual stent delivery tool in a pre-delivery state.

FIG. 11A is a partially exploded view illustration of a dual stent delivery tool 1101 in a pre-delivery state 1151A. In at least one embodiment, the dual stent delivery tool 1101 may be utilized to place two stents with a single button press, allowing for the first portion of an amitosis surgery to be completed in just a few seconds, rather than the current methods which can take up to ten to twenty minutes per vessel. In some examples, the dual stent delivery tool 1101 be included as part of a set of delivery tools or in sterilized blister packs that can be opened and utilized in rapid succession during intensive surgery. In at least one embodiment, the pre-delivery state 1151A is the state before a pressure or force 1155 is applied to a firing tab or button 1107. The pre-delivery state 1151A, in at least one example, is the state where the firing tab extensions 1147 are engaged with the cover carrier 1121.

The dual stent delivery tool 1101 can have a main body 1103 for housing the internal workings of the stent delivery tool 1101, and in at least one example, partially housing and/or containing one or more stents. In at least one embodiment, the main body 1103 can be cylindrical, with a first end having a back stop 1105, and a second end opposing the first end, and the second end having an opening to receive the one or more stents. In some examples, the main body 1103 may have additional openings, apertures, or other structures that pass through or along portions of the main body 1103. The back stop 1105 may be threaded, friction fit, or otherwise coupled to the main body 1103 in a manner that prevents it from being removed from the main body 1103 without additional outside forces. The main body 1103 may house all of the components with the exception of portions of the lead in 1109 and/or lead in shaft 1129, firing tab or button 1107, the back stop 1105, and/or depth adjustment 1135.

A firing tab or button 1107 may be utilized by a user or medical professional to activate the mechanisms to transfer one or both of the stents. It would be understood, that while one button is illustrated, in at least one example two or more buttons may be utilized to trigger the transfer and/or insertion of one or more stents and/or other activities related to these and similar procedures. The firing tab or button 1107 may include firing tab or button engagement extensions 1147 that can engage with the cover carrier 1121. In at least one example, the firing tab or button 1107 when pressed the firing tab extension 1147 passes through the cover carrier engagement aperture releasing the cover carrier 1121 to move. In some examples of the dual stent delivery tool 901, there may be additional firing tab(s) or button(s) 1107 to allow for vessels to be engaged or disengaged, along with the engagement or disengagement of one or more stents.

When the firing tab 1107 is pressed, a lead in 1109, in some examples called an olive tip lead in, can extend or retract based on the design of the dual stent delivery tool 1101. The lead in 1109 can be shaped like a rounded bullet with a tapered front end, coupled to a cylindrical section, and a tapered rear section that coupled to a plunger and/or rod. While the olive shape is illustrated, other shapes may be utilized without departing from the spirit of the present disclosure.

In at least one embodiment, the lead in 1109 can engage and/or interact with an inner stent 1111. In at least one example, the inner stent 1111 can be a modifiable stent that is capable of expanding and/or retracting on itself. In yet other examples, the inner stent 1111 may also have one or more anchor points that when engaged can allow the inner stent 1111 to be secured to a vessel (not illustrated). In at least one embodiment, an inner stent covering 1113 can compress and/or prevent the modification of the inner stent 1111 prior to the removal of the inner stent covering 1113. In some examples, the inner stent covering 1113 can be a flexible material with perforations that allow it to be ripped and/or removed in a quick movement without leaving any material behind. Similarly, the outer stent 1115 can be a modifiable stent that is capable of expanding and/or retracting on itself. In yet other examples, the inner stent 1115 may also have one or more anchor points that when engaged can allow the inner stent 1115 to be secured to a vessel (not illustrated). In at least one embodiment, an inner stent covering 1117 can compress and/or prevent the modification of the inner stent 1115 prior to the removal of the inner stent covering 1117. In some examples, the inner stent covering 1117 can be a flexible material with perforations that allow it to be ripped and/or removed in a quick movement without leaving any material behind. The inner stent 1111 can be co-axially related to the outer stent 1115 such that the inner stent 1111 is within the inner radius or diameter of the outer stent 1115.

The main body 1103 can include a body aperture 1119 that allows for access to the internal portions of the main body 1103. In at least one example, the body aperture 1119 is sized and/or configured to allow for the passage and/or storage of one or both stents, a plunger or rod, a firing mechanism (not illustrated), and/or the lead in 1109.

The cover carrier 1121, in some examples a sheath carrier can allow for a coupling to the one or more sheaths or coverings for the stents of the present disclosure. In at least one example, the covers or sheaths are coupled to the cover carrier 1121 in a manner that when the firing button or tab 1107 is pressed it releases the cover carrier 1121 to move and thereby moving the stent covers or sheaths as well. The cover carrier 1121 may also have a cover carrier engagement aperture that allows portions of the firing tab or button 1107, such as but not limited to firing tab or button extensions 1147 to pass through and/or interact with the cover carrier 1121. In some examples, the cover carrier engagement aperture may be formed in such a way that it must be positioned correctly in order to engage or interact with portion of the firing tab or button 1107, while in other examples, the cover carrier engagement aperture may have a consistent configuration around the entire perimeter of the cover carrier 1121. The cover carrier 1121, in at least one embodiment, can have a cover carrier retention zone. The cover carrier retention zone can be an area to receive a spring or other retention mechanism. In at least one embodiment, the cover carrier retention zone may also be able to engage with a pushing or acceleration mechanism that can push the cover carrier 1121 away from the back stop 1105. The cover carrier retention zone and/or the cover carrier engagement aperture can surround and/or device a cover carrier pass through void that allows a rod or plunger to pass through the cover carrier 1121.

The lead in 1109 can be coupled to a lead in shaft 1129. The lead in shaft 1129 can be a rod or plunger that passes through the body aperture 1119. In some examples, it can couple with a plunger rod 1131. In at least one example the plunger rod 1131 surrounds the lead in shaft 1129 to provide additional support. In other examples, the plunger rod 1131 can be an extension of the lead in shaft 1129.

In at least on embodiment, a retention mechanism 1133 can be utilized to engage the cover carrier 1121 backwards towards the back stop 1105 or forwards towards the body aperture 1119. In at least one example, the retention mechanism 1133 is a spring, while in other example, other forms of mechanism that can impart kinetic energy may be utilized. When the firing tab or button 1107 is engaged by the user and passes a portion of the firing tab or button through the main body firing tab aperture, the kinetic energy stored in the retention mechanism 1133 can be released.

The retention mechanism 1133 can be coupled between the cover carrier retention zone and the back stop retention zone. The back stop retention zone can be an area to receive a spring or other retention mechanism 1133. In at least one embodiment, the back stop retention zone may also be able to engage with a pushing or acceleration mechanism that can push the cover carrier 1121 away from the back stop 1105. The lead in 1109 interaction depth with a vessel (not illustrated) can be adjusted with a depth adjustment 1135. In at least one example, the depth adjustment 1135 interacts with the back stop 1105 though a threaded connection, while other connections that allow for changes of positioning between two elements would not depart from the spirit of the present disclosure. The threaded connection may be illustrated by a depth adjustment engagement surface along the outer perimeter of the depth adjustment 1135, and the inner perimeter of the back stop 1105.

The lead in shaft 1129 and/or plunger rod 1131 can pass through and/or engage with a back stop aperture defined by the back stop 1105 and/or the depth adjustment aperture defined by the depth adjustment 1135. In at least one example, the back stop aperture can allow for the passage of the lead in shaft 1129 and the plunger rod 1131 while the depth adjustment aperture only allows for the passage of the lead in shaft 1129. Further to this example, the depth of the lead in 1109 engagement with a vessel can be controlled by the amount of the shaft and/or rod that is allowed to pass through them.

Figure 11B:
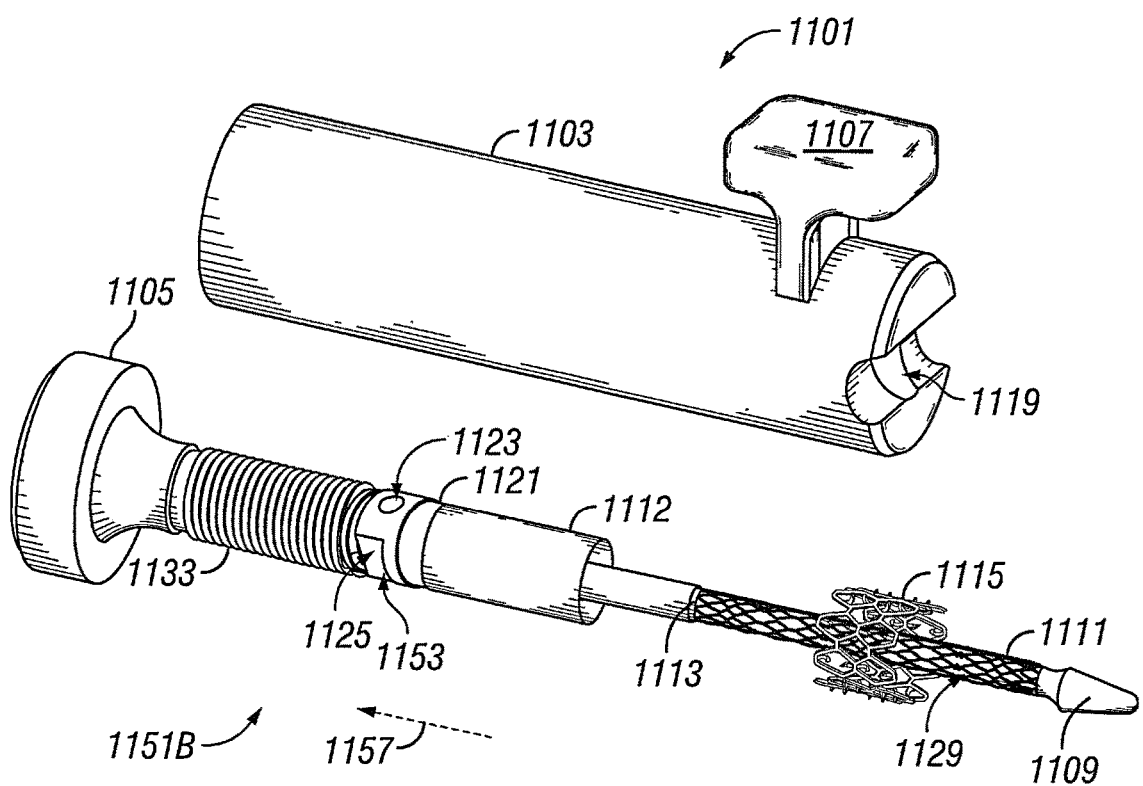
FIG. 11B is a partially exploded view illustration of a dual stent delivery tool in a delivered state.

FIG. 11B is a partially exploded view illustration of a dual stent delivery tool 1101 in a delivered state 1151B. In at least one embodiment, the dual stent delivery tool 1101 may be utilized to place two stents with a single button press, allowing for the first portion of an amitosis surgery to be completed in just a few seconds, rather than the current methods which can take up to ten to twenty minutes per vessel. In some examples, the dual stent delivery tool 1101 be included as part of a set of delivery tools or in sterilized blister packs that can be opened and utilized in rapid succession during intensive surgery. In at least one embodiment, the delivered state 1151B is the state after a pressure or force is applied to a firing tab or button 1107. The delivered state 1151B, in at least one example, is the state where the firing tab extensions 1147 are disengaged with the cover carrier 1121. Allowing for a movement 1157 to occur that allows the retention mechanism 1133 to be returned to a neutral state and allows the stent(s) to be delivered. When the retention mechanism 1133 returns to a neutral state the cover carrier 1121 moves with it causing the covers or sheaths of the stent(s) to be removed allowing them to be placed within and/or around a vessel.

The dual stent delivery tool 1101 can have a main body 1103 for housing the internal workings of the stent delivery tool 1101, and in at least one example, partially housing and/or containing one or more stents. In at least one embodiment, the main body 1103 can be cylindrical, with a first end having a back stop 1105, and a second end opposing the first end, and the second end having an opening to receive the one or more stents. In some examples, the main body 1103 may have additional openings, apertures, or other structures that pass through or along portions of the main body 1103. The back stop 1105 may be threaded, friction fit, or otherwise coupled to the main body 1103 in a manner that prevents it from being removed from the main body 1103 without additional outside forces. The main body 1103 may house all of the components with the exception of portions of the lead in 1109 and/or lead in shaft 1129, firing tab or button 1107, the back stop 1105, and/or depth adjustment 1135.

A firing tab or button 1107 may be utilized by a user or medical professional to activate the mechanisms to transfer one or both of the stents. It would be understood, that while one button is illustrated, in at least one example two or more buttons may be utilized to trigger the transfer and/or insertion of one or more stents and/or other activities related to these and similar procedures. The firing tab or button 1107 may include firing tab or button engagement extensions 1147 that can engage with the cover carrier 1121. In at least one example, the firing tab or button 1107 when pressed the firing tab extension 1147 passes through the cover carrier engagement aperture releasing the cover carrier 1121 to move. In some examples of the dual stent delivery tool 901, there may be additional firing tab(s) or button(s) 1107 to allow for vessels to be engaged or disengaged, along with the engagement or disengagement of one or more stents.

When the firing tab 1107 is pressed, a lead in 1109, in some examples called an olive tip lead in, can extend or retract based on the design of the dual stent delivery tool 1101. The lead in 1109 can be shaped like a rounded bullet with a tapered front end, coupled to a cylindrical section, and a tapered rear section that coupled to a plunger and/or rod. While the olive shape is illustrated, other shapes may be utilized without departing from the spirit of the present disclosure.

In at least one embodiment, the lead in 1109 can engage and/or interact with an inner stent 1111. In at least one example, the inner stent 1111 can be a modifiable stent that is capable of expanding and/or retracting on itself. In yet other examples, the inner stent 1111 may also have one or more anchor points that when engaged can allow the inner stent 1111 to be secured to a vessel (not illustrated). In at least one embodiment, an inner stent covering 1113 can compress and/or prevent the modification of the inner stent 1111 prior to the removal of the inner stent covering 1113. In some examples, the inner stent covering 1113 can be a flexible material with perforations that allow it to be ripped and/or removed in a quick movement without leaving any material behind. Similarly, the outer stent 1115 can be a modifiable stent that is capable of expanding and/or retracting on itself. In yet other examples, the inner stent 1115 may also have one or more anchor points that when engaged can allow the inner stent 1115 to be secured to a vessel (not illustrated). In at least one embodiment, an inner stent covering 1117 can compress and/or prevent the modification of the inner stent 1115 prior to the removal of the inner stent covering 1117. In some examples, the inner stent covering 1117 can be a flexible material with perforations that allow it to be ripped and/or removed in a quick movement without leaving any material behind. The inner stent 1111 can be co-axially related to the outer stent 1115 such that the inner stent 1111 is within the inner radius or diameter of the outer stent 1115.

The main body 1103 can include a body aperture 1119 that allows for access to the internal portions of the main body 1103. In at least one example, the body aperture 1119 is sized and/or configured to allow for the passage and/or storage of one or both stents, a plunger or rod, a firing mechanism (not illustrated), and/or the lead in 1109.

The cover carrier 1121, in some examples a sheath carrier can allow for a coupling to the one or more sheaths or coverings for the stents of the present disclosure. In at least one example, the covers or sheaths are coupled to the cover carrier 1121 in a manner that when the firing button or tab 1107 is pressed it releases the cover carrier 1121 to move and thereby moving the stent covers or sheaths as well. The cover carrier 1121 may also have a cover carrier engagement aperture that allows portions of the firing tab or button 1107, such as but not limited to firing tab or button extensions 1147 to pass through and/or interact with the cover carrier 1121. In some examples, the cover carrier engagement aperture may be formed in such a way that it must be positioned correctly in order to engage or interact with portion of the firing tab or button 1107, while in other examples, the cover carrier engagement aperture may have a consistent configuration around the entire perimeter of the cover carrier 1121. The cover carrier 1121, in at least one embodiment, can have a cover carrier retention zone. The cover carrier retention zone can be an area to receive a spring or other retention mechanism. In at least one embodiment, the cover carrier retention zone may also be able to engage with a pushing or acceleration mechanism that can push the cover carrier 1121 away from the back stop 1105. The cover carrier retention zone and/or the cover carrier engagement aperture can surround and/or device a cover carrier pass through void that allows a rod or plunger to pass through the cover carrier 1121.

The lead in 1109 can be coupled to a lead in shaft 1129. The lead in shaft 1129 can be a rod or plunger that passes through the body aperture 1119. In some examples, it can couple with a plunger rod 1131. In at least one example the plunger rod 1131 surrounds the lead in shaft 1129 to provide additional support. In other examples, the plunger rod 1131 can be an extension of the lead in shaft 1129.

In at least on embodiment, a retention mechanism 1133 can be utilized to engage the cover carrier 1121 backwards towards the back stop 1105 or forwards towards the body aperture 1119. In at least one example, the retention mechanism 1133 is a spring, while in other example, other forms of mechanism that can impart kinetic energy may be utilized. When the firing tab or button 1107 is engaged by the user and passes a portion of the firing tab or button through the main body firing tab aperture, the kinetic energy stored in the retention mechanism 1133 can be released.

The retention mechanism 1133 can be coupled between the cover carrier retention zone and the back stop retention zone. The back stop retention zone can be an area to receive a spring or other retention mechanism 1133. In at least one embodiment, the back stop retention zone may also be able to engage with a pushing or acceleration mechanism that can push the cover carrier 1121 away from the back stop 1105. The lead in 1109 interaction depth with a vessel (not illustrated) can be adjusted with a depth adjustment 1135. In at least one example, the depth adjustment 1135 interacts with the back stop 1105 though a threaded connection, while other connections that allow for changes of positioning between two elements would not depart from the spirit of the present disclosure. The threaded connection may be illustrated by a depth adjustment engagement surface along the outer perimeter of the depth adjustment 1135, and the inner perimeter of the back stop 1105.

The lead in shaft 1129 and/or plunger rod 1131 can pass through and/or engage with a back stop aperture defined by the back stop 1105 and/or the depth adjustment aperture defined by the depth adjustment 1135. In at least one example, the back stop aperture can allow for the passage of the lead in shaft 1129 and the plunger rod 1131 while the depth adjustment aperture only allows for the passage of the lead in shaft 1129. Further to this example, the depth of the lead in 1109 engagement with a vessel can be controlled by the amount of the shaft and/or rod that is allowed to pass through them.

Figure 12:
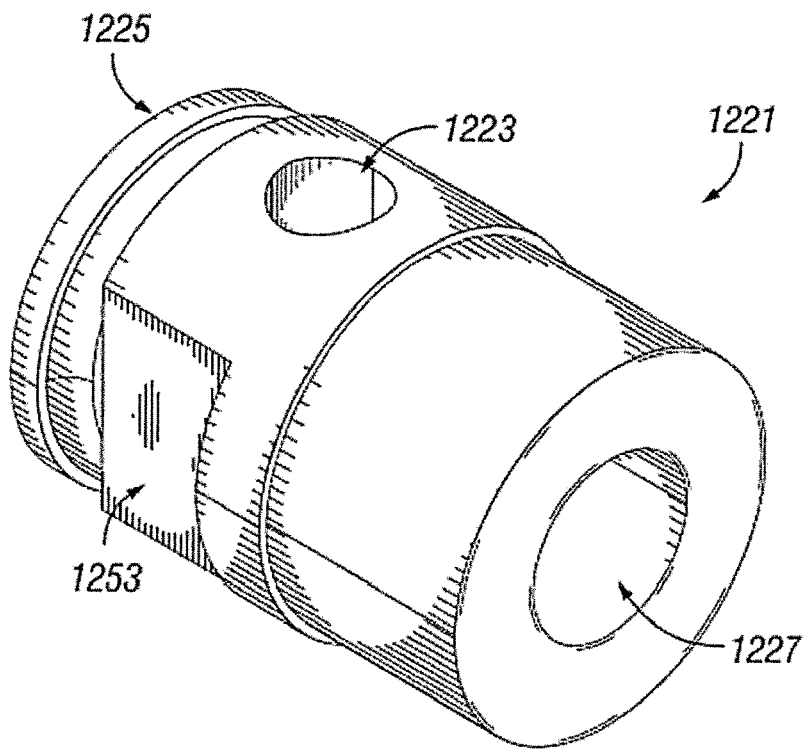
FIG. 12 is a perspective view illustration of a sheath or cover carrier.

FIG. 12 is a perspective view illustration of a sheath or cover carrier 1221. The cover carrier 1212 can be coupled to one or more covers or sheaths for one or more stents. These covers or sheaths can couple to any number of points of the cover carrier 1212. The cover carrier engagement aperture 1223 can allow for the positioning of the cover carrier 1221 within a stent delivery system or device. In at least one example, the cover carrier engagement aperture 1223 can be utilized to secure the cover carrier 1221 to a shaft or rod through a fastener, such as, but not limited to, a screw, bolt, or other securing mechanism. The cover carrier retention zone 1225 allows for retention mechanisms, springs, or other kinetic devices to be coupled to the cover carrier 1221. The cover carrier pass through void 1227, allows for shafts and/or rods to pass through the cover carrier 1221. A cover carrier engagement zone 1253 can be utilized to allow the cover carrier 1221 to engage with a firing tab or button. In at least one example, the cover carrier 1221 can be secured when the cover carrier engagement zone 1253 is engaged, and when released and the cover carrier engagement zone 1253 is not engaged the cover carrier 1221 is released to move based on the kinetic energy of a securing mechanism.

Figure 13:
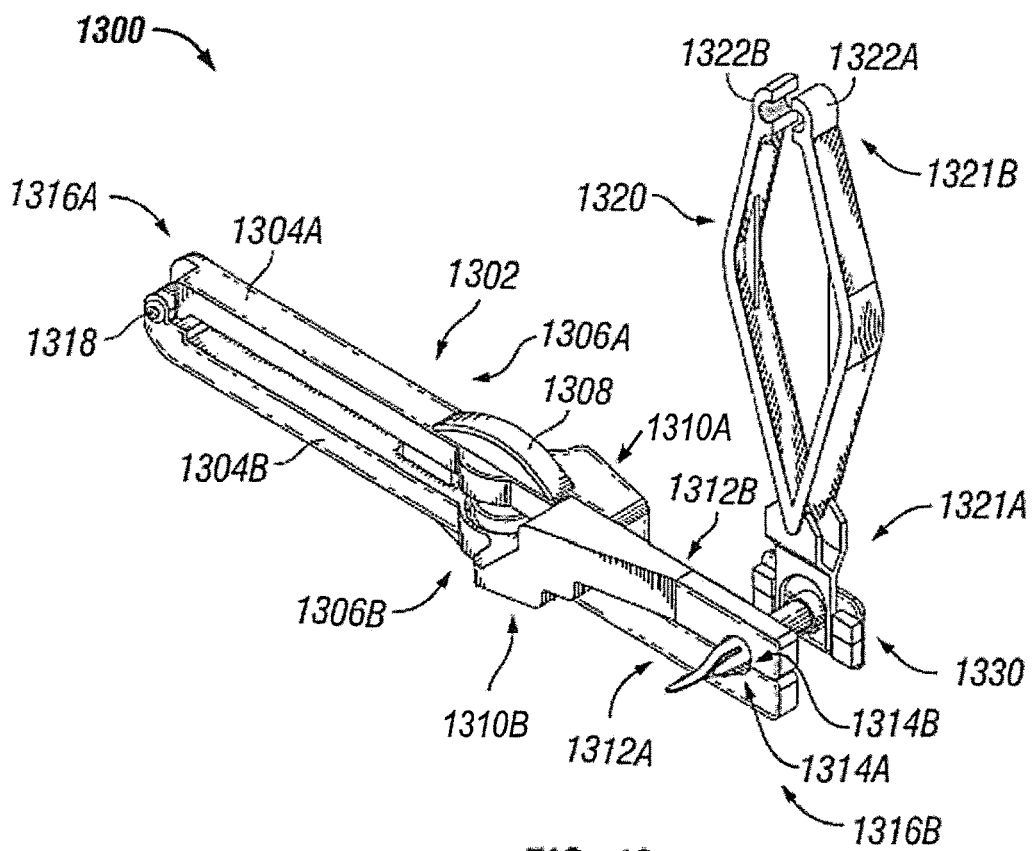
FIG. 13 is a perspective view illustration of a pull over tool assembly.

FIG. 13 is a perspective view illustration of a pull over tool assembly 1300. The pull over assembly 1300 can include an engagement tool 1302 and a pull tool 1320. The engagement tool 1302 may be used to engage with a vessel. In at least one embodiment, the engagement tool 1302 engages with a vessel to allow the vessel to be placed over a stent or set of stents. Additionally, in at least one example, the stent or set of stents may have another vessel engaged with it, allowing for the vessels to be joined together. The pull tool 1320 may be utilized to pull, shift, adjust, and/or otherwise engage the vessel with the engagement tool 1302. In at least one embodiment, the pull tool 1320 can have a set of tweezer arms 1322A/1322B at a second end 1321B of the pull tool 1320.

The engagement tool 1302 can have a first arm 1304A and a second arm 1304B (collectively engagement arms 1304). The engagement arms 1304 can have three sections, a user engagement section 1306A/1306B, where these sections may include a surface structure or texture 1308 that allows for a user to more easily control the engagement tool 1302. The engagement arms 1304 may also have crossover sections 1310A/1310B (collectively crossover sections 1310). The crossover sections 1310 can be utilized to allow for the engagement tool 1302 to be in a normally closed position. For example, a set of tweezers are in a normally open position, meaning the far end of the tweezers is open, or the ends of the arms are separated by a specified distance. To allow for a normally closed position, a reversal of the normally separated ends would be needed. This is achieved with the crossover sections 1310. The crossover sections 1310 can be coupled to the reversed sections 1312A/1312B (collectively the reversed sections 1312). The reversed sections 1312 allow for a set of engagement surfaces 1314A/1314B (collectively 1314 on each of the respective reversed sections 1312). The engagement surfaces 1314 can engage with a vessel guide 1330. In at least one example, the engagement tool 1302 has a first end 1316A (may also be referenced as a proximal end) with a hinge point 1318. In some examples, the hinge point 1318 may include a hinge pin, bolt, screw, nut, and/or other combination of a component that allows for rotation about it, and a structure to receive the component. These may be on either first end 1316A or be a separate element that engages with the first end 1316A. The first end 1316A can be coupled to the user engagement sections 1306. The user engagement sections 1306 may be coupled to the crossover sections 1310, and the crossover sections 1310 can be coupled to the reversed sections 1312. The reversed sections 1312 and/or engagement surfaces 1314 can be found at the second end 1316B (may be referenced as a distal end) of the engagement tool.

The engagement tool 1302 engages with a vessel guide 1330 which can be engaged by a pull tool 1320. The pull tool 1320 allows engagement of a vessel with the vessel guide 1330. The pull tool 1320 can have a first end 1321A and a second end 1321B, with each being distal from the other. The first end 1321A of the pull tool 1320 may be utilized to engage a vessel guide 1330. The vessel guide 1330 can be utilized to guide and/or open a first vessel to allow a second vessel to be received within it. In at least one example, these vessels may be referred to as donor and/or recipient vessels. The first end 1321A of the pull tool 1320 can be utilized to position the vessel guide 1330 through the use of a structured design where the first end 1321A has a male portion and the vessel guide 1330 has a female portion. It would be understood that these portions could be exchanged, meaning the male portion may be on the vessel guide 1330 and the first end 1321A having the female portion. Similarly, the male portion is designed to be inserted into the female portion. For example, the male portion may have two points separated by a U-shaped arch that engages with two apertures that allow for the points to be received by the female portion.

Figure 14:
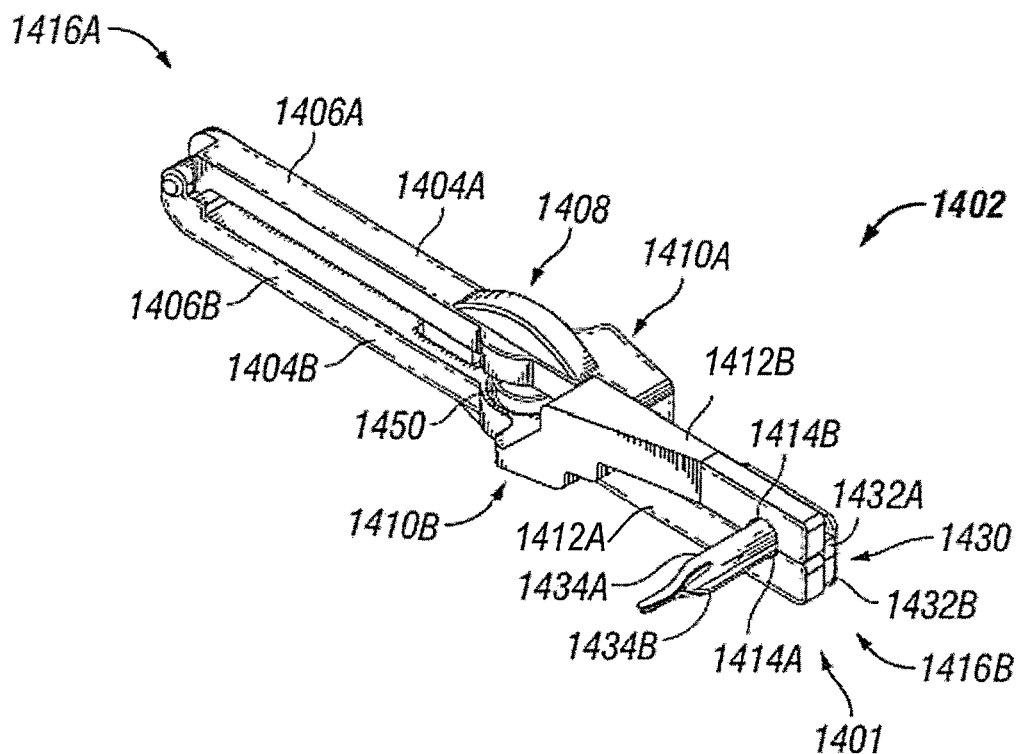
FIG. 14 is a perspective view illustration of an engagement tool in a normally closed state.

FIG. 14 is a perspective view illustration of an engagement tool 1402 in a normally closed state 1401. The engagement tool 1402 can have a first arm 1404A and a second arm 1404B (collectively engagement arms 1404). The engagement arms 1404 can have three sections, one being a user engagement section 1406A/1406B, where this section may include a surface structure or texture 1408 that allows for a user to more easily control the engagement tool 1402. The engagement arms 1404 may also have crossover section 1410A/1410B (collectively crossover sections 1410). The crossover sections 1410 can be utilized to allow for the engagement tool 1402 to be in a normally closed position. For example, a set of tweezers are in a normally open position, meaning the far end of the tweezers is open, or the ends of the arms are separated by a specified distance. To allow for a normally closed position, a reversal of the normally separated ends would be needed. This is achieved with the crossover sections 1410. The crossover sections 1410 can be coupled to the reversed section 1412A/1412B (collectively the reversed sections 1412). The reversed sections 1412 allow for a set of engagement surfaces 1414A/1414B (collectively 1414 on each of the respective reversed sections 1412). The engagement surfaces 1414 can engage with a vessel guide 1430. In at least one example, the engagement tool 1402 has a first end 1416A (may also be referenced as a proximal end) with a hinge point 1418. In some examples, the hinge point 1418 may include a hinge pin, bolt, screw, nut, and/or other combination of a component that allows for rotation about it, and a structure to receive the component. These may be on either first end 1416A or be a separate element that engages with the first end 1416A. The first end 1416A can be coupled to the user engagement sections 1406. The user engagement sections 1406 may be coupled to the crossover sections 1410, and the crossover sections 1410 can be coupled to the reversed sections 1412. The reversed sections 1412 and/or engagement surfaces 1414 can be found at the second end 1416B (may be referenced as a distal end) of the engagement tool.

The engagement tool 1402 engages with a vessel guide 1430 which can be engaged by a pull tool (illustrated in FIG. 13 as 1320). The vessel guide 1430, in at least one embodiment, may be split to allow for vessel engagement with a first guide (may be referenced as an upper guide) 1432A and a second guide (may be referenced as a lower guide) 1432B (collectively vessel guide 1430). Each of the two guides 1432A/1432B can have a forward section 1434A/1434B (may be referenced as a first or upper forward section 1434A, or a second or lower forward section 1434B, collectively forward sections 1434). The forward sections 1434 can taper to a point or rounded that allow for ease of insertion into a vessel. The taper also provides an ease of insertion as it provides a ramp or slope so that a vessel can be moved as far towards the engagement tool 1402 as possible. The engagement tool 1402 can also have a biasing mechanism 1450. The biasing mechanism 1450, in at least one embodiment, can be a spring, tensioned metal, tensioned plastic, or other mechanism or combination of mechanism that when compress apply a force opposite of the compression force. The biasing mechanism 1450 can be placed between the first arm 1404A and the second arm 1404B, and in at least one example is placed between the crossover sections 1410.

Figure 15:
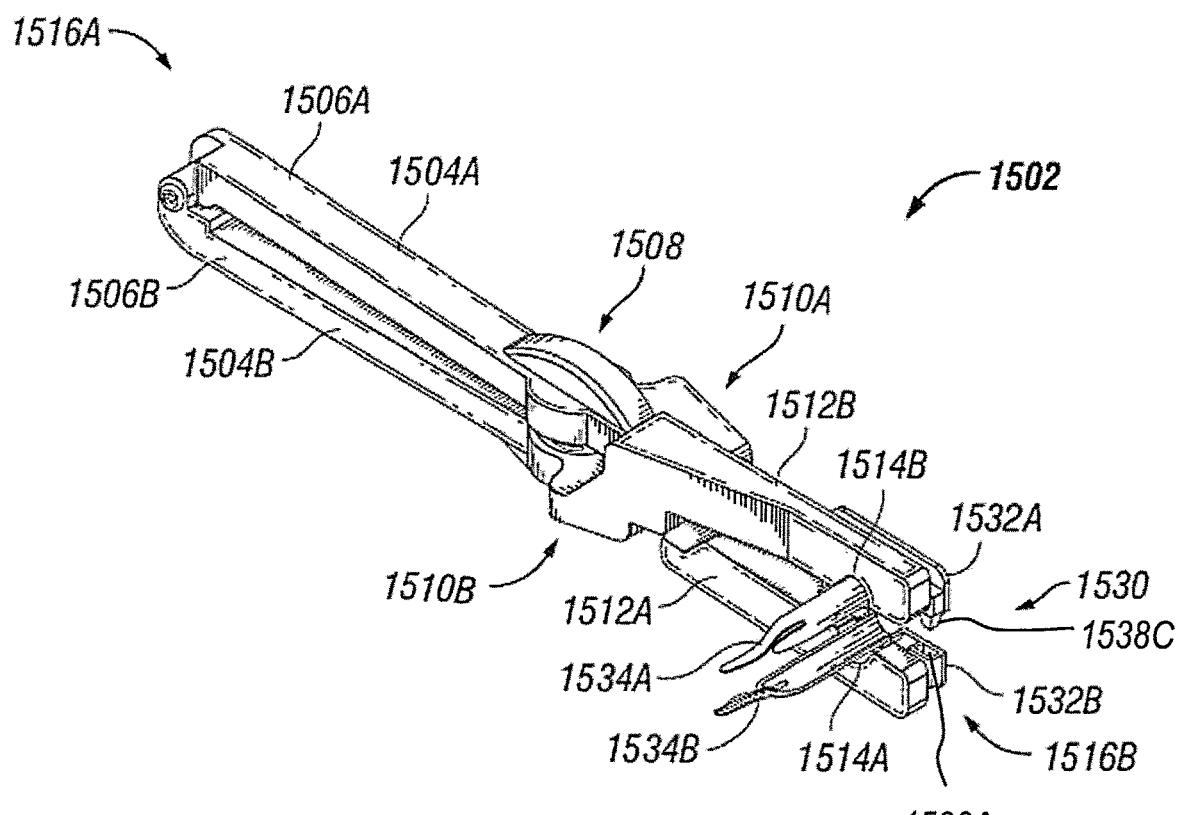
FIG. 15 is a perspective view illustration of an engagement tool in an open state.

FIG. 15 is a perspective view illustration of an engagement tool 1502 in an open state 1503. The engagement tool 1502 can have a first arm 1504A and a second arm 1504B (collectively engagement arms 1504). The engagement arms 1504 can have three sections, one being a user engagement section 1506A/1506B, where this section may include a surface structure or texture 1508 that allows for a user to more easily control the engagement tool 1502. The engagement arms 1504 may also have crossover section 1510A/1510B (collectively crossover sections 1510). The crossover sections 1510 can be utilized to allow for the engagement tool 1502 to be in a normally closed position. For example, a set of tweezers are in a normally open position, meaning the far end of the tweezers is open, or the ends of the arms are separated by a specified distance. To allow for a normally closed position, a reversal of the normally separated ends would be needed. This is achieved with the crossover sections 1510. The crossover sections 1510 can be coupled to the reversed section 1512A/1512B (collectively the reversed sections 1512). The reversed sections 1512 allow for a set of engagement surfaces 1514A/1514B (collectively 1514 on each of the respective reversed sections 1512). The engagement surfaces 1514 can engage with a vessel guide 1530. In at least one example, the engagement tool 1502 has a first end 1516A (may also be referenced as a proximal end) with a hinge point 1518. In some examples, the hinge point 1518 may include a hinge pin, bolt, screw, nut, and/or other combination of a component that allows for rotation about it, and a structure to receive the component. These may be on either first end 1516A or be a separate element that engages with the first end 1516A. The first end 1516A can be coupled to the user engagement sections 1506. The user engagement sections 1506 may be coupled to the crossover sections 1510, and the crossover sections 1510 can be coupled to the reversed sections 1512. The reversed sections 1512 and/or engagement surfaces 1514 can be found at the second end 1516B (may be referenced as a distal end) of the engagement tool.

The engagement tool 1502 engages with a vessel guide 1530 which can be engaged by a pull tool (illustrated in FIG. 13 as 1320). The vessel guide 1530, in at least one embodiment, may be split to allow for vessel engagement with a first guide (may be referenced as an upper guide) 1532A and a second guide (may be referenced as a lower guide) 1532B (collectively vessel guide 1530). Each of the two guides 1532A/1532B can have a forward section 1534A/1534B (may be referenced as a first or upper forward section 1534A, or a second or lower forward section 1534B, collectively forward sections 1534). The forward sections 1534 can taper to a point or rounded that allow for ease of insertion into a vessel. The taper also provides an ease of insertion as it provides a ramp or slope so that a vessel can be moved as far towards the engagement tool 1502 as possible. The engagement tool 1502 can also be a biasing mechanism 1550. The biasing mechanism 1550, in at least one embodiment, can be a spring, tensioned metal, tensioned plastic, or other mechanism or combination of mechanism that when compress apply a force opposite of the compression force. The biasing mechanism 1550 can be placed between the first arm 1504A and the second arm 1504B, and in at least one example is placed between the crossover sections 1510.

The biasing mechanism 1550 can be compressed when a force 1552 is applied to one or both of the engagement arms 1504. As the force 1552 is applied to one or both of the engagement arms 1504, it causes the biasing mechanism 1550 to compress and open the engagement sections 1514 at the second end 1516B of the engagement tool 1502. If the vessel guide 1530 is engaged with the second end 1516B of the engagement tool 1502, the upper guide 1532A and the lower guide 1532B may also open. The lower guide 1532B (a similar or opposing portion would be present on the upper guide 1532A as well but is unseen in this figure), may have an engagement groove and a set of receiving apertures 1538A that can receive a portion of a pull tool (not illustrated), and a guide or positioning pin 1538C that can be received by one of the set of receiving apertures 1538A.

Figure 16:
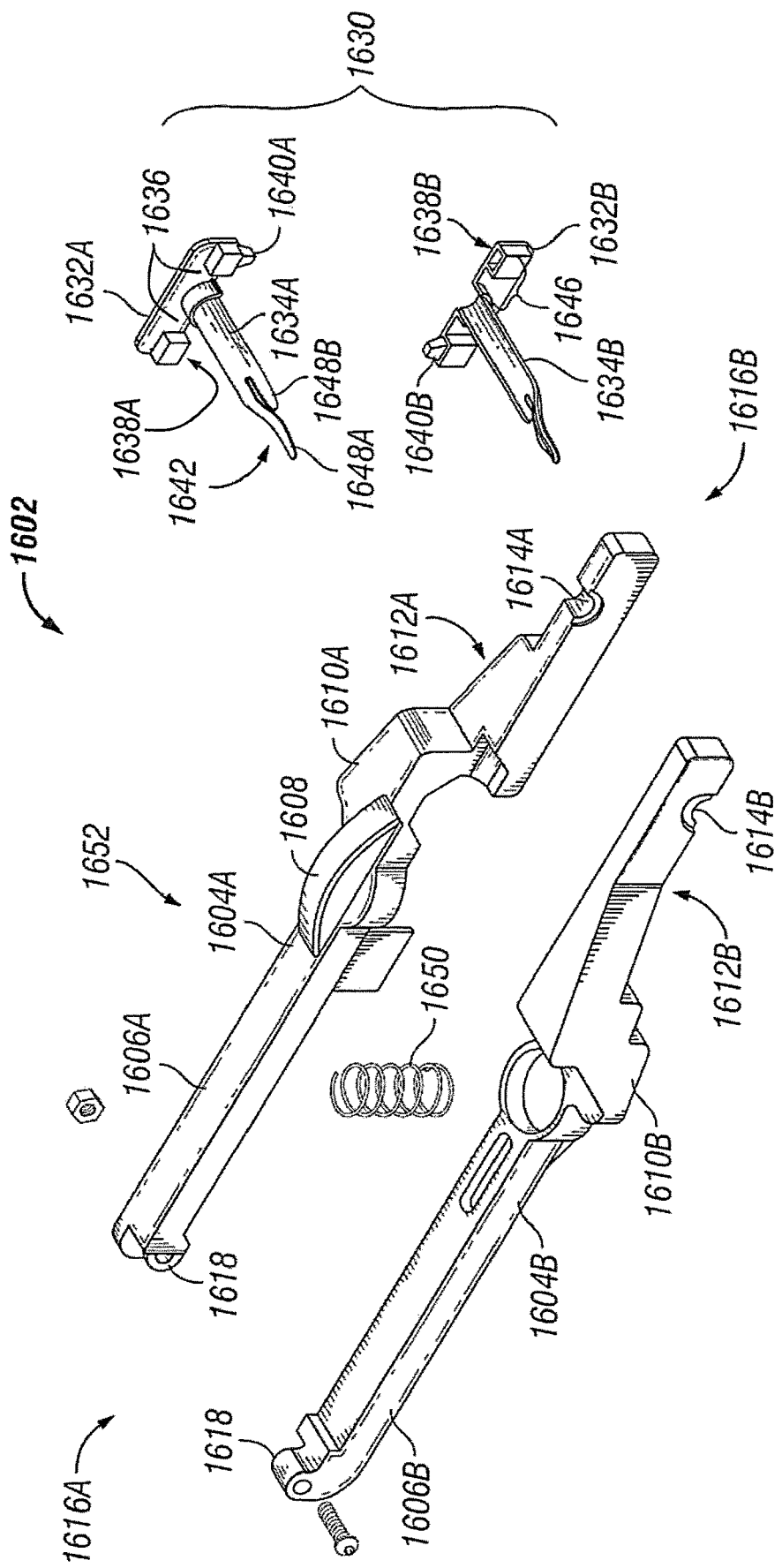
FIG. 16 is an exploded view illustration of an engagement tool.

FIG. 16 is an exploded view illustration of an engagement tool 1602. The engagement tool 1602 can have a first arm 1604A and a second arm 1604B (collectively engagement arms 1604). The engagement arms 1604 can have three sections, one being a user engagement section 1606A/1606B, where this section may include a surface structure or texture 1608 that allows for a user to more easily control the engagement tool 1602. The engagement arms 1604 may also have crossover section 1610A/1610B (collectively crossover sections 1610). The crossover sections 1610 can be utilized to allow for the engagement tool 1602 to be in a normally closed position. For example, a set of tweezers is in a normally open position, this means the far end of the tweezers is open, or the ends of the arms are separated by a specified distance. To allow for a normally closed position, a reversal of the normally separated ends would be needed. This is achieved with the crossover sections 1610. The crossover sections 1610 can be coupled to the reversed section 1612A/1612B (collectively the reversed sections 1612). The reversed sections 1612 allow for a set of engagement surfaces 1614A/1614B (collectively 1614 on each of the respective reversed sections 1612). The engagement surfaces 1614 can engage with a vessel guide 1630. In at least one example, the engagement tool 1602 has a first end 1616A (may also be referenced as a proximal end) with a hinge point 1618. In some examples, the hinge point 1618 may include a hinge pin, bolt, screw, nut, and/or other combination of a component that allows for rotation about it, and a structure to receive the component. These may be on either first end 1616A or be a separate element that engages with the first end 1616A. The first end 1616A can be coupled to the user engagement sections 1606. The user engagement sections 1606 may be coupled to the crossover sections 1610, and the crossover sections 1610 can be coupled to the reversed sections 1612. The reversed sections 1612 and/or engagement surfaces 1614 can be found at the second end 1616B (may be referenced as a distal end) of the engagement tool.

The engagement tool 1602 engages with a vessel guide 1630 which can be engaged by a pull tool (illustrated in FIG. 13 as 1320). The vessel guide 1630, in at least one embodiment, may be split to allow for vessel engagement with a first guide (may be referenced as an upper guide) 1632A and a second guide (may be referenced as a lower guide) 1632B (collectively vessel guide 1630). Each of the two guides 1632A/1632B can have a forward section 1634A/1634B (may be referenced as a first or upper forward section 1634A, or a second or lower forward section 1634B, collectively forward sections 1634). The forward sections 1634 can taper to a point or rounded that allow for ease of insertion into a vessel. The taper also provides an ease of insertion as it provides a ramp or slope so that a vessel can be moved as far towards the engagement tool 1602 as possible. The engagement tool 1602 can also have a biasing mechanism 1650. The biasing mechanism 1650, in at least one embodiment, can be a spring, tensioned metal, tensioned plastic, or other mechanism or combination of mechanism that when compress apply a force opposite of the compression force. The biasing mechanism 1650 can be placed between the first arm 1604A and the second arm 1604B, and in at least one example is placed between the crossover sections 1610.

The biasing mechanism 1650 can be compressed when a force 1652 is applied to one or both of the engagement arms 1604. As the force 1652 is applied to one or both of the engagement arms 1604 it cases the biasing mechanism 1650 to compress and open the engagement sections 1614 at the second end 1616B of the engagement tool 1602. If the vessel guide 1630 is engaged with the second end 1616B of the engagement tool 1602, the upper guide 1632A and the lower guide 1632B may also open. The lower guide 1632B (a similar or opposing portion would be present on the upper guide 1632A as well but is unseen in this figure), may have an engagement groove 1636, and a set of receiving apertures 1638A/1638B that can receive a portion of a pull tool (not illustrated), and a guide or positioning pin 1638C that can be received by one of the set of receiving apertures 1638A/1638B. The receiving apertures 1638A/1638B may be utilized to guide a pull tool (not illustrated). In at least one embodiment, the receiving aperture 1638A can be open on a first end, and define a receiving void that is closed on all sides at a second end. The receiving aperture 1638B may also receive an alignment point 1640A, while an alignment point 1640B may be received on a receiving aperture 1638A of the upper guide 1632A. The receiving aperture 1638B may define an engagement void that is open on each end and at least one side. The receiving aperture 1638B can be used for engagement by a pull tool (not illustrated).

The upper guide 1632A, and lower guide 1632B, may have an engagement section 1642 that allows for engagement of the guide 1632 with one or more vessels. In at least one example, the engagement section 1642 can have an elongated portion 1634A/1634B that is coupled to the alignment section 1636/1646. The alignment section 1636/1646 can include the receiving apertures 1638A/1638B, and alignment points 1640A/1640B. The engagement section 1642 can have a tubular structure that connects to a set of fingers 1648A/1648B. The first finger 1648A can be extended longer than the second finger 1648B. The second finger 1648B may have a mirror version that is unseen in the view presented. The first finger 1648A may have an angle and secondary flat section that can engage with a similar set of fingers on a lower guide 1632B. The secondary flat section can allow for a vessel to be guided onto the guides 1632.

Figure 17:
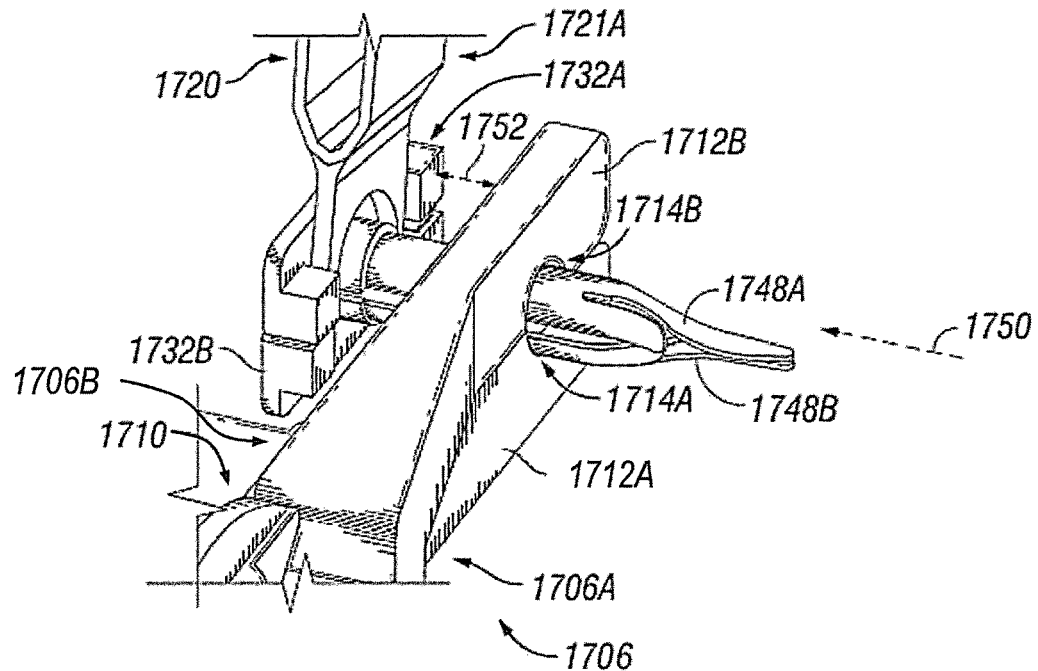
FIG. 17 is a perspective view of a pull over tool assembly showing the first end of the pull tool.

FIG. 17 is a perspective view of a pull over tool assembly 1700 viewing the first end 1721A of the pull tool 1720. The pull tool 1720 is engaged in a receiving aperture of the upper guide 1732A and lower guide 1732B (collectively guides 1732). The pull over tool assembly 1700 is illustrated in a normally closed state where the crossover section(s) 1710 and reversed section(s) 1712A/1712B (collectively the reversed sections 1712) allow for the guides 1732 to be utilized to engage with vessels. The crossover sections 1710 can be coupled to the reversed sections 1712. The reversed sections 1712 allow for a set of engagement surfaces 1714A/1714B (collectively 1714 on each of the respective reversed sections 1712). When a vessel (not illustrated) is pulled with an application of force 1750 it can slide over the finger(s) 1748A and/or 1748B. With the force 1750, a vessel may be pulled onto the tubular structure of the guides 1732. A separation space 1752 can be closed when the pull tool 1720 is utilized to push the guides 1732 into position with the arms 1706A/1706B.

Figure 18:
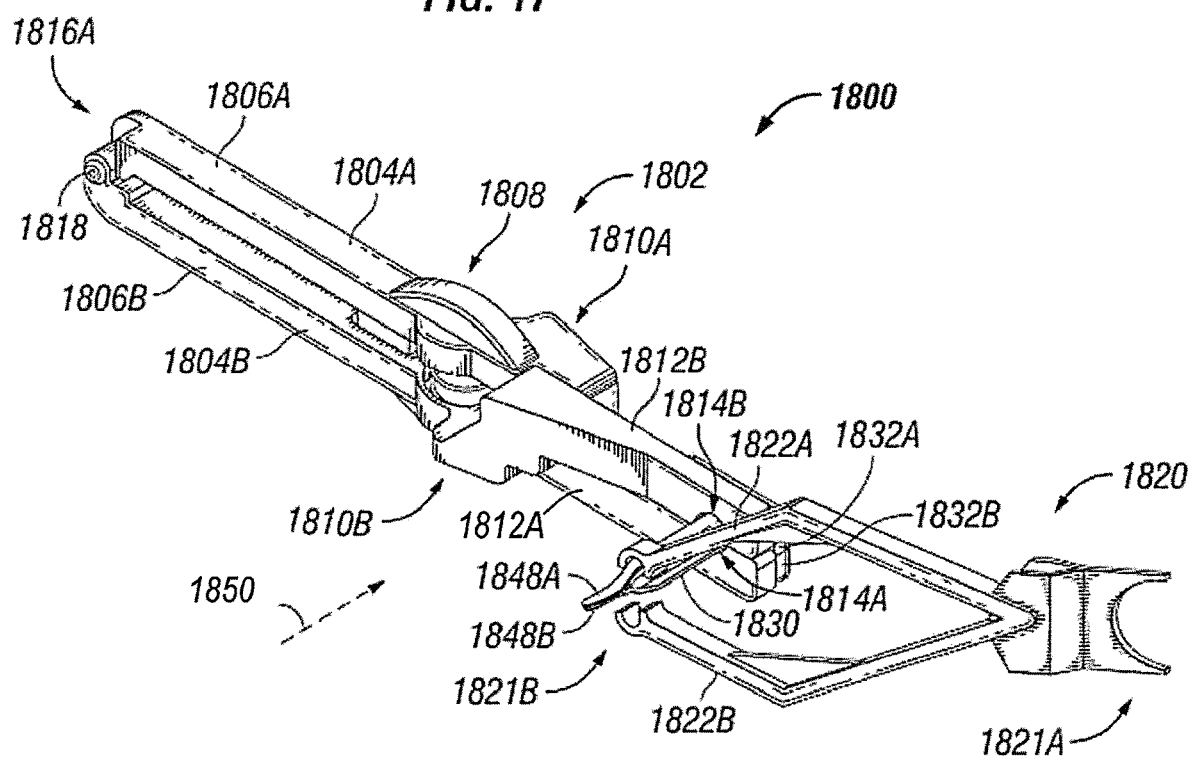
FIG. 18 is a perspective view illustration of the pull over tool assembly in use-based configuration with the pull tool prepared to engage a vessel (not illustrated).

FIG. 18 is a perspective view illustration of the pull over tool assembly 1800 in use-based configuration with the pull tool 1820 prepared to engage a vessel (not illustrated). The pull over assembly 1800 can include an engagement tool 1802 and a pull tool 1820. The engagement tool 1802 may be used to engage with a vessel. In at least one embodiment, the engagement tool 1802 engages with a vessel to allow the vessel to be placed over a stent or set of stents. Additionally, in at least one example, the stent or set of stents may have another vessel engaged with it, allowing for the vessels to be joined together. The pull tool 1820 may be utilized to pull, shift, adjust, and/or otherwise engage the vessel with the engagement tool 1802. In at least one embodiment, the pull tool 1820 can have a set of tweezer arms 1822A/1822B at a second end 1821B of the pull tool 1820.

The engagement tool 1802 can have a first arm 1804A and a second arm 1804B (collectively engagement arms 1804). The engagement arms 1804 can have three sections, one being a user engagement section 1806A/1806B, where this section may include a surface structure or texture 1808 that allows for a user to more easily control the engagement tool

1802. The engagement arms 1804 may also have crossover section 1810A/1810B (collectively crossover sections 1810). The crossover sections 1810 can be utilized to allow for the engagement tool 1802 to be in a normally closed position. For example, a set of tweezers are in a normally open position, meaning the far end of the tweezers is open, or the ends of the arms are separated by a specified distance. To allow for a normally closed position, a reversal of the normally separated ends would be needed. This is achieved with the crossover sections 1810. The crossover sections 1810 can be coupled to the reversed section 1812A/1812B (collectively the reversed sections 1812). The reversed sections 1812 allow for a set of engagement surfaces 1814A/1814B (collectively 1814 on each of the respective reversed sections 1812). The engagement surfaces 1814 can engage with a vessel guide 1830. In at least one example, the engagement tool 1802 has a first end 1816A (may also be referenced as a proximal end) with a hinge point 1818. In some examples, the hinge point 1818 may include a hinge pin, bolt, screw, nut, and/or other combination of a component that allows for rotation about it, and a structure to receive the component. These may be on either first end 1816A or be a separate element that engages with the first end 1816A. The first end 1816A can be coupled to the user engagement sections 1806. The user engagement sections 1806 may be coupled to the crossover sections 1810, and the crossover sections 1810 can be coupled to the reversed sections 1812. The reversed sections 1812 and/or engagement surfaces 1814 can be found at the second end 1816B (may be referenced as a distal end) of the engagement tool.

The engagement tool 1802 engages with a vessel guide 1830 which can be engaged by a pull tool 1820. The pull tool 1820 allows engagement of a vessel with the vessel guide 1830. The pull tool 1820 can have a first end 1821A and a second end 1821B, with each being distal from the other. The first end 1821A of the pull tool 1820 may be utilized to engage a vessel guide 1830. The vessel guide 1830 can be utilized to guide and/or open a first vessel to allow a second vessel to be received within it. In at least one example, these vessels may be referred to as donor and/or recipient vessels. The first end 1821A of the pull tool 1820 can be utilized to position the vessel guide 1830 through the use of a structured design where the first end 1821A has a male portion and the vessel guide 1830 has a female portion. It would be understood that these portions could be exchanged, meaning the male portion may be on the vessel guide 1830 and the first end 1821A having the female portion. Similarly, the male portion is designed to be inserted into the female portion. For example, the male portion may have two points separated by a U-shaped arch that engages with two apertures that allow for the points to be received by the female portion.

The pull tool 1820 is engaged in a receiving aperture of the upper guide 1832A and lower guide 1832B. The pull over tool assembly 1800 is illustrated in a normally closed state where the crossover section(s) 1810 and reversed section(s) 1812 allow for the guides 1832 to be utilized to engage with vessels. When a vessel (not illustrated) is pulled with an application of force 1850, it can slide over the finger(s) 1848A and/or 1848B. With the force 1850, a vessel may be pulled onto the tubular structure of the guides 1832. A separation space (illustrated as 1752 in FIG. 17) can be closed when the pull tool 1820 is utilized to push the guides 1832 into position with the arms 1806A/1806B.

Figure 19:
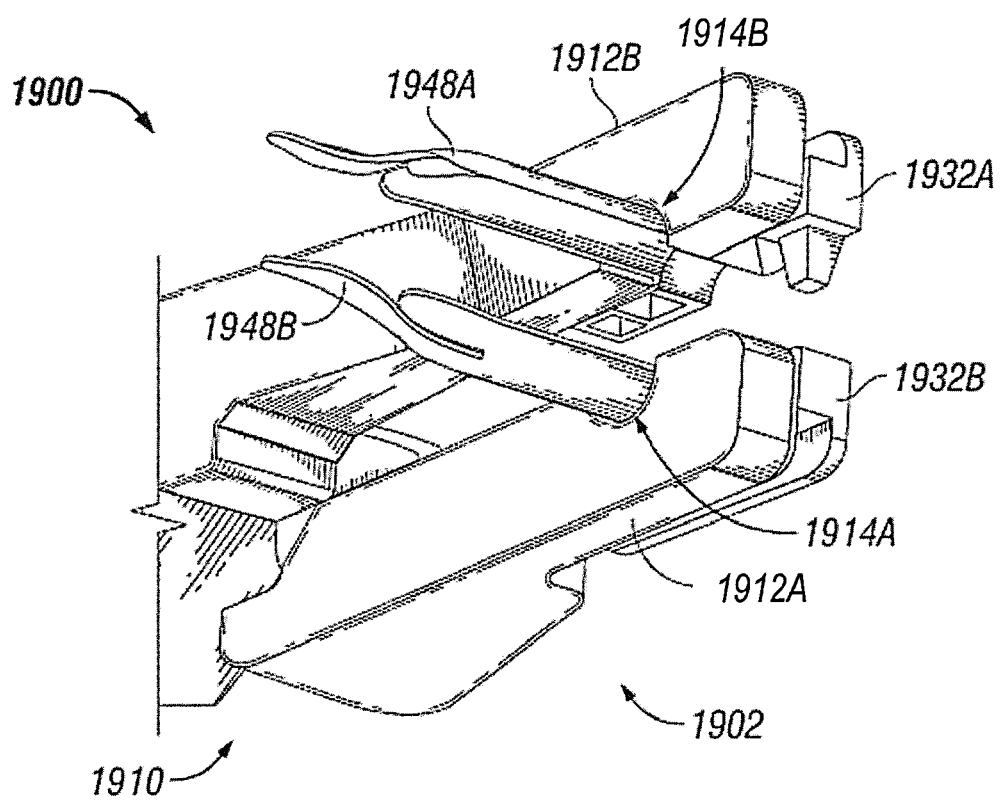
FIG. 19 is a perspective view of a pull over tool assembly without a pull tool (not illustrated).

FIG. 19 is a perspective view of a pull over tool assembly 1900 without a pull tool (not illustrated). The pull tool (not illustrated) may engage in a receiving aperture of the upper guide 1932A and lower guide 1932B (collectively the guides 1932). The pull over tool assembly 1900 is illustrated in an open state where the crossover section(s) 1910 and reversed section(s) 1912 allow for the guides 1932 to be utilized to engage with vessels. The crossover sections 1910 can be coupled to the reversed section 1912A/1912B (collectively the reversed sections 1912). The reversed sections 1912 allow for a set of engagement surfaces 1914A/1914B (collectively the engagement surfaces 1914 on each of the respective reversed sections 1912). When a vessel (not illustrated) is pulled with an application of force, it can slide over the finger(s) 1948A and/or 1948B. With the force, a vessel may be pulled onto the tubular structure of the guides 1932.

Figure 20:
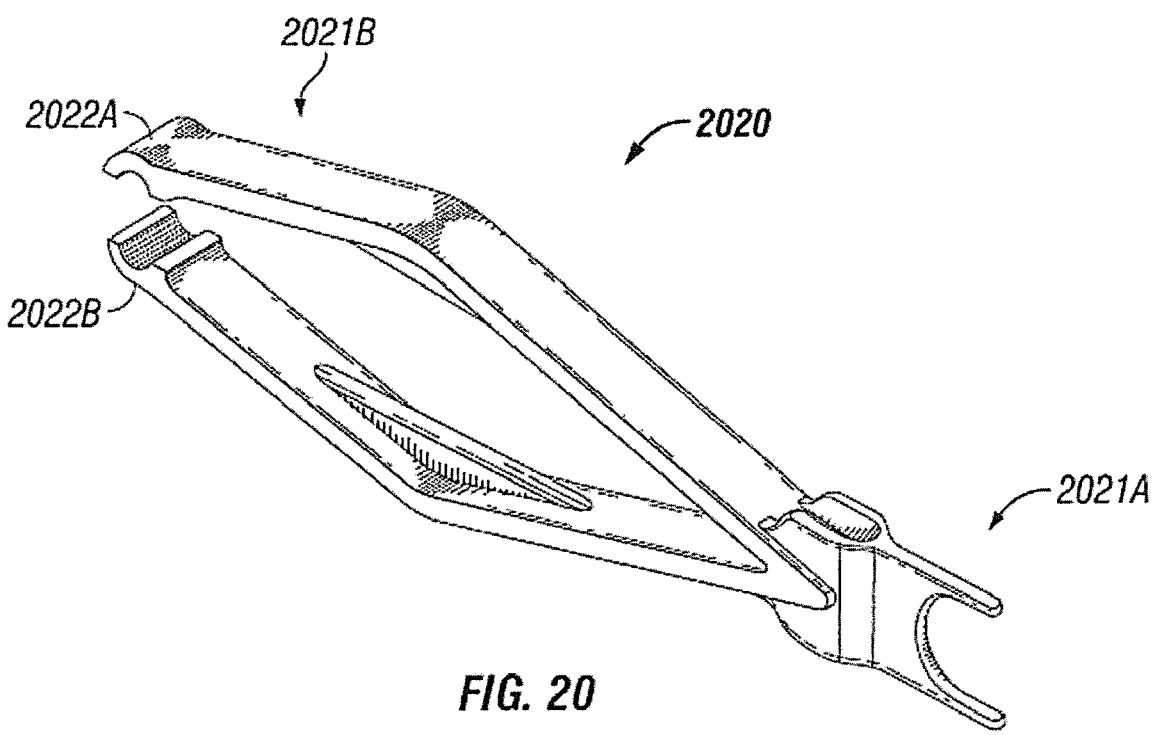
FIG. 20 is an illustration of the pull tool.

FIG. 20 is an illustration of the pull tool 2020. The pull tool 2020 may be utilized to pull, shift, adjust, and/or otherwise engage the vessel with the engagement tool (not illustrated). The pull tool 2020 can have a first end 2021A and a second end 2021, with each being distal from the other. The first end 2021A of the pull tool 2020 may be utilized to engage a vessel guide (not illustrated). The first end 2021A of the pull tool 2020 can be utilized to position the vessel guide (not illustrated) through the use of a structured design where the first end 2021A has a male portion and the vessel guide (not illustrated) has a female portion. It would be understood that these portions could be exchanged, meaning the male portion may be on the vessel guide (not illustrated) and the first end 2021A may have the female portion. Similarly, the male portion is designed to be inserted into the female portion. For example, the male portion may have two points separated by a U-shaped arch that engages with two apertures that allow for the points to be received by the female portion.

In at least one embodiment, the pull tool 2020 can have a set of tweezer arms 2022A/2022B at a second end 2021B of the pull tool 2020. The tweezer arms 2022A/2022B may include a surface structure 2028 In at least one example, the surface structure 2028 can have one or more points or raised surfaces that allow for gripping of an object.

Figure 21:
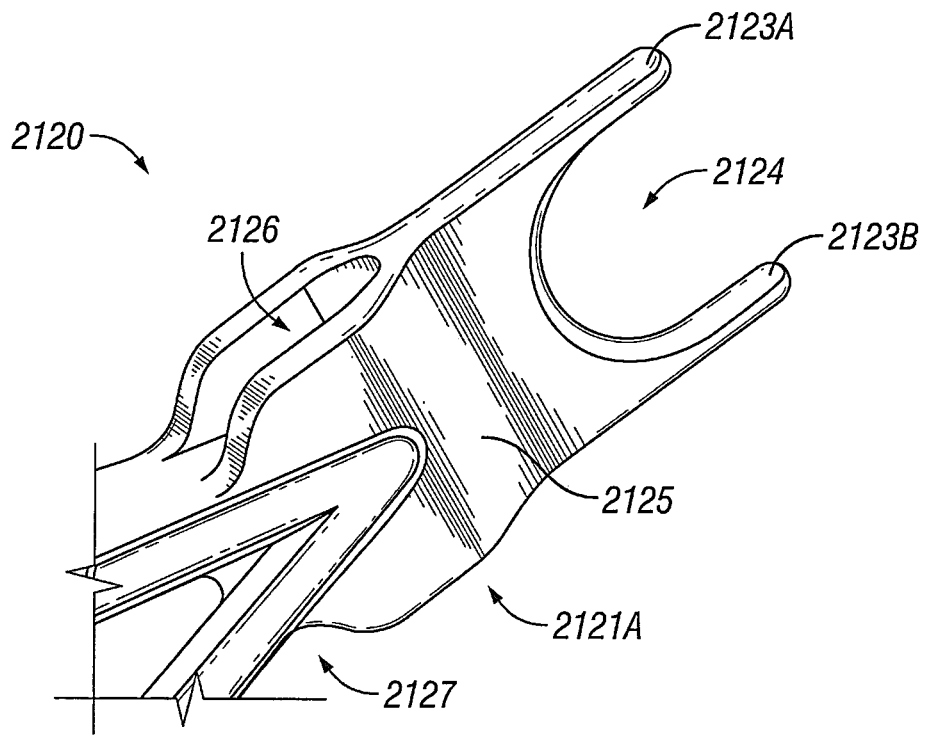
FIG. 21 is an illustration of a selection end or first end of the pull tool.

FIG. 21 is an illustration of a selection end or first end 2121A of the pull tool 2120. The pull tool 2120 may be utilized to pull, shift, adjust, and/or otherwise engage the vessel with the engagement tool (not illustrated). The pull tool 2120 can have a first end 2121A and a second end (not illustrated), with each being distal from the other. The first end 2121A of the pull tool 2120 may be utilized to engage a vessel guide (not illustrated). The first end 2121A of the pull tool 2120 can be utilized to position the vessel guide (not illustrated) through the use of a structured design where the first end 2121A has a male portion 2123A/2123B and the vessel guide (not illustrated) has a female portion. In would be understood, that these portions could be exchanged, meaning the male portion may be on the vessel guide (not illustrated) and the first end 2021A having the female portion. Similarly, the male portion is designed to be inserted into the female portion. For example, the male portion may have two points 2123A/2123B separated by a U-shaped arch 2124 that engages with two apertures that allow for the points to be received by the female portion.

In at least one example, the second end 2121A of the pull tool 2120 can have a ramp section 2125. The ramp section 2125 can allow for the pull tool 2120 to be utilized to separate a vessel guide (not illustrated) from an engagement tool (not illustrated). In at least one embodiment, the ramp section 2125 is dual sided, meaning there is a ramp portion on either side of a center line, where the center line is in the same plane as the U shaped arch 2124 and the points 2123A/2123B. In some other examples, the ramp section 2125 may be one sided based on a center line. The ramp section 2125 may be coupled to an extension section 2126. In at least one example, the extension section 2126 can be generally square or rectangular in shape. In some examples, the extension section 2126 may be two or three sided to allow for connection to couple to other portions of the pull tool 2120.

Figure 22:
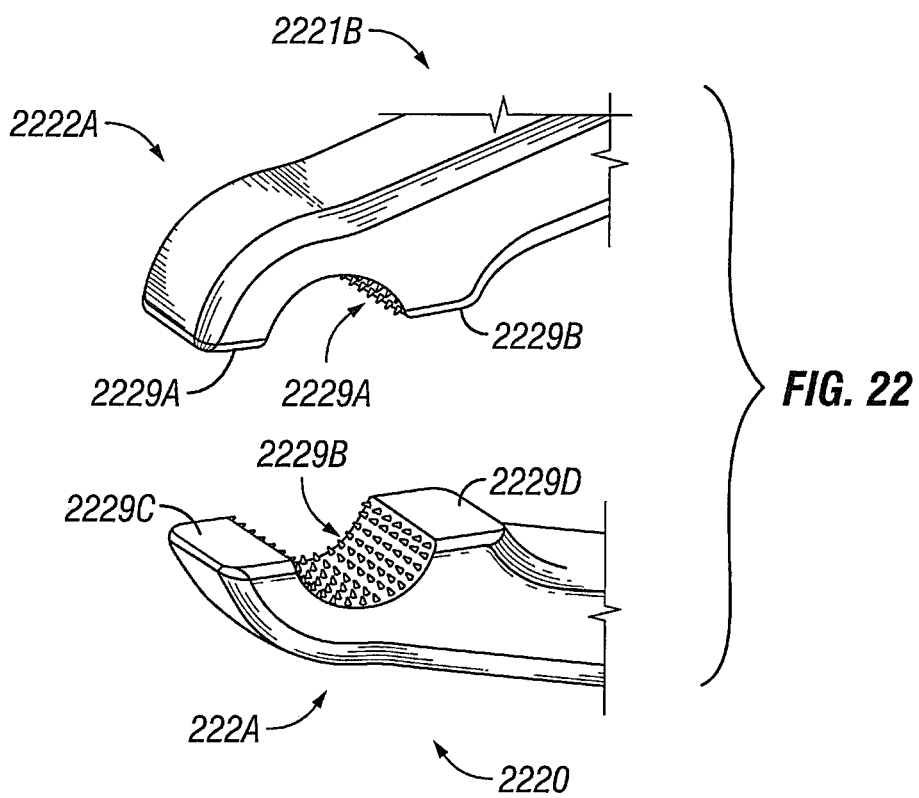
FIG. 22 is an illustration of the tweezer end or second end of the pull tool.

FIG. 22 is an illustration of the tweezer end or second end 2221B of the pull tool 2220. The pull tool 2220 may be utilized to pull, shift, adjust, and/or otherwise engage the vessel with the engagement tool (not illustrated). The pull tool 2220 can have a first end (not illustrated) and a second end 2021B, with each being distal from the other. The first end (not illustrated) of the pull tool 2220 may be utilized to engage a vessel guide (not illustrated).

In at least one embodiment, the pull tool 2220 can have a set of tweezer arms 2222A/2222B at a second end 2221B of the pull tool 2220. The tweezer arms 2222A/2222B may include a surface structure 2228A/2228B (collectively 2228). In at least one example, the surface structure 2228 can have one or more points or raised surfaces that allow for gripping of an object. In some examples, the one or more points or raised surfaces can be atraumatic or traumatic to allow for different types of engagement with a vessel (not illustrated). For simplicity, atraumatic points are those designed to not pierce or damage a lumen of a vessel, or other body part, while traumatic points may or may not pierce or otherwise damage, non-critically, a lumen of a vessel or other body part. In at least one example surface structure 2228A may be traumatic, while surface structure 2228B is atraumatic, or the reverse can be possible as well. These surface structures 2228 can allow for the engagement with one or more vessels, in a manner that can avoid damage to them but also allow them to be utilized with the pull tool and/or pull tool system. A set of touch points 2229A/2229B/2229C/229D can allow for a vessel or other piece to be captured between the tweezer arms 2222A/2222B. In at least one example, the first set of touch points 2229A/2229B are on the tweezer arm 2222A, and the second set of touch points 2229C/2229D are on the tweezer arm 2222B. It should be noted that while vascular and/or microvascular surgeries and/or surgical methods will be described herein, the present disclosure could also be utilized in any number of surgeries, including, but not limited to those for the head, neck, sinus, nasal, ear, heart, lung, arteries, veins, brain, nerves, organs, vessels, and/or any other human or animal surgery. While the description will be related to operations on human, it would be understood that those in the veterinarian field could also benefit from the present disclosure. Some examples of the disclosure may also benefit the plumbing, electrical, or other related fields.

Descriptions herein will be made with respect to a gravitational reference, but such descriptions should not be considered limiting. As it would be understood, unless otherwise noted, a reference to a left or right of an object could be mirrored or flipped similarly unless otherwise noted a reference to up or down could be mirrored or flipped. The stents and/or stent delivery mechanisms disclosed herein can be manufactured, made, and/or formed with any number of materials, including, but not limited to, wood, plastics, silicon, metal, metal alloys, synthetic materials, polymers, absorbable polymers, Teflon, Mylar, carbon fiber, other like materials, or combinations thereof. In at least one example, the stent of the present disclosure are manufactured and/or constructed of biodegradable materials to allow for the disintegration of the stent within a few days, weeks, or months after delivery, such as, but not limited to 1 day, 2 days, 3 days, 5 days, 1 week, 1.5 weeks, 2 weeks, 2.5 weeks, 3 weeks, 4 weeks, 1 month, 5 weeks, six weeks, 7 weeks, 8 weeks, 2 months, 9 weeks, 10 weeks, 11 weeks, 12 weeks, 3 months, 4 months, 6 months, 9 months, or 12 months.

In some versions, the body of a stent is a hollow cylinder, hollow tubular body, or other hollow structure that may have an inner diameter and corresponding inner circumference, and an outer diameter and corresponding outer circumference. The stents of the present disclosure may also include an aperture on one or more ends defined by the body of the stent and more particularly by the inner diameter and/or inner circumference of the stent. It would be understood that the aperture(s) can have many cross-sections and/or profiles, such as but not limited to, a circle, an oval, a square, a rectangle, a polygon, a cone, a pyramid, other shapes or profiles and/or combinations thereof. In one example, the body of the stent(s) may have a top, and a bottom that can be in planes parallel to each other, and a first end, and a second end, wherein the second end is distal from the first end. In alternative examples, the top and bottom of the body of the stent may not be in parallel planes. For example, a vessel may have a narrowed or narrowing section that requires the body of the stent to be smaller at one end, and larger at the other end. Creating a situation where the top would be in a plane that converges with a plane parallel to the bottom of the body of the stent.

Additionally, in at least one version, the stent may include sections that fore the stent body, and each of the stent body sections may be constructed of a different material. The different materials can allow for different expansion or deformation rates for each stent body section for an expandable or modifiable stent. The stent body sections can also be a first stent end section (proximal section), a central stent section (attachment section), and a second stent end section (distal section). It would be understood that the proximal and distal sections may also be reversed in some examples. Each of the end sections may also have their own proximal, attachment, and/or distal sections.

The compression of a modifiable stent can be generated by the materials utilized to form, construct, and/or manufacture the stent. The materials can have an elasticity, or tensile strength based on the modular, sectional, and/or geometrical structure chosen for the specific stent. The modifiable stent body may also have atraumatic anchor(s), and/or traumatic anchor(s) that may be modifiable as well. A device can be utilized to deliver the stent to a donor and/or recipient vessel and initiate a decompression, expansion, and/or modification of the stent properties, the stent body, and/or anchor(s).

The stents of the present disclosure may include a modifiable structure that may be manufactured of a material, such as plastics, silicon, metal, metal alloys, synthetic materials, polymers, absorbable polymers, Teflon, Mylar, carbon fiber, other like materials, or combinations thereof. The material can allow for the modifiable structure to be approximately one-half its normal size, be approximately one-quarter of its normal size, or any other fraction of one whole portion of the modifiable structure. The modifiable structure may also be formed, constructed, and/or manufactured utilizing a material that may have a memory effect or expansion memory such as a pliable plastic or silicon material, but other materials such as plastics, silicon, metal, metal alloys, synthetic materials, polymers, absorbable polymers, Teflon, Mylar, carbon fiber, other like materials, or combinations thereof, may also be utilized. A memory effect or expansion memory can be described as a material that can be manipulated from a first position to a second position and then return to the first position upon release from the second position.

The structure node can provide a connection point for the expandable structure. In at least one example the structure node may be utilized with the expandable structure to create a mesh of nodes. The structure node may be constructed, formed, or manufactured utilizing a material such as, but not limited to, plastics, silicon, metal, metal alloys, synthetic materials, polymers, absorbable polymers, Teflon, Mylar, carbon fiber, other like materials, or combinations thereof. In at least one example, the structure node can be constructed, formed, and/or manufactured with the expandable structure. In alternative examples, the structure node may be connected to, or affixed to the expandable structure through an adhesive, fastener, glue, connector, cement, epoxy, binder, In at least one example, the expandable or modifiable member and/or expandable connection node can be manufactured with magnetic and/or shape memory properties. In at least one example, the connection node may interact with other connection nodes to cause a transformation or modification of an expandable or structural element or member.

The expandable structural element, can be formed, constructed, and/or manufactured utilizing materials, such as, but not limited to, plastics, silicon, metal, metal alloys, synthetic materials, polymers, absorbable polymers, Teflon, Mylar, carbon fiber, other like materials, or combinations thereof. Additionally, the expandable structural element, in one example, may also have a memory effect that can allow the expandable structural element to compressed or stretched from a first position to a second position, and then upon release from the second position to return to the first position.

In alternative examples, the connection node can be formed, constructed, and/or manufactured of a different material than the expandable structural element. The non-expandable structural element may be formed, constructed, and/or manufactured utilizing materials, such as, but not limited to plastics, silicon, metal, metal alloys, synthetic materials, polymers, absorbable polymers, Teflon, Mylar, carbon fiber, other like materials, or combinations thereof. In at least one example, a section of a stent apparatus or a first or second end of a stent apparatus, having a proximal end section, an attachment end section, and a distal end section that can couple to a hollow tubular section or structure of the stent apparatus. An expansion may include a linear expansion or radial expansion.

A cover or sheath that encloses the modifiable stent can maintain the unmodified state, or the properties of the stent elements may be modified to create a memory effect. The stent elements may also be interconnected elements or interconnecting elements. These properties can include, but are not limited to, the chemical structure, magnetic structure, and/or electrical conductivity structure of stent elements. These properties can be modified, to change the geometry of the modifiable stent to a modified state. For example, the transition from an unmodified state to a modified state, can allow for an expansion of the modifiable stent to secure it to the lumen or wall of a vessel, or set of vessels.

The sheath, cover, or transport device may be coupled to a needle to assist in removal of the sheath, cover, or transport device after placing the expandable stent body in a proper location. In one example, the needle removes the sheath, cover, or transport device from a proximal end of the stent body. A donor vessel and/or a recipient vessel can receive the expandable stent.

The expandable stent can be expanded in an accordion, twisting, and/or turning motion. In other examples, the at least one atraumatic anchor(s) can be pliable and/or flexible, allowing one or both ends of the stent to be placed within a vessel (not illustrated) without an expansion and/or delivery tool.

The stents of the present disclosure may comprise spike(s), barb(s), atraumatic anchor(s), prong(s), point(s), pin(s), and/or any combination(s) thereof along an inner or outer surface of the stent. The anchors may be atraumatic or non-puncturing, or a form of puncturing or traumatic anchor. For example, in a low pressure or slow blood flow vessel atraumatic anchors may be used to avoid damage to the vessels with low blood flow through them. In another example, the stent(s) may be utilized in a high pressure or fast blood flow vessel utilizing the anchors to secure the stent in place through the use of a puncturing anchor and/or a combination of puncturing and atraumatic anchors.

During surgeries that allow for end-to-end anastomoses the donor vessel and the recipient vessel can be affixed to the stent via the stent anchor(s) and/or the stent end anchor(s). The vessels do not have to be prepared in a traditional manner because the anchor(s) allow for the securing of the donor vessel and/or the recipient vessel with no need for suturing of the vessels. There is also a decrease in the amount of time required preparing the ends of the vessels. The stent body anchor(s) can be manufactured with a length sufficient to puncture through the lumen or wall of both the donor vessel and the recipient vessel. Similarly, the stent end anchor(s) can be manufactured with a length sufficient to puncture through the lumen or wall of the donor vessel or the recipient vessel. Traumatic anchor(s) would reference an anchor that can puncture or be invasive to the wall or lumen of a vessel, but this would be an acceptable level of injury and/or be minimally invasive to secure the stent in place within a donor and/or recipient vessel. The atraumatic anchor(s) and/or traumatic anchor(s) may be in a compressed or unexpanded state prior to and during initial delivery or installation of the stent.

While this disclosure has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

While various embodiments in accordance with the principles disclosed herein have been described above, it should be understood that they have been presented by way of example only, and not limitation. Thus, the breadth and scope of this disclosure should not be limited by any of the above-described exemplary embodiments but should be defined only in accordance with any claims and their equivalents issuing from this disclosure. Furthermore, the above advantages and features are provided in described embodiments but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Brief Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure but should not be constrained by the headings set forth herein.

We claim:

1. A stent operation system comprising:
   an engagement tool comprising a first arm and a second arm coupled by a hinge point at respective proximate ends, where the first and second arms are kept in a normally closed position by a biasing mechanism;
   a pull tool comprising a first end having a U shape with at least one point for positioning, and a second end having a set of engagement arms;
   a pair of stents, wherein at least one of the stents is modifiable using expandable members permitting at least one of a diameter or length to be modified; and
   a stent delivery tool configured to place the pair of stents onto a vessel, wherein a first stent is placed within the vessel and a second stent is placed outside the vessel.

2. The stent operation system of claim 1, wherein the engagement tool further comprises a vessel guide engaged by the first and second arms at respective distal ends opposite their proximate ends, the vessel guide configured to guide and open a first vessel to allow a second vessel to be received within the first vessel.

3. The stent operation system of claim 2, wherein the vessel guide comprises an upper guide section engaged by the first arm and a lower guide section engaged by the second arm, wherein the upper and lower guide sections are separable by movement of the first and second arms.

4. The stent operation system of claim 3, wherein the upper guide section comprises an upper forward section and the lower guide section comprises a lower forward section, wherein the upper and lower forward sections are each tapered for ease of insertion into the first vessel.

5. The stent operation system of claim 4, wherein each of the upper forward section and lower forward section comprise a corresponding pair of fingers, wherein a first finger of the pair of fingers is longer than the second finger of the pair of fingers.

6. The stent operation system of claim 2, wherein the second end of the pull tool further comprises a first tweezer arm and a second tweezer arm that is separated from the first tweezer arm.

7. The stent operation system of claim 4, wherein the first end of the pull tool is U shaped and sized to engage one or both of the upper guide section around the upper forward section or the lower guide section around the lower forward section.

8. The stent operation system of claim 1, wherein the pair of stents are coaxial to one another when held by the stent delivery tool and when deployed onto the vessel.

9. The stent operation system of claim 1, wherein an inner stent of the pair of stents comprises exterior features configured to engage an interior of the vessel, and an outer stent of the pair of stents is comprises interior features configured to engage an exterior of the vessel.

10. The stent operation system of claim 9, wherein the outer stent further comprises exterior features configured to engage an interior of a second vessel overlapping the first vessel.

11. The stent operation system of claim 1, wherein the first arm and the second arm each further comprise a crossover section, wherein a compressive force applied proximate the first ends causes a separating force at the second ends.

12. The stent operation system of claim 11, wherein the first arm and the second arm each further comprise a reversed section, the reversed sections having respective engagement surfaces facing one another.

13. An engagement tool comprising:
    a first arm and a second arm, each comprising a first end and a second end opposite the first end;
    a hinge point at the first ends connecting the first arm and the second arm; and
    a vessel guide engaged by the first and second arms at the second ends, the vessel guide configured to be received within a first vessel, the vessel guide configured to open, via movement of the first and second arms, to allow a second vessel to be received within the first vessel, wherein the vessel guide further comprises a positioning pin;
    wherein the second ends of the first arm and second arm are kept in a normally closed position with a biasing mechanism.

14. The engagement tool of claim 13, wherein the first arm and the second arm each further comprise a crossover section, wherein a compressive force applied proximate the first ends causes a separating force at the second ends.

15. The engagement tool of claim 14, wherein the first arm and the second arm each further comprise a reversed section, the reversed sections having respective engagement surfaces facing one another.

16. The engagement tool of claim 15, wherein the engagement surfaces are configured to engage corresponding upper and lower sections of the vessel guide, wherein the upper and lower guide sections are separable by movement of the first and second arms.

17. The engagement tool of claim 16, wherein the upper section comprises an upper forward section and the lower section comprises a lower forward section, wherein the upper and lower forward sections are each tapered for ease of insertion into the first vessel.

18. The engagement tool of claim 13, wherein the vessel guide further comprises a set of receiving apertures.

19. The engagement tool of claim 18, wherein the vessel guide further comprises an engagement groove.

20. The engagement tool of claim 18, wherein the positioning pin is received in one of the set of receiving apertures.

* * * * *